(12) United States Patent
Caya et al.

(10) Patent No.: US 11,453,679 B2
(45) Date of Patent: Sep. 27, 2022

(54) METHYL 2-METHYL-5-OXO-1,4,5,7-TETRAHYDROFURO[3,4-B]PYRIDINE-3-CARBOXYLATE COMPOUNDS AS $CA_v1.2$ ACTIVATORS

(71) Applicant: Novartis AG, Basel (CH)

(72) Inventors: Thomas Charles Caya, Somerville, MA (US); James Neef, Stow, MA (US); Tejaskumar Pankajbhai Pathak, Boston, MA (US); Amir Masoud Sadaghiani, Dover, MA (US); Xilin Zhou, Arlington, MA (US)

(73) Assignee: NOVARTIS AG, Basel (CH)

( * ) Notice: Subject to any disclaimer, the term of this patent is extended or adjusted under 35 U.S.C. 154(b) by 0 days.

(21) Appl. No.: 17/345,902

(22) Filed: Jun. 11, 2021

(65) Prior Publication Data
US 2021/0387995 A1    Dec. 16, 2021

Related U.S. Application Data

(60) Provisional application No. 63/039,691, filed on Jun. 16, 2020.

(51) Int. Cl.
*C07D 491/048* (2006.01)

(52) U.S. Cl.
CPC .................. *C07D 491/048* (2013.01)

(58) Field of Classification Search
CPC .................................... C07D 491/048
See application file for complete search history.

(56) References Cited

U.S. PATENT DOCUMENTS

| 4,532,248 A | 7/1985 | Franckowiak et al. |
| 4,567,268 A | 1/1986 | Young |
| 5,026,714 A | 6/1991 | Goldmann et al. |

FOREIGN PATENT DOCUMENTS

| EP | 0111455 A2 | 6/1984 |
| EP | 0158138 A1 | 10/1985 |
| WO | 2010/015037 A1 | 2/2010 |

OTHER PUBLICATIONS

Andrade, A., et al., "Genetic Associations between Voltage-Gated Calcium Channels and Psychiatric Disorders," Int. J. Mol. Sci., 2019, 20, 3537.
Berridge, M., "Calcium signalling and psychiatric disease: bipolar disorder and schizophrenia," Cell Tissue Res, 2014, 357:477-492.
Ferreira et al, "Collaborative genome-wide association analysis supports a role for ANK3 and CACNA1C in bipolar disorder," Nat Genet 40:1056-1058, 2008.
Goerlitzer, K., et al., ;"Anellated lactones form Bay-K-8644 and dihydropyridine byproducts in the Hantzsch synthesis"; Inst. Pharm. Chem., Tech. Univ. Braunschweig, Braunschweig, 3300, Germany (English abstract attached) Archiv der Pharmazie (Weinheim, Germany) (1991), 324(11), 879-86.
Gunduz, M., et al., "Synthesis of cyclopentapyridine and thienopyridine derivatives as potential calcium channel modulators," Arzneimittelforschung. Apr. 2012;62(4):167-75.
Hopp, S., "Targeting microglia L-type voltage-dependent calcium channels for the treatment of central nervous system disorders," J Neurosci Res., Jan. 2021;99(1):141-162.
Ishikawa, et al., "Survival of rat motoneurons in culture by L-type calcium channel agonists, FPL64176 and (S)-Bay K8644," Journal of neurochemistry , 2012, vol. 123, p. 82-83.
Kabir, Z., et al., "From Gene to Behavior: L-Type Calcium Channel Mechanisms Underlying Neuropsychiatric Symptoms," Neurotherapeutics Jul. 2017; 14(3): 588-613.
McInally, T., et al. "A novel, base-induced fragmentation of Hantzsch-type 4-aryl-1,4-dihydropyridines"; Journal of the Chemical Society, Perkin Transactions 1: Organic and Bio-Organic Chemistry (1972-1999) (1988), (7), 1837-44.
Patmore, L., et al., "RS 30026: a potent and effective calcium channel agonist"; British Journal of Pharmacology (1990), 99(4), 687-94.
Sausin'sh, A., et al. "Methods of synthesis of 4-(pyrazolyl)- and 4-(pyridyl)-5-oxo-1,4,5,7-tetrahydrofuro[3,4-b] pyridines"; Chemistry of Heterocyclic Compounds,(1995),(7), pp. 966-972.

(Continued)

*Primary Examiner* — Rebecca L Anderson
(74) *Attorney, Agent, or Firm* — Finnegan, Henderson, Farabow, Garrett & Dunner, LLP

(57) ABSTRACT

The present disclosure provides for a compound according to formula (I)

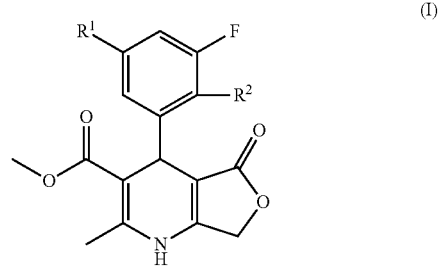

Figure 1:
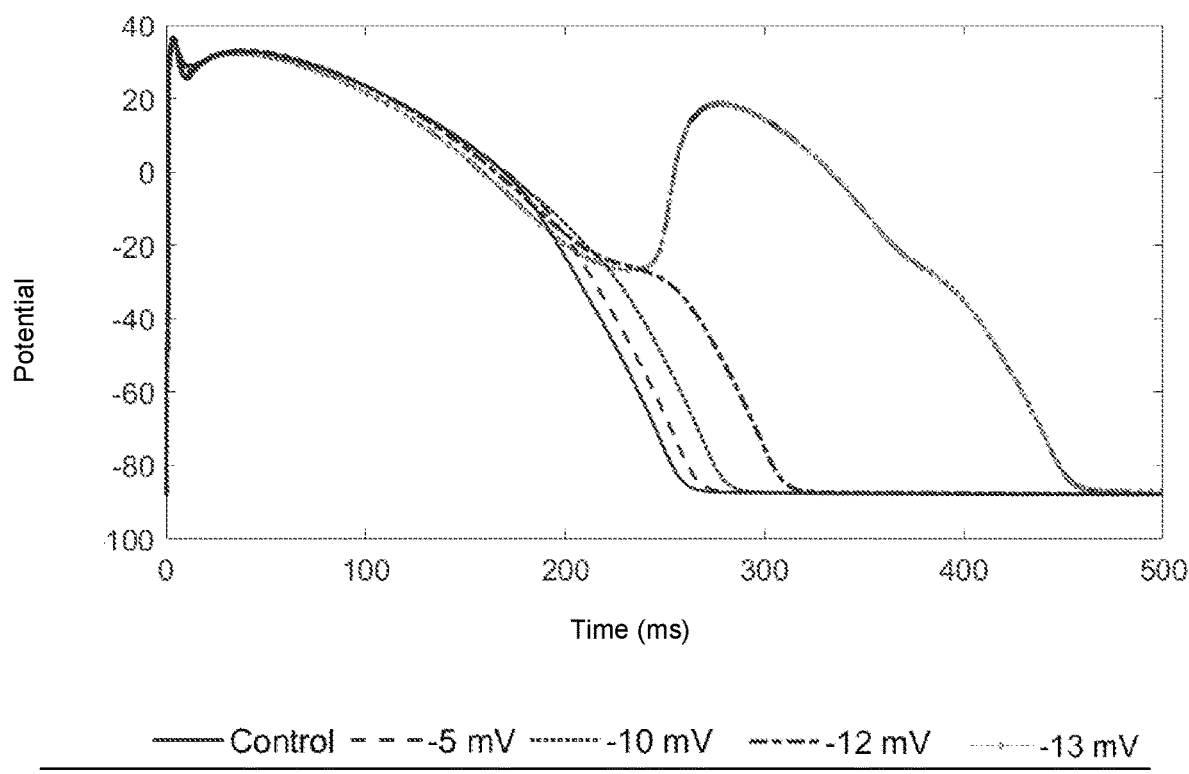

or a pharmaceutically acceptable salt thereof as Cav1.2 activators for the treatment of schizophrenia, bipolar disorder, major depressive disorder, substance use disorder, ADHD, Phelan-McDermid Syndrome, autism spectrum disorder, multiple sclerosis, frontotemporal dementia, Alzheimer's disease, Brugada Syndrome, Short QT syndrome, and early repolarization syndrome.

17 Claims, 2 Drawing Sheets

(56) References Cited

OTHER PUBLICATIONS

Skrastin'sh, I.P., et al. "Bromination of 4-aryl-3,5-bis(alkoxycarbonyl)-2,6-dimethyl-1,4-dihydropyridines"; Chemistry of Heterocyclic Compounds, (1991), (9), 1230-5.
Skrastin'sh, I.P., et al., "Bromination of 2,6-dimethyl-3,5-bis(methoxycarbonyl)-4-[2-(difluoromethoxy)phenyl]-1,4-dihydropyridine (foridone)"; Chemistry of Heterocyclic Compounds, 1989 (7), 948-52.
Skrastin'sh, I.P, et al., "Synthesis and pharmacological activity of furo-1,4-dihydropyridines"; Pharmaceutical Chemistry Journal, (1989), 23(11), 1323-6.
Young, S. D., "Facile conversion of Hantzsch type 4-aryl-2,6-dimethyl-1,4-dihydropyridine-3,5-carboxylates into 4-aryl-2-methyl-5-oxo-1,4,5,7-tetrahydrofuro[3,4-b]pyridine-3-carboxylates"; Merck Sharp and Dohme Res. Lab., West Point, PA; Synthesis (1984), (7), 617-18.
International Search Report and Written Opinion for International Application No. PCT/IB2021/055184, dated Sep. 2, 2021, 13 pages.
International Search Report and Written Opinion for International Application No. PCT/IB2021/055183, dated Aug. 26, 2021, 14 pages.

METHYL 2-METHYL-5-OXO-1,4,5,7-TETRAHYDROFURO[3,4-B]PYRIDINE-3-CARBOXYLATE COMPOUNDS AS $Ca_v1.2$ ACTIVATORS

This application claims the benefit of priority to U.S. Provisional Patent Application No. 63/039,691, filed Jun. 16, 2020, the disclosure of which is incorporated herein by reference in its entirety.

1. FIELD OF THE INVENTION

The present disclosure relates to methyl 2-methyl-5-oxo-1,4,5,7-tetrahydrofuro[3,4-b]pyridine-3-carboxylate compounds, pharmaceutical compositions containing them, and the use of such compounds as $Ca_v1.2$ activators for the treatment of calcium signaling deficit and/or synaptic dysfunction in psychiatric disorders including schizophrenia, bipolar disorder, major depressive disorder, and substance use disorders; neurodevelopmental disorders, such as attention deficit hyperactivity disorder, Phelan-McDermid Syndrome, and other autism spectrum disorders; neurodegenerative disorders, such as multiple sclerosis, frontotemporal dementia, and Alzheimer's disease; and cardiac conditions such as Brugada Syndrome, Short QT syndrome, and early repolarization syndrome.

2. BACKGROUND OF THE INVENTION

Advancements in human genomics have shed light on the genetic basis of psychiatric disorders. Genome wide association studies (GWAS) in schizophrenia have identified over one hundred disease-associated loci, including $Ca_v1.2$ and other genes involved in neuronal calcium signaling. A cross-disorder GWAS analysis has identified $Ca_v1.2$ and its channel-forming beta subunit (CACNB2) as strongly associated with schizophrenia, bipolar disorder, major depressive disorder, ADHD, and autism spectrum disorders. In addition to evidence from GWAS, exome sequencing in patients with schizophrenia showed enrichment of disruptive mutations in $Ca_v1.2$ and other gene members of the neuronal calcium-signaling pathway including the CACNA2D, CACNB, CAMK2 genes. $Ca_v1.2$ has been shown to be important for neuronal differentiation and migration, neurite outgrowth, synaptic signaling, gene expression and brain plasticity. It has been shown to play a role in emotion, learning and memory, executive function, and reward responses of the brain.

$Ca_v1.2$ is broadly expressed throughout the body and plays a major role in multiple organ systems including the cardiovascular system; however, the physiological function of $Ca_v1.2$ in the cardiovascular system is distinct from its function in the brain. Studies have shown that $Ca_v1.2$ is a key contributor to action potential generation in the heart while it is a key driver of intracellular signaling and gene expression in neurons with minimal role in action potential generation. In Timothy Syndrome, $Ca_v1.2$ mutation p.G406R leads to distinct cellular phenotypes between cardiomyocytes and neurons. $Ca_v1.2$ mutations that cause cardiovascular specific disorders (Brugada Syndrome and Long QT syndrome type 8) are further evidence for the divergent functions of $Ca_v1.2$ in heart and brain.

Calcium channel activators have been previously reported, but further investigation into their use for neuropsychiatric disorders has been limited due to their effects on the cardiovascular system. In fact, many of these molecules were initially investigated and developed for their potential therapeutic use in heart failure. Most of the $Ca_v1.2$ SNPs associated from psychiatric GWAS studies reside in introns of the gene, and these risk SNPs have been shown to be associated with reduction of mRNA expression that in many cases results in overall reduction of calcium current amplitude. Therefore, small molecules that can increase the overall current amplitude could be the most beneficial to patients.

3. SUMMARY OF THE INVENTION

The present disclosure provides for a compound according to formula (I)

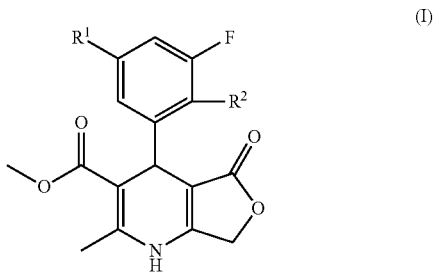

wherein:
$R^1$ is H or halo; and
$R^2$ is ethyl, isopropyl, isopropenyl, cyclopropyl or cyclobutyl each of which is optionally substituted with one to three halo; or a pharmaceutically acceptable salt thereof.

In a second aspect, the disclosure provides a pharmaceutical composition comprising a compound of formula (I) or a pharmaceutically acceptable salt thereof.

In a third aspect, the disclosure provides for a compound of formula (I), or a pharmaceutically acceptable salt thereof for use in therapy, in particular in the treatment of psychiatric disorders including schizophrenia, bipolar disorder, major depressive disorder, and substance use disorders; neurodevelopmental disorders, such as attention deficit hyperactivity disorder, Phelan-McDermid Syndrome, and other autism spectrum disorders; neurodegenerative disorders, such as multiple sclerosis, frontotemporal dementia and Alzheimer's disease; and cardiac conditions such as Brugada Syndrome, Short QT syndrome, and early repolarization syndrome.

In a fourth aspect, the disclosure provides a method for the treatment of psychiatric disorders including schizophrenia, bipolar disorder, major depressive disorder, and substance use disorders; neurodevelopmental disorders, such as attention deficit hyperactivity disorder, Phelan-McDermid Syndrome, and other autism spectrum disorders; neurodegenerative disorders, such as multiple sclerosis, frontotemporal dementia and Alzheimer's disease; and cardiac conditions such as Brugada Syndrome, Short QT syndrome, and early repolarization syndrome comprising administration of an effective amount of a compound according to formula (I), or a pharmaceutically acceptable salt thereof, to a patient in need of treatment thereof.

In a fifth aspect, the disclosures provides for the use of a compound of formula (I) or a pharmaceutically acceptable salt thereof in the manufacture of a medicament for the treatment of psychiatric disorders including schizophrenia, bipolar disorder, major depressive disorder, and substance use disorders; neurodevelopmental disorders, such as attention deficit hyperactivity disorder, Phelan-McDermid Syndrome, and other autism spectrum disorders; neurodegenerative disorders, such as multiple sclerosis, frontotemporal dementia and Alzheimer's disease; and cardiac conditions such as Brugada Syndrome, Short QT syndrome, and early repolarization syndrome.

In a sixth aspect, the disclosures provides a method for the treatment of schizophrenia, bipolar disorder, major depressive disorder, substance use disorder, ADHD, Phelan McDermid Syndrome, autism spectrum disorder, multiple sclerosis, frontotemporal dementia, Alzheimer's disease, Brugada Syndrome, Short QT syndrome, or early repolarization syndrome comprising administration of a compound of formula (I), or a pharmaceutically acceptable salt thereof, to a patient in need of treatment thereof.

4. BRIEF DESCRIPTION OF THE DRAWINGS

FIG. 1: illustrates a simulated cardiac action potentials from an epicardial environment showing the impact of shifting the voltage of $Ca_v1.2$ activation to more negative membrane potentials at a Potential (mV) versus Time (ms).

Figure 2:
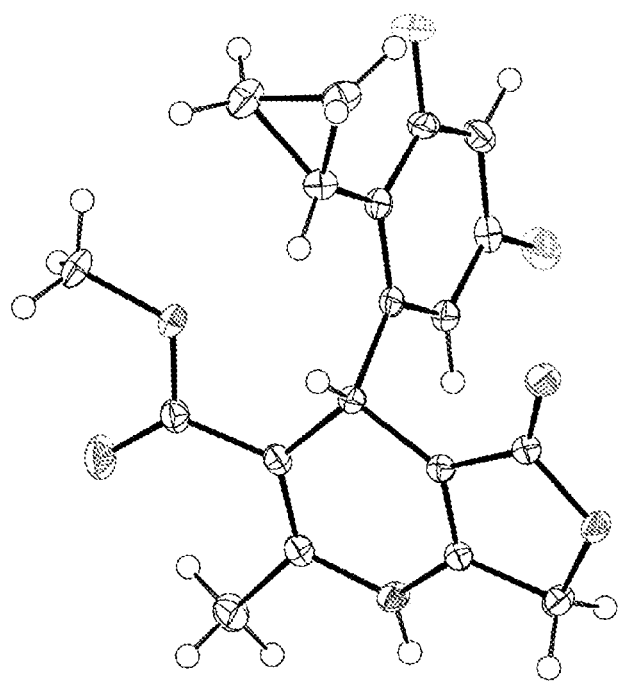

FIG. 2: illustrates the single X-ray crystal of Example 14, methyl 2-methyl-5-oxo-4-phenyl-1,4,5,7-tetrahydrofuro[3,4-b]pyridine-3-carboxylate, confirming that active enantiomer is the S-enantiomer.

5. DETAILED DESCRIPTION OF THE INVENTION

5.1. Definitions

Generally, the nomenclature used herein and the laboratory procedures in organic chemistry, medicinal chemistry, and pharmacology described herein are those well-known and commonly employed in the art. Unless defined otherwise, all technical and scientific terms used herein generally have the same meaning as commonly understood by one of ordinary skill in the art to which this disclosure belongs.

As used herein, "administer" refers to the manner in which a compound described herein is presented to a subject.

As used herein, "optionally substituted" means the group referred to can be substituted at one or more positions by any one or any combination of the radicals listed thereafter.

As used herein, "halo", as used herein, may be fluorine, chlorine, bromine or iodine.

As used herein, "subject" or "patient" refers to a living organism suffering from one or more of the diseases or disorders described here (e.g., psychiatric disorders including schizophrenia, bipolar disorder, major depressive disorder, and substance use disorders; neurodevelopmental disorders, such as attention deficit hyperactivity disorder, Phelan-McDermid Syndrome, and other autism spectrum disorders; neurodegenerative disorders, such as multiple sclerosis, frontotemporal dementia, and Alzheimer's disease; and cardiac conditions such as Brugada Syndrome, Short QT syndrome, and early repolarization syndrome) that can be treated by administration of a pharmaceutical composition described herein. Examples of subjects include mammals (e.g., humans and animals such as dogs, cows, horses, monkeys, pigs, sheep, goats, cats, mice, rabbits, rats, and transgenic non-human animals). In certain embodiments, the subject is a human, e.g., a human suffering from, at risk of suffering from, or potentially capable of suffering from a disease described herein (e.g., psychiatric disorders including schizophrenia, bipolar disorder, major depressive disorder, and substance use disorders; neurodevelopmental disorders, such as attention deficit hyperactivity disorder, Phelan-McDermid Syndrome, and other autism spectrum disorders; neurodegenerative disorders, such as multiple sclerosis, frontotemporal dementia, and Alzheimer's disease; and cardiac conditions such as Brugada Syndrome, Short QT syndrome, and early repolarization syndrome).

Throughout this specification and in the claims that follow, unless the context requires otherwise, the word "comprise", or variations such as "comprises" or "comprising", should be understood to imply the inclusion of a stated integer or step or group of integers or steps but not the exclusion of any other integer or step or group of integers or steps.

If there is a discrepancy between a depicted structure and a chemical name given to that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of the structure of portion of the structure.

5.2. Compounds

A compound according to formula (I)

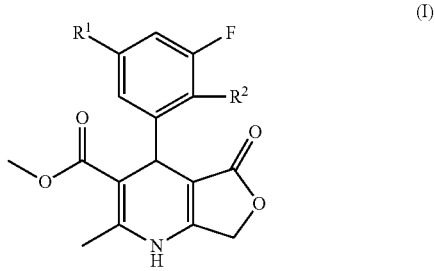

(I)

wherein:

$R^1$ is H or halo; and $R^2$ is ethyl, isopropyl, isopropenyl, cyclopropyl, or cyclobutyl each of which is optionally substituted with one to three halo; or a pharmaceutically acceptable salt thereof.

One embodiment is a compound of formula (Ia)

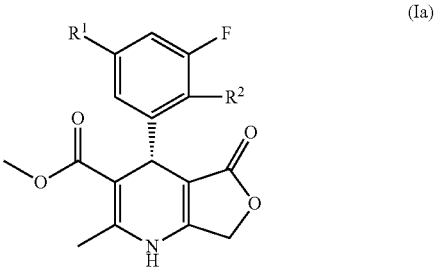

(Ia)

Another embodiment is a compound of formula (Ib)

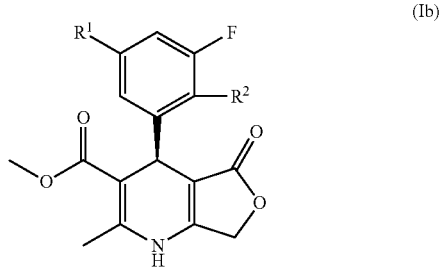

In another embodiment, R$^1$ is H or F.
In another embodiment, R$^1$ is H.
In another embodiment, R$^1$ is F.
In another embodiment, R$^2$ is ethyl, isopropyl, isopropenyl, cyclopropyl or cyclobutyl each of which is optionally substituted with one to three F.
In another embodiment, R$^2$ is cyclopropyl optionally substituted with one to three F.
In another embodiment, R$^2$ is ethyl optionally substituted with one to three F.
In another embodiment, R$^2$ is isopropyl optionally substituted with one to three F.

Specific compounds include:
Methyl (S)-4-(2-((R)-2,2-difluorocyclopropyl)-3-fluorophenyl)-2-methyl-5-oxo-1,4,5,7-tetrahydrofuro[3,4-b]pyridine-3-carboxylate;
Methyl (S)-4-(2-((S)-2,2-difluorocyclopropyl)-3-fluorophenyl)-2-methyl-5-oxo-1,4,5,7-tetrahydrofuro[3,4-b]pyridine-3-carboxylate;
Methyl (S)-4-(2-cyclobutyl-3-fluorophenyl)-2-methyl-5-oxo-1,4,5,7-tetrahydrofuro[3,4-b]pyridine-3-carboxylate;
Methyl (S)-4-(2-cyclopropyl-3-fluorophenyl)-2-methyl-5-oxo-1,4,5,7-tetrahydrofuro[3,4-b]pyridine-3-carboxylate;
Methyl (S)-4-(2-((R)-2,2-difluorocyclopropyl)-3,5-difluorophenyl)-2-methyl-5-oxo-1,4,5,7-tetrahydrofuro[3,4-b]pyridine-3-carboxylate;
Methyl (S)-4-(2-((S)-2,2-difluorocyclopropyl)-3,5-difluorophenyl)-2-methyl-5-oxo-1,4,5,7-tetrahydrofuro[3,4-b]pyridine-3-carboxylate;
Methyl (S)-4-(3,5-difluoro-2-((S)-1-fluoroethyl)phenyl)-2-methyl-5-oxo-1,4,5,7-tetrahydrofuro[3,4-b]pyridine-3-carboxylate;
Methyl (S)-4-(3,5-difluoro-2-((R)-1-fluoroethyl)phenyl)-2-methyl-5-oxo-1,4,5,7-tetrahydrofuro[3,4-b]pyridine-3-carboxylate;
Methyl (S)-4-(3-fluoro-2-(2-fluoropropan-2-yl)phenyl)-2-methyl-5-oxo-1,4,5,7-tetrahydrofuro[3,4-b]pyridine-3-carboxylate;
Methyl (S)-4-(3-fluoro-2-(2,2,2-trifluoroethyl)phenyl)-2-methyl-5-oxo-1,4,5,7-tetrahydrofuro[3,4-b]pyridine-3-carboxylate;
Methyl (S)-4-(3-fluoro-2-((S)-1-fluoroethyl)phenyl)-2-methyl-5-oxo-1,4,5,7-tetrahydrofuro[3,4-b]pyridine-3-carboxylate;
Methyl (S)-4-(3-fluoro-2-((R)-1-fluoroethyl)phenyl)-2-methyl-5-oxo-1,4,5,7-tetrahydrofuro[3,4-b]pyridine-3-carboxylate;
Methyl (S)-4-(2-((R)-1,2-difluoroethyl)-3-fluorophenyl)-2-methyl-5-oxo-1,4,5,7-tetrahydrofuro[3,4-b]pyridine-3-carboxylate;
Methyl (S)-4-(2-((S)-1,2-difluoroethyl)-3-fluorophenyl)-2-methyl-5-oxo-1,4,5,7-tetrahydrofuro[3,4-b]pyridine-3-carboxylate;
Methyl (S)-4-(2-ethyl-3,5-difluorophenyl)-2-methyl-5-oxo-1,4,5,7-tetrahydrofuro[3,4-b]pyridine-3-carboxylate;
Methyl (S)-4-(2-ethyl-3-fluorophenyl)-2-methyl-5-oxo-1,4,5,7-tetrahydrofuro[3,4-b]pyridine-3-carboxylate;
(S)-methyl 4-(2-cyclopropyl-3,5-difluorophenyl)-2-methyl-5-oxo-1,4,5,7-tetrahydrofuro[3,4-b]pyridine-3-carboxylate;
(S)-methyl 4-(3-fluoro-2-isopropylphenyl)-2-methyl-5-oxo-1,4,5,7-tetrahydrofuro[3,4-b]pyridine-3-carboxylate;
(S)-methyl 4-(3-fluoro-2-(3,3,3-trifluoroprop-1-en-2-yl)phenyl)-2-methyl-5-oxo-1,4,5,7-tetrahydrofuro[3,4-b]pyridine-3-carboxylate;
(S)-methyl 4-(2-(2,2-difluoroethyl)-3-fluorophenyl)-2-methyl-5-oxo-1,4,5,7-tetrahydrofuro[3,4-b]pyridine-3-carboxylate;
Methyl (S)-4-(3,5-difluoro-2-isopropylphenyl)-2-methyl-5-oxo-1,4,5,7-tetrahydrofuro[3,4-b]pyridine-3-carboxylate;
(S)-methyl 4-(3,5-difluoro-2-(3,3,3-trifluoroprop-1-en-2-yl)phenyl)-2-methyl-5-oxo-1,4,5,7-tetrahydrofuro[3,4-b]pyridine-3-carboxylate; and
Methyl (S)-4-(3-fluoro-2-(3-fluorocyclobutyl)phenyl)-2-methyl-5-oxo-1,4,5,7-tetrahydrofuro[3,4-b]pyridine-3-carboxylate.

Depending on the choice of the starting materials and procedures, the compounds can be present in the form of one of the possible stereoisomers or as mixtures thereof, for example as pure optical isomers, or as stereoisomer mixtures, such as racemates and diastereoisomer mixtures, depending on the number of asymmetric carbon atoms. The present disclosure is meant to include all such possible stereoisomers, including racemic mixtures, diasteriomeric mixtures and optically pure forms. Optically active (R)- and (S)-stereoisomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

As used herein, the terms "salt" or "salts" refers to an acid addition or base addition salt of a compound of the present disclosure. "Salts" include in particular "pharmaceutically acceptable salts". The term "pharmaceutically acceptable salts" refers to salts that retain the biological effectiveness and properties of the compounds of this disclosure and, which typically are not biologically or otherwise undesirable. In many cases, the compounds of the present disclosure are capable of forming acid and/or base salts by virtue of the presence of amino and/or carboxyl groups or groups similar thereto.

Pharmaceutically acceptable acid addition salts can be formed with inorganic acids and organic acids.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like.

Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

In another aspect, the present disclosure provides compounds of the present disclosure in acetate, ascorbate, adipate, aspartate, benzoate, besylate, bromide/hydrobromide, bicarbonate/carbonate, bisulfate/sulfate, camphorsulfonate, caprate, chloride/hydrochloride, chlortheophyllonate, citrate, ethandisulfonate, fumarate, gluceptate, gluconate, glucuronate, glutamate, glutarate, glycolate, hippurate, hydroiodide/iodide, isethionate, lactate, lactobionate, laurylsulfate, malate, maleate, malonate, mandelate, mesylate, methylsulphate, mucate, naphthoate, napsylate, nicotinate, nitrate, octadecanoate, oleate, oxalate, palmitate, pamoate, phosphate/hydrogen phosphate/dihydrogen phosphate, polygalacturonate, propionate, sebacate, stearate, succinate, sulfosalicylate, sulfate, tartrate, tosylate trifenatate, trifluoroacetate or xinafoate salt form.

Compounds of the disclosure, i.e. compounds of formula (I) that contain groups capable of acting as donors and/or acceptors for hydrogen bonds may be capable of forming co-crystals with suitable co-crystal formers. These co-crystals may be prepared from compounds of formula (I) by known co-crystal forming procedures. Such procedures include grinding, heating, co-subliming, co-melting, or contacting in solution compounds of formula (I) with the co-crystal former under crystallization conditions and isolating co-crystals thereby formed. Suitable co-crystal formers include those described in WO 2004/078163. Hence the disclosure further provides co-crystals comprising a compound of formula (I).

Furthermore, the compounds of the present disclosure, including their salts, can also be obtained in the form of their hydrates, or include other solvents used for their crystallization. The compounds of the present disclosure may inherently or by design form solvates with pharmaceutically acceptable solvents (including water); therefore, it is intended that the disclosure embrace both solvated and unsolvated forms. The term "solvate" refers to a molecular complex of a compound of the present disclosure (including pharmaceutically acceptable salts thereof) with one or more solvent molecules. Such solvent molecules are those commonly used in the pharmaceutical art, which are known to be innocuous to the recipient, e.g., water, ethanol, and the like. The term "hydrate" refers to the complex where the solvent molecule is water.

The disclosure includes unlabeled forms as well as isotopically labeled forms of compounds of formula (I). Isotopically labeled compounds have structures depicted by the formulae given herein except that one or more atoms are replaced by an atom having a selected atomic mass or mass number. Isotopes that can be incorporated into compounds of the disclosure include, for example, isotopes of hydrogen.

Further, incorporation of certain isotopes, particularly deuterium (i.e., $^2$H or D) may afford certain therapeutic advantages resulting from greater metabolic stability, for example increased in vivo half-life or reduced dosage requirements or an improvement in therapeutic index or tolerability. It is understood that deuterium in this context is regarded as a substituent of a compound of the present disclosure. The concentration of deuterium, may be defined by the isotopic enrichment factor. The term "isotopic enrichment factor" as used herein means the ratio between the isotopic abundance and the natural abundance of a specified isotope. If a substituent in a compound of this disclosure is denoted as being deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation). It should be understood that the term "isotopic enrichment factor" can be applied to any isotope in the same manner as described for deuterium.

For example, formula (I) is deuterated as shown in formula (II):

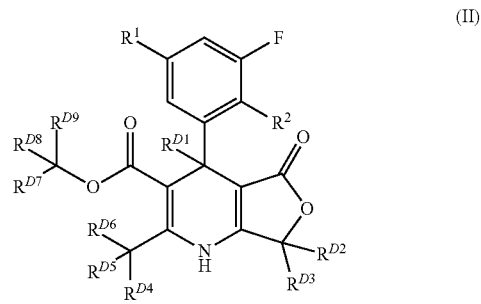

(II)

or a pharmaceutically acceptable salt thereof, wherein $R^1$ and $R^2$ are as defined in formula (I); $R^{D1}$ through $R^{D9}$ are each independently H or D.

Other examples of isotopes that can be incorporated into compounds of the disclosure include isotopes of hydrogen, carbon, nitrogen, oxygen, phosphorous, fluorine, and chlorine, such as $^3$H, $^{11}$C, $^{13}$C, $^{14}$C, $^{15}$N, $^{18}$F, $^{31}$P, $^{32}$P, $^{35}$S, $^{36}$Cl, $^{123}$I, $^{124}$I, $^{125}$I respectively. Accordingly it should be understood that the disclosure includes compounds that incorporate one or more of any of the aforementioned isotopes, including for example, radioactive isotopes, such as $^3$H and $^{14}$C, or those into which non-radioactive isotopes, such as $^2$H and $^{13}$C are present. Such isotopically labelled compounds are useful in metabolic studies (with $^{14}$C), reaction kinetic studies (with, for example $^2$H or $^3$H), detection or imaging techniques, such as positron emission tomography (PET) or single-photon emission computed tomography (SPECT) including drug or substrate tissue distribution assays, or in radioactive treatment of patients. In particular, an $^{18}$F or labeled compound may be particularly desirable for PET or SPECT studies. Isotopically-labeled compounds of the present disclosure can generally be prepared by conventional techniques known to those skilled in the art or by processes analogous to those described in the accompanying Examples and Preparations using an appropriate isotopically-labeled reagents in place of the non-labeled reagent previously employed.

Any asymmetric atom (e.g., carbon or the like) of the compound(s) of the present disclosure can be present in racemic or enantiomerically enriched, for example the (R)-, (S)- or (Re-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated double bonds may, if possible, be present in cis-(Z)- or trans-(E)-form.

Accordingly, as used herein a compound of the present disclosure can be in the form of one of the possible stereoisomers, rotamers, atropisomers, tautomers or mixtures thereof, for example, as substantially pure geometric (cis or trans) stereoisomers, diastereomers, optical isomers (antipodes), racemates or mixtures thereof.

Any resulting mixtures of stereoisomers can be separated on the basis of the physicochemical differences of the constituents, into the pure or substantially pure geometric or optical isomers, diastereomers, racemates, for example, by chromatography and/or fractional crystallization.

Any resulting racemates of compounds of the present disclosure or of intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present disclosure into their optical antipodes, e.g., by fractional crystallization of a salt formed with an optically active acid, e.g., tartaric acid, dibenzoyl tartaric acid, diacetyl tartaric acid, di-0,0-p-toluoyl tartaric acid, mandelic acid, malic acid or camphor-10-sulfonic acid. Racemic compounds of the present disclosure or racemic intermediates can also be resolved by chiral chromatography, e.g., high pressure liquid chromatography (HPLC) using a chiral adsorbent.

5.3. Methods of Use

The compounds of the present disclosure in free form or in pharmaceutically acceptable salt form, exhibit valuable pharmacological properties, e.g. $Ca_v1.2$ activation properties, e.g. as indicated in vitro and in vivo tests as provided in the next sections, and are therefore indicated for therapy or for use as research chemicals, e.g. as tool compounds.

Compounds of the present disclosure may be useful in the treatment of an indication selected from the following list: psychiatric disorders including schizophrenia, bipolar disorder, major depressive disorder, and substance use disorders;

neurodevelopmental disorders, such as attention deficit hyperactivity disorder, Phelan-McDermid Syndrome and other autism spectrum disorders; and neurodegeneration disorders, such as multiple sclerosis, frontotemporal dementia and Alzheimer's disease and cardiac conditions, such as Brugada Syndrome, Short QT syndrome, and early repolarization syndrome. In one embodiment, the indication is a psychiatric disorder such as schizophrenia, bipolar disorder, major depressive disorder, and substance use disorders. In another embodiment, the indication is schizophrenia or bipolar disorder.

Thus, as a further aspect, the present disclosure provides the use of a compound of the present disclosure or a pharmaceutically acceptable salt thereof in therapy. In a further embodiment, the therapy is selected from a disease which may be treated by activation of $Ca_v1.2$. In another embodiment, the disease is selected from the afore-mentioned list of indications.

Thus, as a further aspect, the present disclosure provides a compound of the present disclosure or a pharmaceutically acceptable salt thereof for use in therapy. In a further embodiment, the therapy is selected from a disease which may be treated by activation of $Ca_v1.2$. In another embodiment, the disease is selected from the afore-mentioned list of indications.

In another aspect, the disclosure provides a method of treating a disease which is treated by activation of $Ca_v1.2$ comprising administration of a therapeutically effective amount of a compound of the present disclosure or a pharmaceutically acceptable salt thereof. In a further embodiment, the disease is selected from the afore-mentioned list of indications.

In another aspect, the disclosure provides a method of treating a disease which is treated by activation of $Ca_v1.2$ comprising administration of a compound of the present disclosure or a pharmaceutically acceptable salt thereof. In a further embodiment, the disease is selected from the afore-mentioned list of indications.

Thus, as a further aspect, the present disclosure provides the use of a compound of the present disclosure or a pharmaceutically acceptable salt thereof for the manufacture of a medicament. In a further embodiment, the medicament is for treatment of a disease which may be treated by activation of $Ca_v1.2$. In another embodiment, the disease is selected from the afore-mentioned list of indications.

In another aspect, the present disclosure provides a method for the treatment of schizophrenia, bipolar disorder, major depressive disorder, substance use disorder, ADHD, Phelan McDermid Syndrome, autism spectrum disorder, multiple sclerosis, frontotemporal dementia, Alzheimer's disease, Brugada Syndrome, Short QT syndrome, or early repolarization syndrome which is treated by activation of $Ca_v1.2$ comprising administration of a therapeutically effective amount of a compound of the present disclosure or a pharmaceutically acceptable salt thereof.

In another aspect, the present disclosure provides a method for the treatment of schizophrenia, bipolar disorder, major depressive disorder, substance use disorder, ADHD, Phelan McDermid Syndrome, autism spectrum disorder, multiple sclerosis, frontotemporal dementia, Alzheimer's disease, Brugada Syndrome, Short QT syndrome, or early repolarization syndrome which is treated by activation of $Ca_v1.2$ comprising administration of a compound of the present disclosure or a pharmaceutically acceptable salt thereof.

Thus, as a further aspect, the present disclosure provides the use of a compound of the present disclosure or a pharmaceutically acceptable salt thereof for treating a disease selected from schizophrenia, bipolar disorder, major depressive disorder, substance use disorder, ADHD, Phelan McDermid Syndrome, autism spectrum disorder, multiple sclerosis, frontotemporal dementia, Alzheimer's disease, Brugada Syndrome, Short QT syndrome, or early repolarization syndrome.

Thus, as a further aspect, the present disclosure provides a compound of the present disclosure or a pharmaceutically acceptable salt thereof for use in treating a disease selected from schizophrenia, bipolar disorder, major depressive disorder, substance use disorder, ADHD, Phelan McDermid Syndrome, autism spectrum disorder, multiple sclerosis, frontotemporal dementia, Alzheimer's disease, Brugada Syndrome, Short QT syndrome, or early repolarization syndrome.

In another aspect, the present disclosure provides a method for the treatment of schizophrenia, bipolar disorder, major depressive disorder, substance use disorder, ADHD, Phelan McDermid Syndrome, autism spectrum disorder, multiple sclerosis, frontotemporal dementia, Alzheimer's disease, Brugada Syndrome, Short QT syndrome, or early repolarization syndrome comprising administration of a therapeutically effective amount of a compound of the present disclosure or a pharmaceutically acceptable salt thereof.

In another aspect, the present disclosure provides a method for the treatment of schizophrenia, bipolar disorder, major depressive disorder, substance use disorder, ADHD, Phelan McDermid Syndrome, autism spectrum disorder, multiple sclerosis, frontotemporal dementia, Alzheimer's disease, Brugada Syndrome, Short QT syndrome, or early repolarization syndrome comprising administration of a compound of the present disclosure or a pharmaceutically acceptable salt thereof.

Thus, as a further aspect, the present disclosure provides the use of a compound of the present disclosure or a pharmaceutically acceptable salt thereof for the manufacture of a medicament. for treatment of schizophrenia, bipolar disorder, major depressive disorder, substance use disorder, ADHD, Phelan McDermid Syndrome, autism spectrum disorder, multiple sclerosis, frontotemporal dementia, Alzheimer's disease, Brugada Syndrome, Short QT syndrome, or early repolarization syndrome.

5.4. Pharmaceutical Compositions

In another aspect, the present disclosure provides a pharmaceutical composition comprising a compound of the present disclosure, or a pharmaceutically acceptable salt thereof, and a pharmaceutically acceptable carrier. In a further embodiment, the composition comprises at least two pharmaceutically acceptable carriers, such as those described herein. The pharmaceutical composition can be formulated for particular routes of administration such as oral administration, parenteral administration (e.g. by injection, infusion, transdermal or topical administration), and rectal administration. Topical administration may also pertain to inhalation or intranasal application. The pharmaceutical compositions of the present disclosure can be made up in a solid form (including, without limitation, capsules, tablets, pills, granules, powders or suppositories), or in a liquid form (including, without limitation, solutions, suspensions or emulsions). Tablets may be either film coated or enteric coated according to methods known in the art. Typically, the pharmaceutical compositions are tablets or gelatin capsules comprising the active ingredient together with one or more of:

a) diluents, e.g., lactose, dextrose, sucrose, mannitol, sorbitol, cellulose and/or glycine;
b) lubricants, e.g., silica, talcum, stearic acid, its magnesium or calcium salt and/or polyethyleneglycol; for tablets also
c) binders, e.g., magnesium aluminum silicate, starch paste, gelatin, tragacanth, methylcellulose, sodium carboxymethylcellulose and/or polyvinylpyrrolidone; if desired
d) disintegrants, e.g., starches, agar, alginic acid or its sodium salt, or effervescent mixtures; and
e) absorbents, colorants, flavors and sweeteners.

The pharmaceutical composition or combination of the present disclosure can be in unit dosage of about 1-1000 mg of active ingredient(s) for a subject of about 50-70 kg, or about 1-500 mg or about 1-250 mg or about 1-150 mg or about 0.5-100 mg, or about 1-50 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys or isolated organs, tissues and preparations thereof. The compounds of the present disclosure can be applied in vitro in the form of solutions, e.g., aqueous solutions, and in vivo either enterally, parenterally, advantageously intravenously, e.g., as a suspension or in aqueous solution. The dosage in vitro may range between about $10^{-3}$ molar and $10^{-9}$ molar concentrations. A therapeutically effective amount in vivo may range depending on the route of administration, between about 0.1-500 mg/kg, or between about 1-100 mg/kg.

6. INTERMEDIATES AND EXAMPLES

The following examples are intended to illustrate the disclosure and are not to be construed as being limitations thereon.

The examples were all separated into their single enantiomers and were tested in the Sophion QPatch assay described in the Biological Data section below. However, the stereochemistry of each entantiomer was not determined. The stereochemistry of Example 14, methyl 2-methyl-5-oxo-4-phenyl-1,4,5,7-tetrahydrofuro[3,4-b]pyridine-3-carboxylate, was determined by single crystal x-ray crystallographic analysis and it confirmed that active enantiomer is the S-enantiomer (FIG. 2). Therefore, it is assumed that the S-enantiomer of methyl 2-methyl-5-oxo-4-phenyl-1,4,5,7-tetrahydrofuro[3,4-b]pyridine-3-carboxylate, depicted below, is the active enantiomer in all of the Examples.

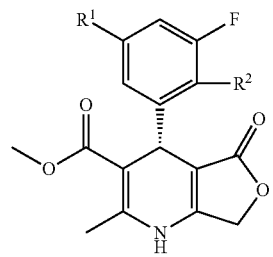

Methyl (S)-2-methyl-5-oxo-4-phenyl-1,4,5,7-tetrahydrofuro[3,4-b]pyridine-3-carboxylate Example numbers (Example 1, 2, 3, etc.) are given for the active enantiomers which are all assumed to have the S-configuration. All other isomers isolated from the synthesis were given example numbers with letters (Example 1b, 2b, 3b etc.). Although there is strong evidence to suggest that the S-configuration is the desired stereochemistry, there is still the chance that the R-enantiomer could be the active enantiomer in some of the Examples.

Temperatures are given in degrees Celsius. If not mentioned otherwise, all evaporations are performed under reduced pressure, typically between about 15 mm Hg and 100 mm Hg (=20-133 mbar). The structure of final products, intermediates and starting materials is confirmed by standard analytical methods, e.g., microanalysis and spectroscopic characteristics, e.g., MS, IR, NMR.

All starting materials, building blocks, reagents, acids, bases, dehydrating agents, solvents, and catalysts utilized to synthesis the compounds of the present disclosure are either commercially available or can be produced by organic synthesis methods known to one of ordinary skill in the art. Further, the compounds of the present disclosure can be produced by organic synthesis methods known to one of ordinary skill in the art as shown in the following examples. Abbreviations used are those conventional in the art or the following:

$^1$H NMR proton nuclear magnetic resonance
AUX auxiliary subunit of $Ca_v1.2$ channel
C Celsius
CD3OD methanol-d4
CDCl3 chloroform-d
CHO Chinese Hamster Ovary cells
Ct threshold cycle in a quantitative polymerase chain reaction assay
d doublet
DAST diethylaminosulfur trifluoride
DCM dichloromethane
dd doublet of doublets
DME 1,4-dimethoxyethane
DMEM Dulbecco's Modified Eagle Medium
DMF N,N-dimethylformamide
DMSO dimethylsulfoxide
DMSO-d6 dimethylsulfoxide-d6
D-PBS Dulbecco's Phosphate Buffered Saline
EC50 Half maximal effective concentration
EDTA Ethylenediaminetetraacetic acid
EGTA Ethylene glycol-bis(β-aminoethyl ether)-N,N,N',N'-tetraacetic acid
Eq equivalents
EtOAc ethyl acetate
FAM 6-carboxyfluorescein
FCS Furin Cleavage Site
FRT Flippase recognition target site
g gram
h hour(s)
$H_2O$ water
HEPES 4-(2-hydroxyethyl)-1-piperazineethanesulfonic acid
HOBt 1-hydroxy-7-azabenzotriazole
HPLC high pressure liquid chromatography
HRMS high resolution mass spectrometry
Hrs hours
Hz hertz
IACUC Institutional Animal Care and Use Committee
IPA isopropyl alcohol
kg kilogram
L liter
LCMS liquid chromatography mass spectrometry
M molar
m multiplet
m/z mass to charge ratio
mg milligram
MHz mega hertz
min minutes
mL milliliter
ml milliliter
mL/min milliliters per minute
mm millimeter
mM millimolar
mmol millimoles
mRNA messenger ribonucleic acid
MS mass spectrometry
mV millivolt
μl microliter
N normal
n-BuLi n-butyllithium
NMR nuclear magnetic resonance
NOESY nuclear Overhauser effect spectroscopy
pCMV the cytomegalovirus promoter
P2A a peptide self-cleavage sequence derived from porcine teschovirus-1
PdCl2(dppf) Dichloro[1,1'-bis(diphenylphosphino)ferrocene]palladium(II)
PD Pharmacodynamics
PK Pharmacokinetics
ppm parts per million
PyBOP benzotriazol-1-yloxytripyrrolidinophosphonium hexafluorophosphate
QT the time interval between the Q wave and T wave of an electrocardiograph
rac racemic
rpm round per minute
RNA ribonucleic acid
RT room temperature
Rt retention time
RT-PCR Reverse Transcription-Polymerase Chain Reaction
s singlet
SFC supercritical fluid chromatography
SFM Serum Free Medium
SNP Single Nucleotide Polymorphism
t triplet
TFA trifluoroacetic acid
THF tetrahydrofuran
THF tetrahydrofuran
uL microliter
Um micrometer
UPLC ultra performance liquid chromatography
UV ultraviolet
VIC 2'-chloro-7'phenyl-1,4-dichloro-6-carboxy-fluorescein
v/v volume/volume percent Small Molecule X-Ray Crystallography
Data Collection Intensity data were collected at 100 K on a Bruker AXS three-circle diffractometer with monochromated Cu(Kα)-radiation, microfocus rotating anode generator, and a Smart 6000 CCD detector using the SMART software (Bruker AXS (2003)). 16 ω-scans at different ϕ-Positions were performed to ensure appropriate data redundancy. Data processing and global cell refinement were performed with Saint (Bruker AXS (2012)). A semi-empirical absorption correction was applied, based on the intensities of symmetry-related reflections measured at different angular settings, using SADABS version 2016/2 (Krause L (2015)). The extinction coefficient refined to 0.00048(11). Crystal data, data collection parameters, and convergence results are listed.

Structure Solution and Refinement

The structure was solved by dual space-recycling methods and subsequent DF syntheses and refined based on full-matrix least-squares on F2 using the SHELXTL program suite (Sheldrick G M (2001)) with SHELXL-2013/4.

REFERENCES

Allen F H, Kennard O, Watson D et al (1987) Tables of Bond Lengths determined by X-Ray and Neutron Diffraction.

Part 1, Bond Lengths in Organic Compounds. J. Chem. Soc. Perkin Trans II; S1-S19.

Bruker AXS (2005) SMART V5.632. Bruker AXS Inc., Madison, Wis., USA.

Bruker AXS (2012) SAINT V7.36A. Bruker AXS Inc., Madison, Wis., USA.

Krause L, Herbst-Irmer R, Sheldrick G M et al (2015) Comparison of silver and molybdenum microfocus X-ray sources for single-crystal structure determination. J. Appl. Cryst.; 48: 3-10.

Spek A L (2003) Single-crystal structure validation with the program PLATON. J. Appl. Cryst.; 36: 7-13.

Sheldrick G M (2001) SHELXTL V6.12. Bruker AXS Inc. Madison, Wis., USA.

LCMS Method 1:
Instrument: Waters Acquity UPLC, photodiode array detector; Column: Acquity UPLC BEH $C_{18}$ 1.7 µm, 21×30 mm; 2 min run time, 2% solvent B from 0 to 0.1 min, 2→98% solvent B:solvent A from 0.1 to 1.8 min, 98% solvent B for 0.2 min. Solvents: Solvent A=0.1% formic acid in water (v/v), Solvent B=0.1% formic acid in acetonitrile (v/v). Injection volume 2-5 uL; UV detection array 210-400, Mass detection 120-1250 (electrospray ionization); column at 50° C.; flow rate 1.0 mL/min.

LCMS Method 2:
Instrument: Waters Acquity UPLC, photodiode array detector; Column: Acquity UPLC BEH $C_{18}$ 1.7 µm 21×50 mm; 2 min run time, 2% solvent B from 0 to 0.1 min, 2→98% solvent B:solvent A from 0.1 to 1.8 min, 98% solvent B for 0.2 min. Solvents: Solvent A=5 mM ammonium hydroxide in water, solvent B=5 mM ammonium hydroxide in acetonitrile. Injection volume 2-5 uL; UV detection array 210-400, Mass detection 120-1250 (electrospray ionization); column at 50° C.; flow rate 1.0 mL/min.

LCMS Method 3:
Instrument: Waters Acquity UPLC, photodiode array detector; Column Acquity UPLC BEH $C_{18}$ 1.7 µm 21×30 mm; 5.2 min run time, 2→98% solvent B:solvent A from 0 to 5.15 min, 98% solvent B from 5.15 to 5.20 min. Solvents: Solvent A=0.1% formic acid in water (v/v), solvent B=0.1% formic acid in acetonitrile (v/v). Injection volume 2-5 uL; UV detection array 210-400, Mass detection 120-1600; column at 50° C., flow rate 1.0 mL/min.

LCMS Method 4:
Instrument: Waters Acquity UPLC, photodiode array detector; Column Acquity UPLC BEH $C_{18}$ 1.7 µm 21×30 mm; 5.2 min run time, 2→98% solvent B:solvent A from 0 to 5.15 min, 98% solvent B from 5.15 to 5.20 min. Solvents: Solvent A=5 mM ammonium hydroxide in water, solvent B=5 mM ammonium hydroxide in acetonitrile). Injection volume 2-5 uL; UV detection array 210-400, Mass detection 120-1600; column at 50° C., flow rate 1.0 mL/min.

LCMS Method 5:
Instrument: Agilent 1200 LC/G1956A, diode array detector; Column: Chromolith Flash $C_{18}$, 1.6 micron 2×25 mm; 1.5 minute run time, 5→95% solvent B:solvent A from 0→1.2 minutes and then 95% solvent B from 1.21→1.5 minutes. Solvents: Solvent A=0.0375% TFA in Water (v/v), Solvent B=0.01875% TFA in Acetonitrile (v/v). Injection volume 2-5 uL; UV detection 220 and 254 nM, Mass detection 100-1000 (electrospray ionization); column at 50° C.; Flow rate 1.5 mL/min.

LCMS Method 6:
Instrument: SHIMADZU LCMS-2020, photodiode array detector; Column: Kinetex EVO $C_{18}$, 5 µm, 1×30 mm; 1.55 minute run time, 5→95% solvent B:solvent A from 0→1.20 minutes and then 95% solvent B from 1.21 minutes to 1.55 minutes. Solvents: Solvent A=0.025% $NH_4OH$ in water (v/v), Solvent B=acetonitrile. Injection volume 2-5 uL; UV detection 220 and 254 nM, Mass detection 100-1000 (electrospray ionization); column at 40° C.; Flow rate 1.5 mL/min.

LCMS Method 7:
Instrument: API2000, column: Mercury MS Synergi 2 µm, 20×4.0 mm, C12; gradient: A—0.1% formic acid in water/B—acetonitrile: Time/% B: 0.0/30, 0.5/30, 1.5/95, 2.0/95, 2.5/30, 3.0/30, flow 2.0 mL/min; UV detection array 190-400, Mass detection 100-1000 (electrospray ionization); column temperature ° C.

LCMS Method 8:
Instrument: API3000, column: Synergi 2.5 µm MAX-RP, 20×4.0 mm 100 A Mercury; gradient: 0.1% Formic acid in water B: acetonitrile: Time % B 0/10, 0.5/20, 1.5/95, 2.0/95, 2.5/10, 3/10, flow 2.0 mL/min; UV detection array 190-400 (Total Wavelength Chromatogram), Mass detection 100-1000 (electrospray ionization); column temperature 30° C.

LCMS Method 9:
Instrument: API3000, column: Synergi 2.5 µm, 50×4.6 mm, MAX-RP 100 A; gradient: 0.1% formic acid in water B:acetonitrile: Time 0.0/10, 0.2/50, 1.0/95, 1.5/100, 2.5/95, 2.9/50, 3.2/10, 4/10, flow 1.2 mL/min; UV detection array 190-400 (Total Wavelength Chromatogram), Mass detection 100-1000 (electrospray ionization); column temperature 30° C.

LCMS Method 10:
Shimadzu, column: Mercury MS Synergi 2.5 µm, 20×4.0 mm, C12; gradient: A—0.1% formic acid in water/B—acetonitrile: Time/% B: 0.1/5, 0.5/5, 1.0/95, 1.5/95, 2.0/5, 3.0/5, flow 2.0 mL/min; UV detection array 200-400, Mass detection 100-1000 (electrospray ionization); column temperature 40° C.

LCMS Method 11:
Shimadzu, column: Kinetex 5 µm EVO C18 100 A, (100×2.1 mm); gradient: A—0.1% formic acid in water/B—acetonitrile: Time/% B: 0/5, 1/30, 3/95, 4/95, 4.1/5, 6/5, flow 1.4 mL/min; UV detection array 200-400, Mass detection 100-1000 (electrospray ionization); column temperature 40° C.

LCMS Method 12:
Shimadzu, column: Synergi 2.5 µm MAX-RP 100 A, (20×4.0 mm) Mercury; gradient: A—0.1% formic acid in water/B—acetonitrile: Time/% B: 0.1/5, 0.5/5, 1.0/95, 1.5/95, 2.0/5, 3.0/5, flow 2.0 mL/min; UV detection array 200-400, Mass detection 100-1000 (electrospray ionization); column temperature 40° C.

LCMS Method 13:
Acquity, Column: UPLC BEH C18 1.7 µM 2.1×50 mm; Gradient: A—0.1% formic acid in water/B-acetonitrile: 2.2 min run time, 2→98% solvent B:solvent A from 0→1.76 minutes and then 95% solvent B from 1.76 minutes to 2.0 minutes; flow 1.0 mL/min; UV detection array 210-400 nm; Mass Range 100-2050 Da; HRMS_2 min; Column Temperature 50° C.

Preparative HPLC Methods for Purification:
Method 1: HPLC Column: XBRIDGE-C18 (19.0×150 mm, 5 micron), Mobile phase—A: 0.1% TFA in $H_2O$, B: $CH_3CN$, gradient (Time/% B): 0/20, 2/20, 8/50) Flow rate: [19 mL/min].

Method 2: HPLC Column: ZORBAX ECLIPSE XDB C18 (21.2×150 mm, 5 micron), Mobile phase—A: 0.1% TFA in $H_2O$, B: $CH_3CN$, gradient (Time/% B): 0/10, 2/20, 10/40 and Flow rate: [20 mL/min].

Method 3: HPLC Column: XBRIDGE C18 (21.2×150 mm, 5 micron), Mobile phase—A: 10 mM NH$_4$HCO$_3$ in water, B: CH$_3$CN, gradient (Time/% B): 0/10, 2/20, 8/50 and Flow rate: [18 mL/min].

Method 4: HPLC Column: Gemini NX C18 (21.2×150.00 mm, 5 micron); Mobile Phase-(A): 0.1% TFA in water (B): Acetonitrile/Methanol; Flow: 15 ml/min; (Time/% B 0/20, 2/20, 8/20) Method 5: HPLC Column: KINETEX EVO 5µ C18 (21.2×150 mm), Mobile Phase: WATER (A) CH$_3$CN (B), gradient (Time/% B): 0/20, 2/30, 7/70 and Flow rate: [18 mL/min].

Method 6: HPLC Column: KINETEX C18, (21.2×150 mm), Mobile phases: A: WATER, B: CH$_3$CN:MeOH, gradient (Time/% B): 0/20, 2/30, 7/70, Flow rate: 18 mL/min], Method 7: HPLC Column: KINETEX (21.2×150 mm, 5 micron), Mobile phases: A=0.05% TFA in water, B=CH$_3$CN, gradient (Time/% B): 0/20, 2/30, 10/60, Flow rate: 20 mL/min].

Chiral Preparative HPLC Methods for Separation of Isomers:

Method 1: Column: CHIRALPAK IC (10×250 mm, 5 micron), Mobile Phase: Hexane (A) IPA:MeOH, 1:1 (B); Flow rate: 8 mL/min; Isocratic: 96:04(A:B).

Method 2: Column: REGIS WELKO (250×10 mm, 5 micron), Mobile Phase: Hexane (A):EtOH, 1:1 (B); Flow rate: 9 mL/min; Isocratic: 85:15(A:B).

Method 3: Column: CHIRALPAC IG (250×10 mm, 5 micron), Mobile Phase: IPA (A):MeOH, 1:1 (B); Flow rate: 6 mL/min; Isocratic: 98:2(A:B).

Method 4: Column: LUX CELLULOSE-4 (10×250 mm, 5 micron), Mobile Phase: Hexane (A) EtOH:IPA 1:1 (B); Flow rate: 8 mL/min; Isocratic: 90:10(A:B).

Intermediates and General Procedures

Intermediate A: Formation of ethyl 4-acetoxy-3-oxobutanoate

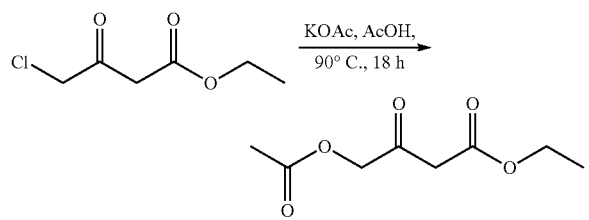

To a solution of ethyl 4-chloro-3-oxobutanoate (200 g, 1215.1 mmol) in acetic acid (1500 mL) was added potassium acetate (357 g, 3645.4 mmol). The resulting solution was stirred at 90° C. for 18 hrs. The solvent was dissolved in water (2 L) and extracted into ethyl acetate (1 L×4 times). The combined organic phases were washed with saturated NaHCO$_3$ solution (2 L) and dried over Na$_2$SO$_4$.

The solvent was removed under reduced pressure and purification of the crude product by silica flash chromatography (0→15%) ethyl acetate in petroleum ether afforded the title compound as a light brown liquid ethyl 4-acetoxy-3-oxobutanoate. (152 g).

$^1$H NMR (400 MHz, CDCl$_3$) δ 4.78 (s, 2H), 4.20 (q, J=14.1, 7.2 Hz, 2H), 3.49 (s, 2H), 2.16 (s, 3H), 1.28 (t, J=7.2 Hz, 3H).

General Procedure I: Formation of 2-methyl-5-oxo-1,4,5,7-tetrahydrofuro[3,4-b]pyridine-3-carboxylate Compounds

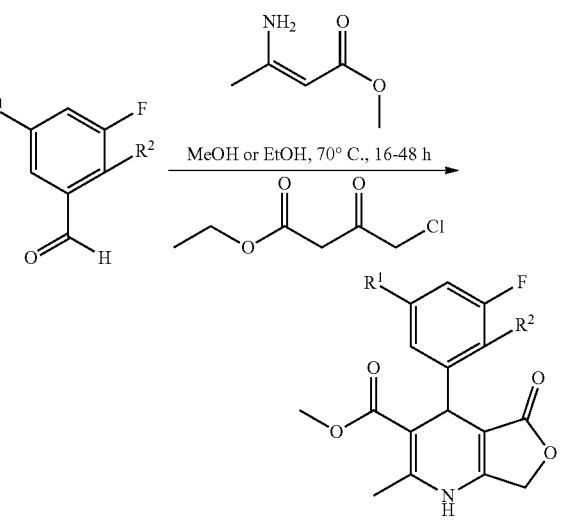

To a solution of aldehyde (1 eq.) and methyl (Z)-3-aminobut-2-enoate (1 eq.) in EtOH or MeOH (0.3M) was added ethyl 4-chloro-3-oxobutanoate (1 eq.). The resulting solution was stirred at 80° C. for 16-48 hours. The solvent was removed under reduced pressure and the crude product purified by silica column chromatography.

General Procedure II: Formation of 2-methyl-5-oxo-1,4,5,7-tetrahydrofuro[3,4-b]pyridine-3-carboxylate Compounds

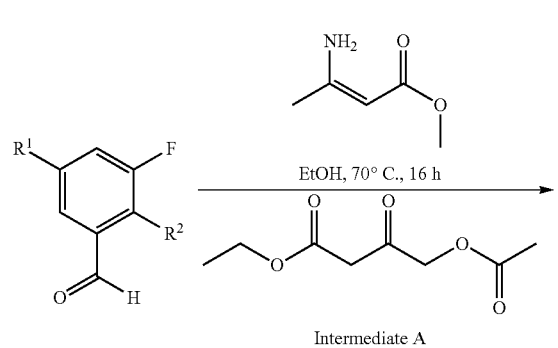

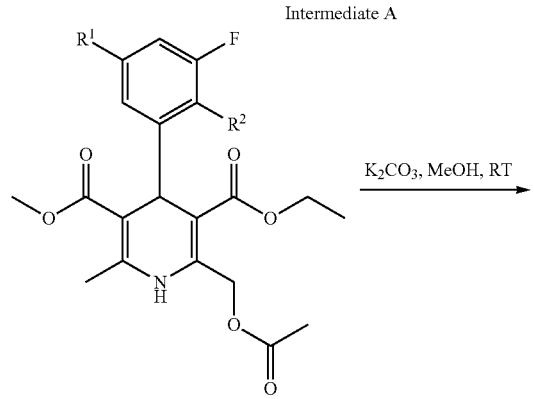

19
-continued

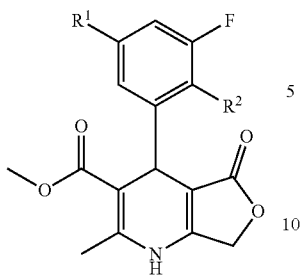

Step 1: To a solution of aldehyde (1 eq.) and methyl (Z)-3-aminobut-2-enoate (1 eq.) in EtOH or MeOH (0.3M) was added ethyl 4-acetoxy-3-oxobutanoate (Intermediate A, 1 eq). The resulting solution was stirred at 80° C. for 14 hrs. The solvent was removed under reduced pressure and afforded the crude compound that was generally taken onto step two without further purification.

Step 2: To a crude intermediate from step 2 in methanol (0.3M) was added potassium carbonate (3 eq). The resulting solution was stirred at room temperature for 2 hrs. The solvent was removed under reduced pressure, added to water (500 mL), extracted into ethyl acetate and dried over $Na_2SO_4$. The solvent was removed under reduced pressure and purification of the crude product by silica flash chromatography afforded the product.

Example 1. Methyl (S)-4-(2-((R or S)-2,2-difluorocyclopropyl)-3-fluorophenyl)-2-methyl-5-oxo-1,4,5,7-tetrahydrofuro[3,4-b]pyridine-3-carboxylate and
Example 2. Methyl (S)-4-(2-((S or R)-2,2-difluorocyclopropyl)-3-fluorophenyl)-2-methyl-5-oxo-1,4,5,7-tetrahydrofuro[3,4-b]pyridine-3-carboxylate

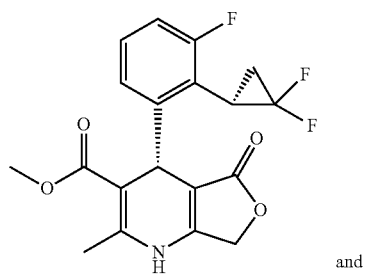

and

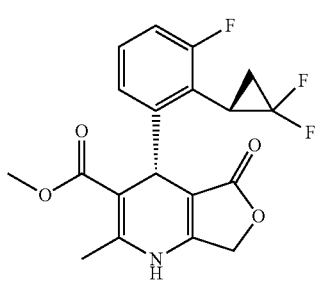

20
Step 1: 2-(2-bromo-3-fluorophenyl)-1,3-dioxolane

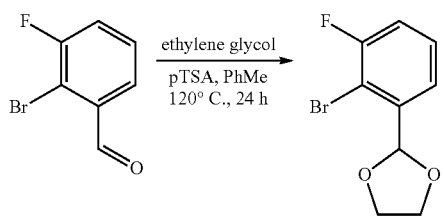 [SMILES: O=Cc1cccc(F)c1Br ; Fc1cccc(C2OCCO2)c1Br]

To a solution of commercially available 2-bromo-3-fluorobenzaldehyde (60 g, 295.56 mmol) and ethylene glycol (65.4 mL, 1182.2 mmol) in toluene (600 mL) was added p-toluenesulfonic acid monohydrate (28.11 g, 147.78 mmol). The resulting solution was stirred at 120° C. for 24 hrs using dean-stark apparatus. The solvent was dissolved in water (2 L) and extracted into ethyl acetate (3 L). This was washed with saturated $NaHCO_3$ solution (1 L) and dried over $Na_2SO_4$. The solvent was removed under reduced pressure and purification of the crude product by silica flash chromatography (0→10%) ethyl acetate in petroleum ether afforded the title compound 2-(2-bromo-3-fluorophenyl)-1.3-dioxolane (60 g) as a colorless liquid.

$^1$H NMR (400 MHz, $CDCl_3$) δ 7.42-7.37 (m, 1H), 7.34-7.29 (m, 1H), 7.16-7.10 (m, 1H), 6.10 (s, 1H), 4.19-4.09 (m, 4H).

Step 2: 2-(3-fluoro-2-vinylphenyl)-1,3-dioxolane

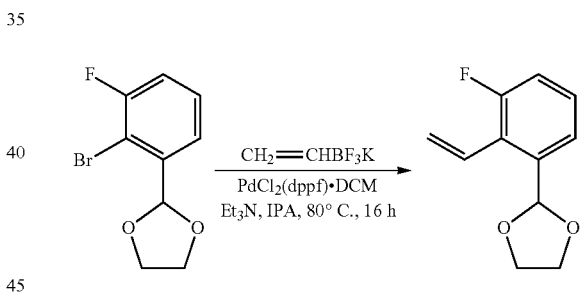

To a solution of 2-(2-bromo-3-fluorophenyl)-1,3-dioxolane (from step 1, 15 g, 60.72 mmol) and potassium vinyltrifluoroborate (16.26 g, 121.45 mmol) in isopropyl alcohol (200 mL) was added triethylamine (25.5 mL, 182.16 mmol) and [1,1'-Bis(diphenylphosphino)ferrocene]dichloropalladium(II). DCM (4.95 g, 6.07 mmol). The resulting solution was degassed with Argon gas for 10 min and stirred at 80° C. for 16 hrs. The reaction mixture was filtered and washed with ethyl acetate (100 mL). The filtrate was added to water (1 L) and extracted into ethyl acetate (2 L) and dried over $Na_2SO_4$. The solvent was removed under reduced pressure and purification of the crude product by silica flash chromatography (0→10%) ethyl acetate in petroleum ether afforded the title compound 2-(3-fluoro-2-vinylphenyl)-1,3-dioxolane (7.5 g) as a colorless liquid.

$^1$H NMR (400 MHz, $CDCl_3$) δ 7.45-7.41 (m, 1H), 7.27-7.20 (m, 1H), 7.10-7.03 (m, 1H), 6.82 (dd, J=17.7, 11.7 Hz, 1H), 5.82-5.78 (m, 1H), 5.66-5.60 (m, 1H), 5.95 (s, 1H), 4.18-4.02 (m, 4H).

Step 3: 2-(2-(2,2-difluorocyclopropyl)-3-fluorophenyl)-1,3-dioxolane

Step 5: 3-ethyl 5-methyl 2-(acetoxymethyl)-4-(2-(2,2-difluorocyclopropyl)-3-fluorophenyl)-6-methyl-1,4-dihydropyridine-3,5-dicarboxylate

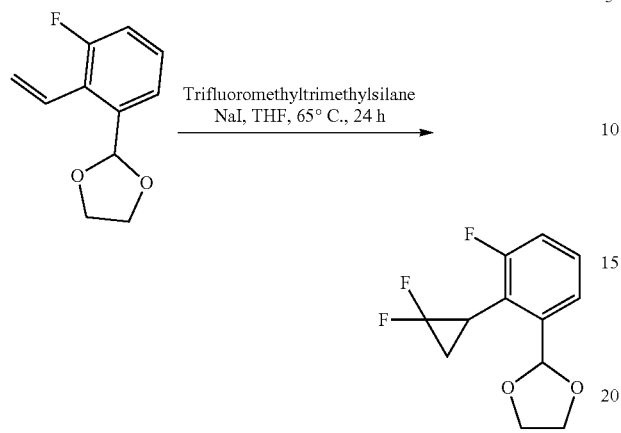

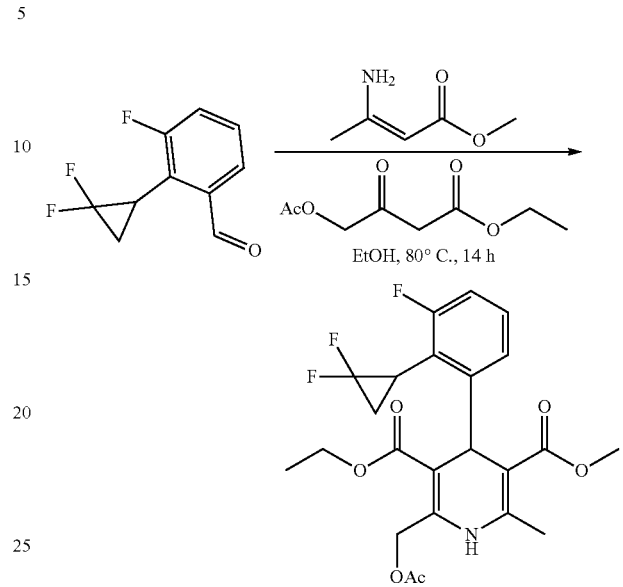

To a solution of 2-(3-fluoro-2-vinylphenyl)-1,3-dioxolane (from step 2, 6.5 g, 33.47 mmol) and trifluoromethyltrimethylsilane (50 mL, 334.7 mmol) in tetrahydrofuran (120 mL) was added sodium iodide (2.5 g, 16.73 mmol). The resulting solution was stirred at 65° C. for 24 hrs. The solvent was evaporated under reduced pressure and the residue was dissolved in DCM (100 mL). This was washed with water (50 mL) and dried over $Na_2SO_4$. The solvent was removed under reduced pressure to afford the title compound 2-(2-(2,2-difluorocyclopropyl)-3-fluorophenyl)-1,3-dioxolane (8 g) as a colorless liquid.

$^1$H NMR (400 MHz, $CDCl_3$) δ 7.42 (d, J=7.5 Hz, 1H), 7.34-7.28 (m, 1H), 7.16-7.03 (m, 1H), 6.06 (s, 1H), 4.20-4.01 (m, 4H), 2.77-2.66 (m, 1H), 2.02-1.72 (m, 2H).

3-ethyl 5-methyl 2-(acetoxymethyl)-4-(2-(2,2-difluorocyclopropyl)-3-fluorophenyl)-6-methyl-1,4-dihydropyridine-3,5-dicarboxylate was synthesized using step 1 of general method II, (using aldehyde from step 4, 3.8 g, 18.93 mmol) to give (9.3 g, crude).

LCMS Rt=1.716 min; MS m/z 468.3 [M+H]+; [Method 7]

Step 6: methyl-4-(2-(2,2-difluorocyclopropyl)-3-fluorophenyl)-2-methyl-5-oxo-1,4,5,7-tetrahydrofuro[3,4-b]pyridine-3-carboxylate Step 4: 2-(2,2-difluorocyclopropyl)-3-fluorobenzaldehyde

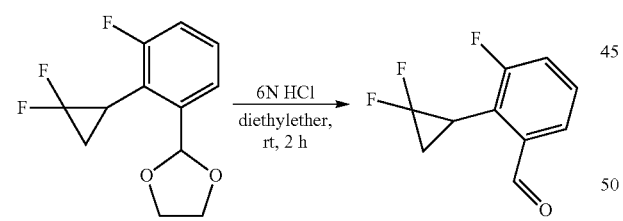

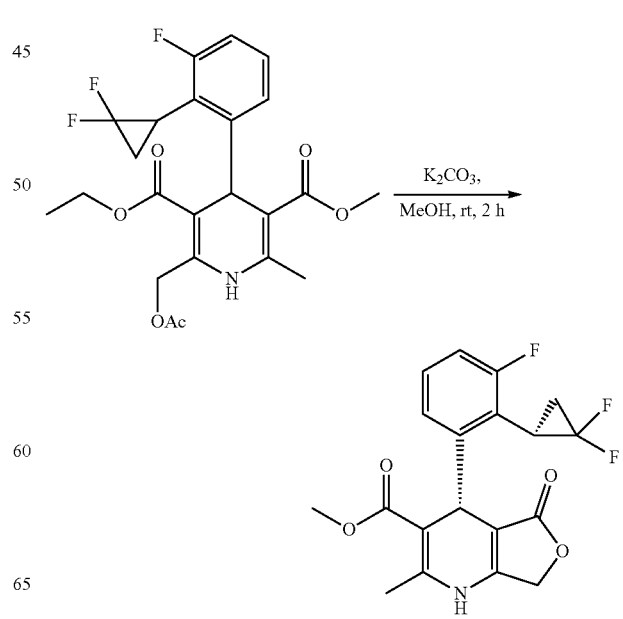

To a solution of 2-(2-(2,2-difluorocyclopropyl)-3-fluorophenyl)-1,3-dioxolane (from step 3, 8 g, 32.76 mmol) in diethyl ether (80 mL) was added 6N HCl (10 mL). The resulting solution was stirred at room temperature for 2 hrs. This was washed with water (50 mL) and saturated $NaHCO_3$ solution (100 mL) and dried over $Na_2SO_4$. The solvent was removed under reduced pressure and purification of the crude product by silica flash chromatography (0→5%) ethyl acetate in petroleum ether afforded the title compound 2-(2,2-difluorocyclopropyl)-3-fluorobenzaldehyde (3.8 g) as a colorless liquid.

$^1$H NMR (400 MHz, $CDCl_3$) δ 10.28 (s, 1H), 7.70 (d, J=6.9 Hz, 1H), 7.50-7.43 (m, 1H), 7.36-7.26 (m, 1H), 2.92-2.81 (m, 1H), 2.16-2.06 (m, 1H), 1.67-1.53 (m, 1H).

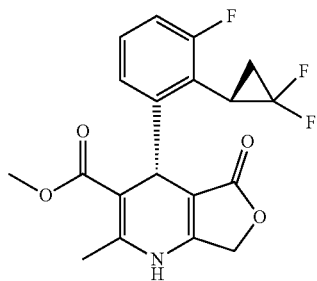

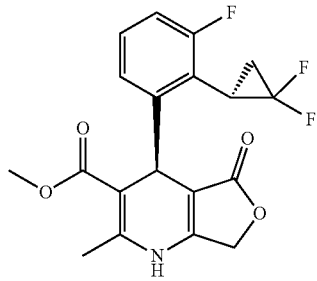

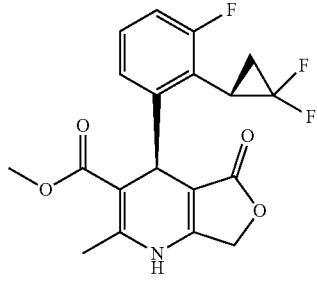

Methyl-4-(2-(2,2-difluorocyclopropyl)-3-fluorophenyl)-2-methyl-5-oxo-1,4,5,7-tetrahydrofuro[3,4-b]pyridine-3-carboxylate was synthesized using step 2 of general method II (using intermediate from step 5, 9.3 g, 19.89 mmol). Crude product was purified by silica flash chromatography (0→50%) ethyl acetate in petroleum ether afforded the title compound methyl4-(2-(2,2-difluorocyclopropyl)-3-fluorophenyl)-2-methyl-5-oxo-1,4,5,7-tetrahydrofuro[3,4-b]pyridine-3-carboxylate (2.3 g) as an off white solid.

LCMS Rt=1.489 min; MS m/z 380.1 [M+H]+; [Method 7]

The racemic sample was separated into its four stereoisomers by chiral SFC (Mobile Phase: 30% IPA/CO$_2$, 80 g/min; Column: (SS) Whelk-O1 21×250 mm; Instrument: Thar80_SN4739).

Example 1

290.6 mg of second eluting stereoisomer as a white solid (73.6%)

SFC Rt=2.94 min; ((SS) Whelk-O1 4.6×100 mm, 5 μm, 5→55% IPA/CO$_2$).

LCMS Rt=2.12 min; MS m/z 380.3 [M+H]+; [Method 4]

$^1$H NMR (400 MHz, DMSO-d6) δ 9.89 (s, 1H), 7.29 (td, J=7.9, 5.6 Hz, 1H), 7.11-6.91 (m, 2H), 5.20 (s, 1H), 4.88 (q, J=16.3 Hz, 2H), 3.49 (s, 3H), 2.85 (td, J=12.5, 8.5 Hz, 1H), 2.60 (dtd, J=11.9, 7.9, 3.5 Hz, 1H), 2.27 (s, 3H), 2.16 (tq, J=12.9, 7.3, 6.7 Hz, 1H).

Example 2

261.0 mg of first eluting stereoisomer as a white solid (68.9%)

SFC Rt=2.86 min; ((SS) Whelk-O1 4.6×100 mm, 5 μm, 5→55% IPA/CO$_2$).

LCMS Rt=2.08 min; MS m/z 380.2 [M+H]+; [Method 4]

$^1$H NMR (400 MHz, DMSO-d6) δ 9.86 (s, 1H), 7.31 (td, J=8.0, 5.7 Hz, 1H), 7.05-6.97 (m, 2H), 5.23 (s, 1H), 4.78 (s, 2H), 3.43 (s, 3H), 3.15 (td, J=12.6, 8.5 Hz, 1H), 2.36 (s, 3H), 2.23 (tt, J=12.3, 6.7 Hz, 1H), 1.93 (dtd, J=11.0, 8.4, 7.7, 4.7 Hz, 1H).

Example 1b 275.0 mg of third eluting stereoisomer as a white solid (72.2%)

SFC Rt=3.16 min; ((SS) Whelk-O1 4.6×100 mm, 5 μm, 5→55% IPA/CO$_2$).

LCMS Rt=2.08 min; MS m/z 380.1 [M+H]+; [Method 4]

$^1$H NMR (400 MHz, DMSO-d6) δ 9.89 (s, 1H), 7.31 (td, J=7.9, 5.6 Hz, 1H), 7.01 (dd, J=9.7, 8.2 Hz, 2H), 5.23 (s, 1H), 4.77 (s, 2H), 3.43 (s, 3H), 3.15 (td, J=12.7, 8.7 Hz, 1H), 2.36 (s, 3H), 2.30-2.15 (m, 1H), 1.94 (dtd, J=14.1, 8.0, 3.3 Hz, 1H).

Example 2b 366.0 mg of fourth eluting stereoisomer as a white solid (93.0%).

SFC Rt=3.39 min; ((SS) Whelk-O1 4.6×100 mm, 5 μm, 5→55% IPA/CO$_2$).

LCMS Rt=2.07 min; MS m/z 380.1 [M+H]+; [Method 4]

$^1$H NMR (400 MHz, DMSO-d6) δ 10.01 (s, 1H), 7.29 (td, J=7.9, 5.6 Hz, 1H), 7.10-6.92 (m, 2H), 5.19 (s, 1H), 4.87 (q, J=16.2 Hz, 2H), 3.48 (s, 3H), 2.85 (td, J=12.5, 8.5 Hz, 1H), 2.61 (dtd, J=11.8, 8.0, 3.4 Hz, 1H), 2.27 (s, 3H), 2.15 (tt, J=12.1, 7.0 Hz, 1H).

Example 3. Methyl (S)-4-(2-cyclobutyl-3-fluorophenyl)-2-methyl-5-oxo-1,4,5,7-tetrahydrofuro [3,4-b]pyridine-3-carboxylate

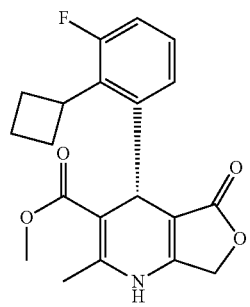 [SMILES: COC(=O)C1=C(C)NC2=C(C(=O)OC2)[C@H]1c1cccc(F)c1C1CCC1]

Step 1: 2-fluoro-6-formylphenyl trifluoromethanesulfonate

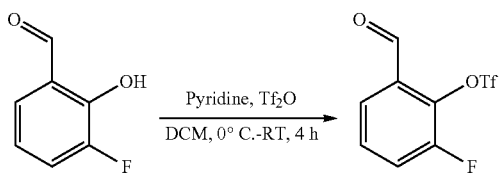 [SMILES: O=Cc1cccc(F)c1O ; O=Cc1cccc(F)c1OS(=O)(=O)C(F)(F)F]

To a solution of 3-fluoro-2-hydroxybenzaldehyde (6 g, 42.82 mmol) and pyridine (10.35 mL, 128.47 mmol) in dichloromethane (35 mL) at 0° C. was added triflic anhydride (8.45 mL, 51.38 mmol). The resulting solution was stirred at room temperature for 4 hrs. The reaction mixture was added to water (1 L) and extracted into ethyl acetate (1 L), EtOAc was washed with saturated NH₄Cl solution (50 mL) and dried over Na₂SO₄. The solvent was removed under reduced pressure and purification of the crude product by silica flash chromatography (0→20%) ethyl acetate in petroleum ether afforded the title compound 2-fluoro-6-formylphenyl trifluoromethanesulfonate (6 g) as a colorless liquid.

¹H NMR (300 MHz, CDCl₃) δ 10.22 (s, 1H), 7.80-7.76 (m, 1H), 7.58-7.53 (m, 2H).

Step 2: 2-cyclobutyl-3-fluorobenzaldehyde

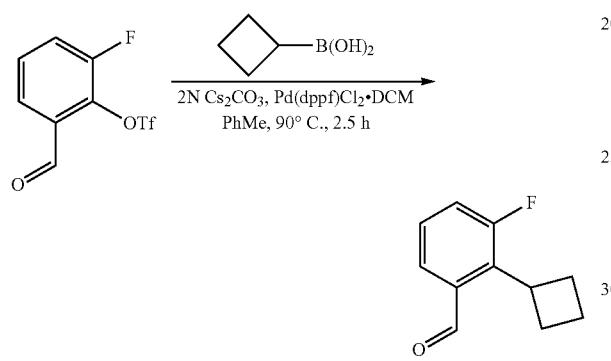

To a solution of 2-fluoro-6-formylphenyl trifluoromethanesulfonate (from step 1, 3 g, 11.03 mmol) and 2N cesium carbonate (8.82 mL, 17.64 mmol) in toluene (35 mL) was added cyclobutylboronic acid (1.32 g, 13.24 mmol) and [1,1'-Bis(diphenylphosphino)ferrocene]dichloropalladium (II).DCM (900 mg, 1.103 mmol). The resulting solution was degassed with Argon gas for 10 min and stirred at 90° C. for 2.5 hrs. The reaction mixture was filtered and washed with ethyl acetate (100 mL). The filtrate was dissolved in water (1 L), extracted into ethyl acetate (2 L) and dried over Na₂SO₄. The solvent was removed under reduced pressure and purification of the crude product by silica flash chromatography (0→5%) ethyl acetate in petroleum ether afforded the title compound 2-cyclobutyl-3-fluorobenzaldehyde (200 mg) as a colorless liquid.

¹H NMR (600 MHz, CDCl₃) δ 10.26 (s, 1H), 7.57 (d, J=7.8 Hz, 1H), 7.26-7.17 (m, 2H), 4.27-4.22 (m, 1H), 2.46-2.42 (m, 4H), 2.14-2.05 (m, 1H), 1.93-1.90 (m, 1H).

Step 3: 3-ethyl-5-methyl-2-(acetoxymethyl)-4-(2-cyclobutyl-3-fluorophenyl)-6-methyl-1,4-dihydro pyridine-3,5-dicarboxylate

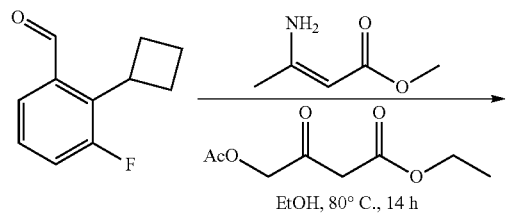

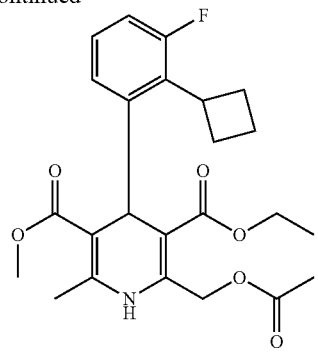

3-ethyl-5-methyl-2-(acetoxymethyl)-4-(2-cyclobutyl-3-fluorophenyl)-6-methyl-1,4-dihydro pyridine-3,5-dicarboxylate was synthesized using step 1 of general method II (using the aldehyde from step 2, 200 mg, 1.12 mmol) to give (80 mg, crude).

LCMS Rt=1.94 min; MS m/z 446.4 [M+H]+; [Method 8]

Step 4: methyl-4-(2-cyclobutyl-3-fluorophenyl)-2-methyl-5-oxo-1,4,5,7-tetrahydrofuro[3,4-b]pyridine-3-carboxylate

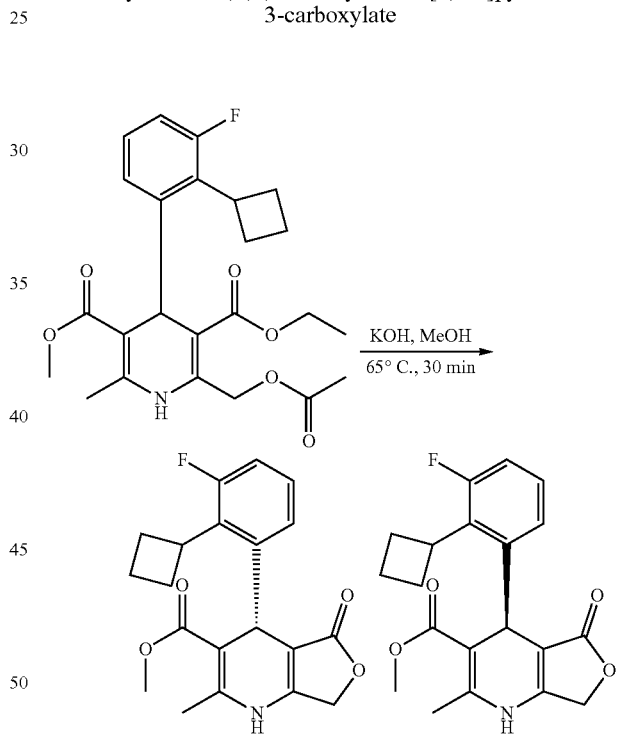

To a stirred solution of 3-ethyl 5-methyl 2-(acetoxymethyl)-4-(2-cyclobutyl-3-fluorophenyl)-6-methyl-1,4-dihydropyridine-3,5-dicarboxylate (using intermediate from step 3, 80 mg, 19.89 mmol) in methanol (5 mL) was added potassium hydroxide (1.2 g, 21.57 mmol). The resulting solution was stirred at 65° C. for 30 min. Water was added to reaction mixture and solid precipitated out and was filtered. The solid was washed with diethyl ether and the solid was collected and dried under reduced pressure afforded the title crude compound. Crude product was purified using preparative HPLC [Method 5] which afforded the title compound methyl-4-(2-cyclobutyl-3-fluorophenyl)-2-methyl-5-oxo-1,4,5,7-tetrahydrofuro[3,4-b]pyridine-3-carboxylate (34 mg) as an off white solid.

LCMS Rt=1.598 min; MS m/z 358.2 [M+H]+; [Method 7]

Racemic mixture was separated into two enantiomers using preparative chiral HPLC [Method 1]

Example 3 mg of second eluting enantiomer as a white solid, 29% yield.

Chiral HPLC Rt=6.306 min (Mobile Phase: n-Hexane (A) IPA:MeOH, 1:1 (B); 1 mL/min; Isocratic: 70:30 (A:B); Column: Lux, 5 micron, Cellulose-4 (250×4.6 mm, 5 micron).

LCMS Rt=1.6 min; MS m/z 358.2 [M+H]+; [Method 7]
$^1$H NMR (400 MHz, MeOH-d4) δ 7.01-7.04 (m, 1H), 6.94 (d, J=11.2 Hz, 1H), 6.84-6.79 (m, 1H), 5.18 (s, 1H), 4.76 (s, 2H), 4.32-4.23 (m, 1H), 3.46 (s, 3H), 2.74-2.50 (m, 2H), 2.49-2.29 (m, 2H), 2.35 (s, 3H), 2.18-1.90 (m, 2H).

Example 3b 10 mg of first eluting enantiomer as a white solid, 29% yield.

Chiral HPLC Rt=5.796 min (Mobile Phase: n-Hexane (A) IPA:MeOH, 1:1 (B); 1 mL/min; Isocratic: 70:30 (A:B); Column: Lux, 5 micron, Cellulose-4 (250×4.6 mm, 5 micron).

LCMS Rt=1.602 min; MS m/z 358.2 [M+H]+; [Method 7]$^1$H NMR (400 MHz, MeOH-d4) δ 7.01-7.04 (m, 1H), 6.94 (d, J=11.2 Hz, 1H), 6.84-6.79 (m, 1H), 5.18 (s, 1H), 4.76 (s, 2H), 4.32-4.23 (m, 1H), 3.46 (s, 3H), 2.74-2.50 (m, 2H), 2.49-2.29 (m, 2H), 2.35 (s, 3H), 2.18-1.90 (m, 2H).

Example 4. Methyl (S)-4-(2-cyclopropyl-3-fluorophenyl)-2-methyl-5-oxo-1,4,5,7-tetrahydrofuro[3,4-b]pyridine-3-carboxylate

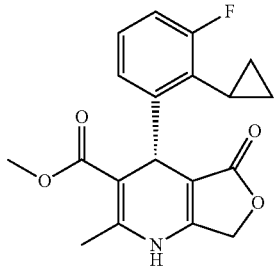 [SMILES: COC(=O)C1=C(C)NC2=C(C(=O)OC2)[C@H]1c1cccc(F)c1C1CC1]

Step 1: 2-cyclopropyl-3-fluorobenzaldehyde

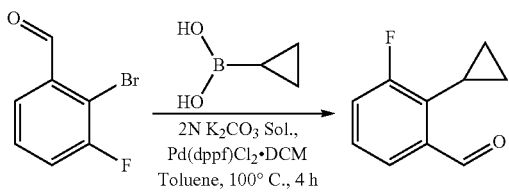

To a solution of commercially available 2-bromo-3-fluorobenzaldehyde (15 g, 73.88 mmol) and cyclopropylboronic acid (7.61 g, 88.66 mmol) in toluene (160 mL) was added 2N $K_2CO_3$ (25.5 mL, 182.16 mmol) and [1,1'-bis(diphenylphosphino)ferrocene]dichloropalladium(II). DCM (6.03 g, 7.38 mmol). The resulting solution was degassed with Argon gas for 10 min and stirred at 100° C. for 4 hrs. The reaction mixture was filtered and washed with ethyl acetate (200 mL). The filtrate was added to water (500 mL), product extracted into ethyl acetate (2 L) and dried over $Na_2SO_4$. The solvent was removed under reduced pressure and purification of the crude product by silica flash chromatography (0-1%) ethyl acetate in petroleum ether afforded the title compound 2-cyclopropyl-3-fluorobenzaldehyde (11.2 g) as a colorless liquid.

$^1$H NMR (300 MHz, CDCl$_3$) δ 10.70 (s, 1H), 7.63 (dd, J=1.2, 7.8 Hz, 1H), 7.35-7.15 (m, 2H), 2.14-2.02 (m, 1H), 1.19-1.09 (m, 2H), 0.85-0.75 (m, 2H).

Step 2: methyl 4-(2-cyclopropyl-3-fluorophenyl)-2-methyl-5-oxo-1,4,5,7-tetrahydrofuro[3,4-b]pyridine-3-carboxylate

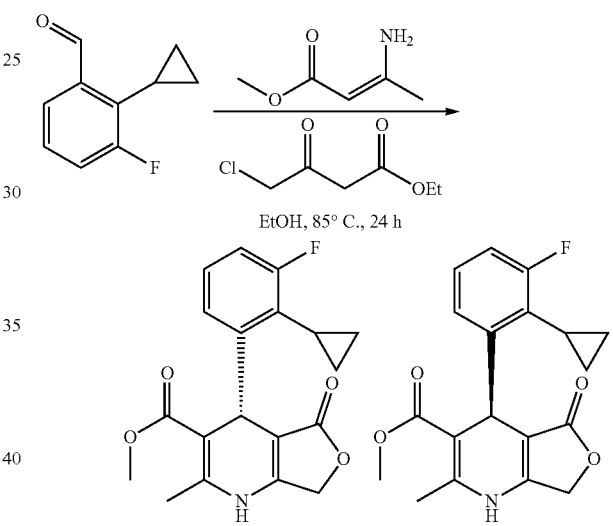

Methyl 4-(2-cyclopropyl-3-fluorophenyl)-2-methyl-5-oxo-1,4,5,7-tetrahydrofuro [3,4-b]pyridine-3-carboxylate was synthesized using general method I (using the intermediate from step 1, 24.5 g, 149.2 mmol). Crude product was purified using silica column chromatography afforded the title compound methyl 4-(2-cyclopropyl-3-fluorophenyl)-2-methyl-5-oxo-1,4,5,7-tetrahydrofuro [3,4-b]pyridine-3-carboxylate (5.15 g) as an off white solid. LCMS Rt=1.598 min; MS m/z 358.2 [M+H]+; [Method 7]

The racemic sample was separated into its enantiomers by chiral SFC (Mobile Phase: 10% MeOH/CO$_2$, 70 mL/min; Column: OJ-H 2×25 cm).

Example 4

2.27 g of the second eluting enantiomer as an off-white solid (84%).

SFC Rt=2.02 min (Chiralcel OJ-H 4.6×100 mm, 5 μm, 5→55% MeOH/CO$_2$).

HRMS Rt=1.16 min; MS m/z 344.1334 [M+H]+; [Method 13]

$^1$H NMR (400 MHz, Methanol-d4) δ 7.11 (td, J=7.9, 5.2 Hz, 1H), 6.98 (dd, J=7.8, 1.4 Hz, 1H), 6.85-6.69 (m, 1H), 5.57 (s, 1H), 4.75 (s, 2H), 3.52 (s, 3H), 2.34 (s, 3H), 2.13 (tt, J=8.7, 5.8 Hz, 1H), 1.26-1.14 (m, 1H), 1.04-0.87 (m, 2H), 0.87-0.69 (m, 1H).

Example 4b 2.38 g of first eluting enantiomer as an off-white solid (79%).

SFC Rt=1.96 min (Chiralcel OJ-H 4.6×100 mm, 5 μm, 5→55% MeOH/CO$_2$).

HRMS Rt=1.16; MS m/z 344.1329 [M+H]+; [Method 13]

$^1$H NMR (400 MHz, Methanol-d4) δ 7.11 (td, J=8.0, 5.3 Hz, 1H), 6.98 (dd, J=7.8, 1.4 Hz, 1H), 6.78 (ddd, J=11.3, 8.3, 1.8 Hz, 1H), 5.57 (s, 1H), 4.78 (s, 2H), 3.52 (s, 3H), 2.34 (s, 3H), 2.14 (tt, J=8.8, 5.8 Hz, 1H), 1.27-1.17 (m, 1H), 1.01-0.90 (m, 2H), 0.82-0.73 (m, 1H).

Example 5. Methyl (S)-4-(2-((R or S)-2,2-difluorocyclopropyl)-3,5-difluorophenyl)-2-methyl-5-oxo-1,4,5,7-tetrahydrofuro[3,4-b]pyridine-3-carboxylate and Example 6. Methyl (S)-4-(2-((R or S)-2,2-difluorocyclopropyl)-3,5-difluorophenyl)-2-methyl-5-oxo-1,4,5,7-tetrahydrofuro[3,4-b]pyridine-3-carboxylate

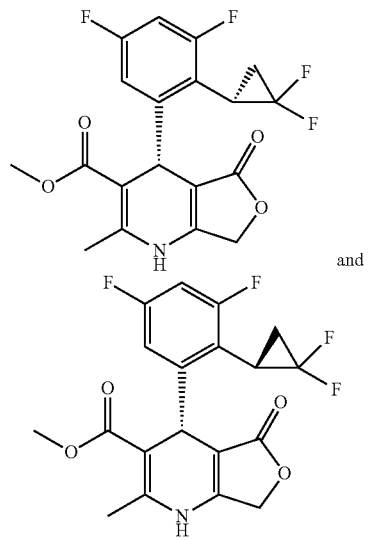

and

Step 1: 2-(2-bromo-3,5-difluorophenyl)-1,3-dioxolane

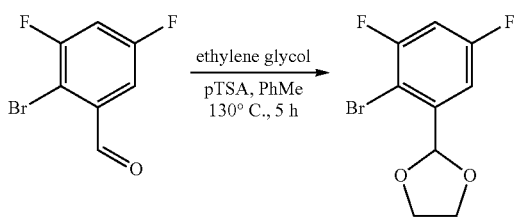 [SMILES: O=Cc1cc(F)cc(F)c1Br ; Fc1cc(F)c(Br)c(C2OCCO2)c1]

A solution of 2-bromo-3,5-difluorobenzaldehyde (10 g, 45.24 mmol) and ethylene glycol (8.45 g, 135.7 mmol) (600 mL), p-toluenesulfonic acid monohydrate (6.88 g, 36.18 mmol) in toluene (100 mL) was stirred at 130° C. for 5 hrs using dean-stark apparatus. The solvent was added in saturated NaHCO$_3$ solution (100 mL) organic layer was separated, aqueous layer was extracted with EtOAc twice, and the combined organic layers were washed with brine and dried over Na$_2$SO$_4$. The solvent was removed under reduced pressure and purification of the crude product by silica flash chromatography (0→10%) ethyl acetate in hexane afforded the title compound 2-(2-bromo-3,5-difluorophenyl)-1,3-dioxolane (11.5 g) as a colorless liquid.

$^1$H NMR (300 MHz, CDCl$_3$) δ 7.201-7.157 (m, 1H), 6.49-6.87 (m, 1H), 6.08 (s, 1H), 4.17-4.04 (m, 4H).

Step 2: 2-(3,5-difluoro-2-vinylphenyl)-1,3-dioxolane

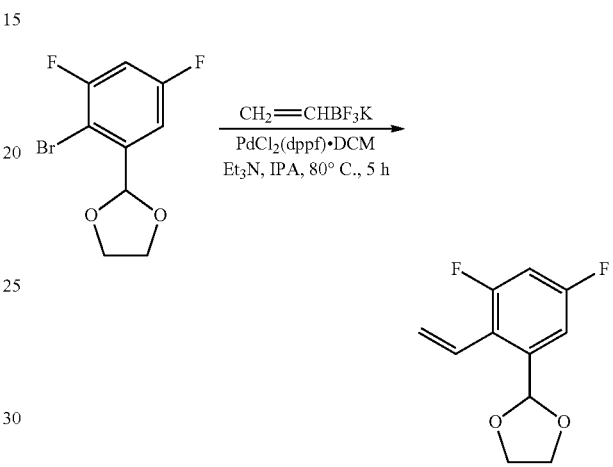

A solution of 2-(2-bromo-3,5-difluorophenyl)-1,3-dioxolane (from step 1, 5 g, 18.94 mmol) and potassium vinyltrifluoroborate (5.8 g, 37.89 mmol), triethylamine (7.91 mL, 56.82 mmol) in isopropyl alcohol (50 mL) was degassed for 10 min using Argon gas. [1,1'-Bis (diphenylphosphino)ferrocene]dichloropalladium(II). DCM (1.55 g, 1.89 mmol) was added and the resulting solution was degassed again with Argon gas for 10 min and stirred at 80° C. for 5 hrs. The reaction mixture was filtered and washed with ethyl acetate (100 mL). The filtrate was added to water (1 L) and extracted into ethyl acetate (2 L) and dried over Na$_2$SO$_4$. The solvent was removed under reduced pressure and purification of the crude product by silica flash chromatography (0→10%) ethyl acetate in petroleum ether afforded the title compound 2-(3,5-difluoro-2-vinylphenyl)-1,3-dioxolane 3.45 g) as a colorless liquid.

$^1$H NMR (300 MHz, CDCl$_3$) δ 7.20-7.16 (m, 1H), 6.94-6.83 (m, 1H), 6.82 (dd, J=17.7, 11.7 Hz, 1H), 5.60 (dd, J=1.2, 11.7 Hz, 1H), 5.66-5.60 (m, 1H), 5.95 (s, 1H), 4.18-4.02 (m, 4H).

Step 3: 2-(2-(2,2-difluorocyclopropyl)-3,5-difluorophenyl)-1,3-dioxolane

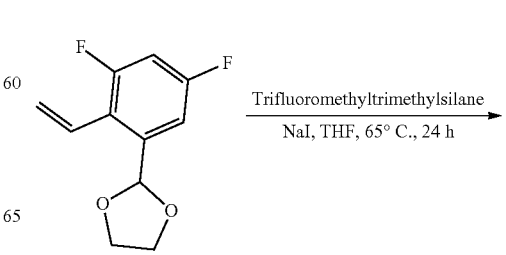

-continued

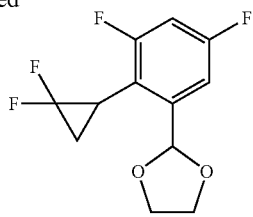

To a solution of 2-(3,5-difluoro-2-vinylphenyl)-1,3-dioxolane (from step 2, 2.4 g, 11.31 mmol) and trifluoromethyltrimethylsilane (16.1 g, 113.1 mmol) in tetrahydrofuran (15 mL) was added sodium iodide (850 mg, 5.65 mmol). The resulting solution was stirred at 65° C. for 24 hrs. Cooled to room temperature again, trifluoromethyltrimethylsilane (16.1 g, 113.1 mmol) and sodium iodide (850 mg, 5.65 mmol) was added to reaction and the resulting solution was stirred at 65° C. for 24 hrs. The reaction mixture was partition between EtOAc and water, organic layer was washed with brine, dried over Na$_2$SO$_4$. The solvent was removed under reduced pressure to afforded the title compound 2-(2-(2,2-difluorocyclopropyl)-3,5-difluorophenyl)-1,3-dioxolane (1.5 g) as a brown liquid.

$^1$H NMR (400 MHz, CDCl$_3$) δ 7.26-7.14 (m, 1H), 6.90-6.77 (m, 1H), 6.04 (s, 1H), 4.17-4.03 (m, 4H), 2.77-2.66 (m, 1H), 1.98-1.70 (m, 2H).

Step 4: 2-(2,2-difluorocyclopropyl)-3,5-difluorobenzaldehyde

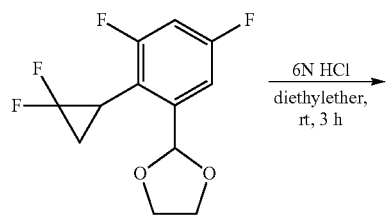

To a solution of 2-(2-(2,2-difluorocyclopropyl)-3,5-difluorophenyl)-1,3-dioxolane (from step 3, 1.5 g, 5.72 mmol) in diethyl ether (15 mL) was added 6N HCl (3 mL). The resulting solution was stirred at room temperature for 3 hrs. This was washed with water (50 mL) and saturated NaHCO$_3$ solution (100 mL) and dried over Na$_2$SO$_4$. The solvent was removed under reduced pressure and purification of the crude product by silica flash chromatography (0→5%) ethyl acetate in hexane afforded the title compound 2-(2,2-difluorocyclopropyl)-3,5-difluorobenzaldehyde (1.25 g) as a colorless liquid.

$^1$H NMR (300 MHz, CDCl$_3$) δ 10.22 (s, 1H), 7.50-7.39 (m, 1H), 7.20-7.05 (m, 1H), 2.80-2.60 (m, 1H), 2.18-1.89 (m, 1H), 1.65-1.53 (m, 1H).

Step 5: 3-ethyl 5-methyl 2-(acetoxymethyl)-4-(2-(2,2-difluorocyclopropyl)-3,5-difluorophenyl)-6-methyl-1,4-dihydropyridine-3,5-dicarboxylate

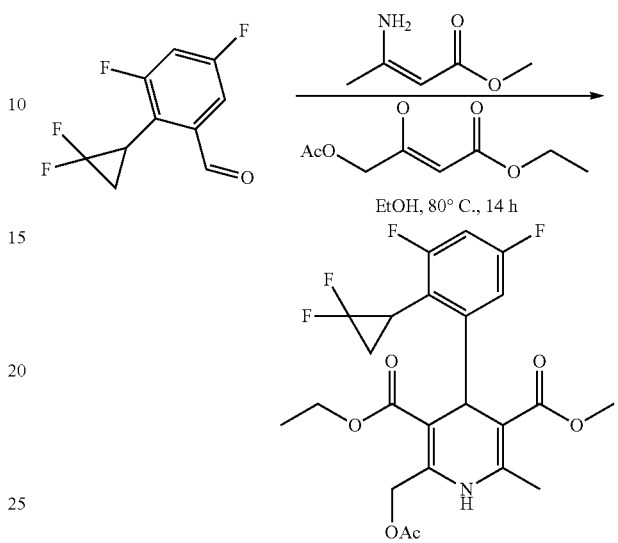

3-ethyl 5-methyl 2-(acetoxymethyl)-4-(2-(2,2-difluorocyclopropyl)-3,5-difluorophenyl)-6-methyl-1,4-dihydropyridine-3,5-dicarboxylate was synthesized using step 1 of general method II (using the aldehyde from step 4, 1.25 g, 5.73 mmol) to give (1.45 g, crude).

LCMS Rt=1.775 min; MS m/z 486.3 [M+H]+; [Method 12]

Step 6: methyl 4-(2-(2,2-difluorocyclopropyl)-3,5-difluorophenyl)-2-methyl-5-oxo-1,4,5,7-tetrahydrofuro[3,4-b]pyridine-3-carboxylate

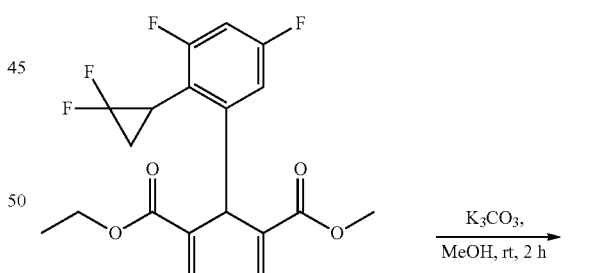

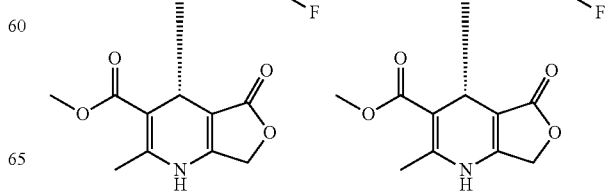

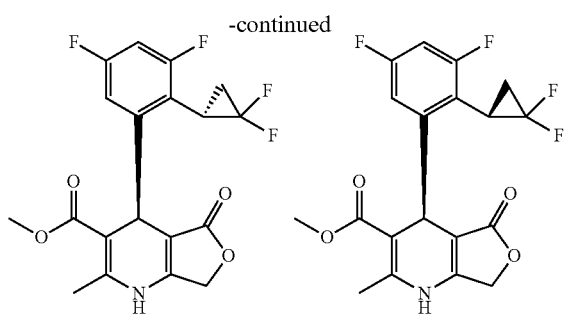

Methyl 4-(2-(2,2-difluorocyclopropyl)-3,5-difluorophenyl)-2-methyl-5-oxo-1,4,5,7-tetrahydrofuro[3,4-b]pyridine-3-carboxylate was synthesized using step 2 of general method II (using the intermediate from step 5, 945 mg, 1.948 mmol). Crude product by silica flash chromatography (0→50%) ethyl acetate in petroleum ether afforded the title compound methyl 4-(2-(2,2-difluorocyclopropyl)-3,5-difluorophenyl)-2-methyl-5-oxo-1,4,5,7-tetrahydrofuro[3,4-b]pyridine-3-carboxylate (520 mg) as an off white solid.

LCMS Rt=1.553 min; MS m/z 398.2 [M+H]+; [Method 12]

$^1$H NMR (300 MHz, CD$_3$CN) δ 7.80 (s, 1H), 6.949-6.774 (m, 2H), 5.31 (s, 1H), 4.81, 4.79 and 4.70 (3 s, 2H), 3.54 and 3.49 (2 s, 3H), 2.79-2.66 (m, 1H), 2.39 and 2.30 (2 s, 3H), 2.14-2.05 (m, 2H), (multiple peaks due to diastereomeric mixture).

The racemic sample was separated into its four stereoisomers by chiral SFC (Mobile Phase: 25% IPA/CO$_2$, 80 g/min; Column: (SS) Whelk-O1 21×250 mm; Instrument: Thar80_SN4740).

Example 5

120.2 mg of second eluting stereoisomer as a white solid (93.0%)

SFC Rt=2.70 min ((SS) Whelk-O1 4.6×100 mm, 5 μm, 5→55% IPA/CO$_2$).

LCMS Rt=2.19 min; MS m/z 398.2 [M+H]+; [Method 4]

$^1$H NMR (400 MHz, DMSO-d6) δ 9.94 (s, 1H), 7.07 (ddd, J=11.1, 8.8, 2.8 Hz, 1H), 6.96-6.68 (m, 1H), 5.23 (d, J=1.8 Hz, 1H), 5.08-4.63 (m, 2H), 3.50 (s, 3H), 2.81 (td, J=11.9, 7.8 Hz, 1H), 2.59 (ddt, J=12.7, 8.3, 4.0 Hz, 1H), 2.29 (s, 3H), 2.18 (tt, J=12.7, 7.0 Hz, 1H).

Example 6

61.8 mg of first eluting stereoisomer as a white solid (47.8%)

SFC Rt=2.64 min ((SS) Whelk-O1 4.6×100 mm, 5 μm, 5→55% IPA/CO$_2$).

LCMS Rt=2.20 min; MS m/z 398.3 [M+H]+; [Method 4]

$^1$H NMR (400 MHz, DMSO-d6) δ 9.92 (s, 1H), 7.07 (ddd, J=11.2, 8.8, 2.7 Hz, 1H), 6.89-6.66 (m, 1H), 5.25 (d, J=1.8 Hz, 1H), 4.86-4.72 (m, 2H), 3.45 (s, 3H), 3.15-3.03 (m, 1H), 2.38 (s, 3H), 2.26 (tq, J=12.2, 7.1, 6.3 Hz, 1H), 1.92 (qd, J=8.8, 8.2, 4.9 Hz, 1H).

Example 5b 76.7 mg of third eluting stereoisomer as a white solid (59.4%)

SFC Rt=2.86 min ((SS) Whelk-O1 4.6×100 mm, 5 μm, 5→55% IPA/CO$_2$).

LCMS Rt=2.19 min; MS m/z 398.1 [M+H]+; [Method 4]

$^1$H NMR (400 MHz, DMSO-d6) δ 9.92 (s, 1H), 7.07 (ddd, J=10.1, 8.6, 2.7 Hz, 1H), 6.92-6.64 (m, 1H), 5.25 (d, J=1.5 Hz, 1H), 4.80 (d, J=3.5 Hz, 1H), 3.45 (s, 3H), 3.16-3.01 (m, 1H), 2.38 (s, 3H), 2.25 (tt, J=12.2, 6.6 Hz, 1H), 1.92 (qd, J=9.1, 8.0, 5.0 Hz, 1H).

Example 6b 133.6 mg of fourth eluting stereoisomer as a white solid (98.0%)

SFC Rt=3.08 min ((SS) Whelk-O1 4.6×100 mm, 5 μm, 5→55% IPA/CO$_2$).

LCMS Rt=2.19 min; MS m/z 398.2 [M+H]+; [Method 4]

$^1$H NMR (400 MHz, DMSO-d6) δ 9.92 (s, 1H), 7.07 (ddd, J=11.2, 8.8, 2.7 Hz, 1H), 6.89-6.66 (m, 1H), 5.25 (d, J=1.8 Hz, 1H), 4.86-4.72 (m, 2H), 3.45 (s, 3H), 3.15-3.03 (m, 1H), 2.38 (s, 3H), 2.26 (tq, J=12.2, 7.1, 6.3 Hz, 1H), 1.92 (qd, J=8.8, 8.2, 4.9 Hz, 1H).

Example 7. Methyl (S)-4-(3,5-difluoro-2-((S or R)-1-fluoroethyl)phenyl)-2-methyl-5-oxo-1,4,5,7-tetrahydrofuro[3,4-b]pyridine-3-carboxylate

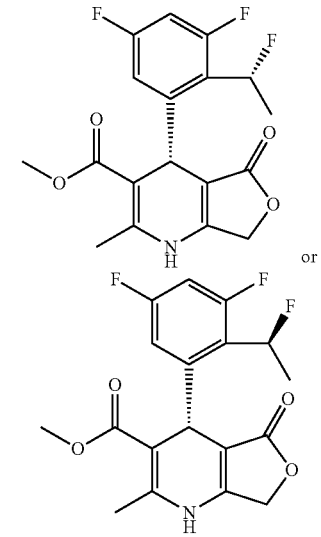

Step 1:
2-(1,3-dioxolan-2-yl)-4,6-difluorobenzaldehyde

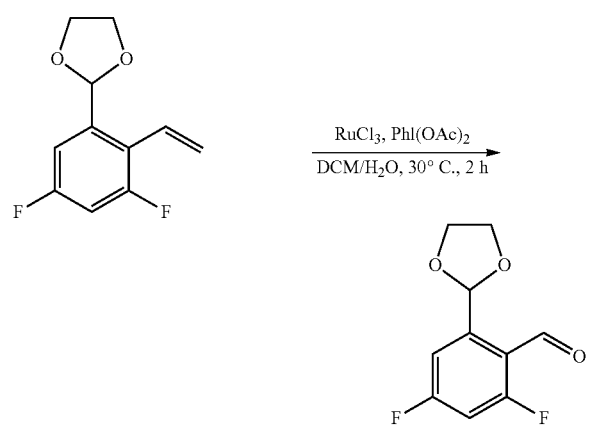

To a solution of 2-(3,5-difluoro-2-vinylphenyl)-1,3-dioxolane (step 2 from example 5, 5 g, 23.58 mmol) and ruthenium chloride.XH$_2$O (490 mg, 2.35 mmol) in dichloromethane (50 mL) and water (10 mL) was added diacetoxy iodobenzene (11.4 g, 35.37 mmol). The resulting solution was stirred at 30° C. for 2 hrs. The reaction mixture was filtered and washed with ethyl acetate (200 mL). The filtrate was added to water (200 mL), extracted into ethyl acetate (500 mL) and dried over Na$_2$SO$_4$. The solvent was removed under reduced pressure and purification of the crude product by silica flash chromatography (0→10%) ethyl acetate in petroleum ether afforded the title compound 2-(1,3-dioxolan-2-yl)-4,6-difluorobenzaldehyde (3 g) as a colorless liquid.

$^1$H NMR (300 MHz, CDCl$_3$) δ 10.41 (s, 1H), 7.35 (d, J=9.6 Hz, 1H), 6.95-6.85 (m, 1H), 6.53 (s, 1H), 4.08 (s, 4H).

Step 2: 1-(2-(1,3-dioxolan-2-yl)-4,6-difluorophenyl)ethan-1-ol

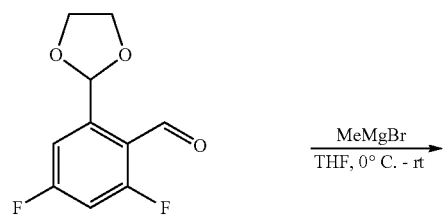

To a solution of 2-(1,3-dioxolan-2-yl)-4,6-difluorobenzaldehyde (from step 1, 1.0 g, 4.67 mmol) in dry tetrahydrofuran (10 mL) at 0° C. was added methyl magnesium bromide (2.33 mL, 3 M in ether, 4.67 mmol). The resulting solution was stirred at room temperature for 1 hr. The reaction mixture was quenched with saturated ammonium chloride (10 mL) at 0° C. and diluted with ethyl acetate (100 mL). The organic layer was separated, washed brine and dried over Na$_2$SO$_4$. The solvent was removed under reduced pressure which afforded the title compound 1-(2-(1,3-dioxolan-2-yl)-4,6-difluorophenyl)ethan-1-ol (950 mg) as a colorless liquid. The crude compound was carried forwarded to next step without further purification.

$^1$H NMR (300 MHz, CDCl$_3$) δ 7.17 (dd, J=2.4, 6.3 Hz, 1H), 6.89-6.72 (m, 1H), 6.17 (s, 1H), 5.31 (dd, J=6.9, 13.5 Hz, 1H), 4.15-4.02 (m, 4H), 2.64-2.59 (m. 1H), 1.58 (d, J=9.0 Hz, 3H).

Step 3: 2-(3,5-difluoro-2-(1-fluoroethyl)phenyl)-1,3-dioxolane

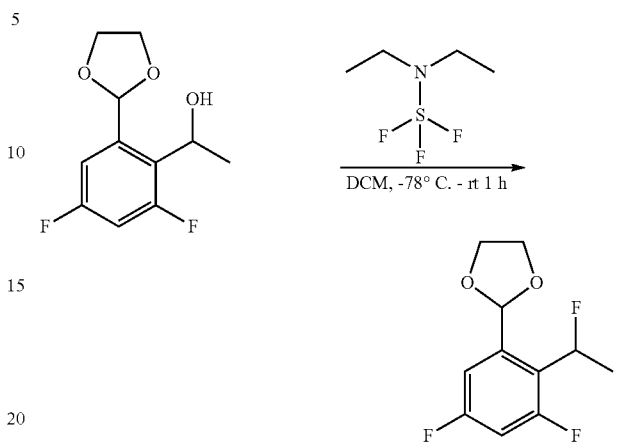

To a solution of 1-(2-(1,3-dioxolan-2-yl)-4,6-difluorophenyl)ethan-1-ol (from step 2, 950 mg, 4.13 mmol) in dichloromethane (10 mL) at −78° C. was added diethylaminosulfur trifluoride (1.0 g, 6.13 mmol). The resulting solution was stirred at room temperature for 1 hr. The reaction mixture was quenched with saturated ammonium chloride (10 mL) at 0° C. and diluted with ethyl acetate (100 mL). The organic layer was separated, washed with brine and dried over Na$_2$SO$_4$. The solvent was removed under reduced pressure and afforded the title compound 2-(3,5-difluoro-2-(1-fluoroethyl)phenyl)-1,3-dioxolane (600 mg) as a thick yellow liquid. The crude compound was carried forward to next step without further purification.

$^1$H NMR (300 MHz, CDCl$_3$) δ 7.20 (dd, J=2.4, 6.3 Hz, 1H), 6.87-6.75 (m, 1H), 6.15-5.98 (m, 1H), 6.11 (s, 1H), 4.15-4.02 (m, 4H), 1.70 (dd, J=6.6, 22.8 Hz, 3H).

Step 4: 3,5-difluoro-2-(1-fluoroethyl)benzaldehyde

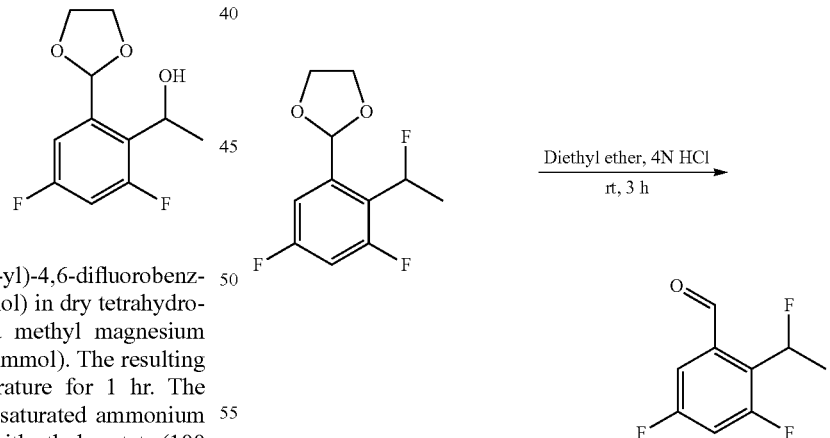

To a solution of 2-(3,5-difluoro-2-(1-fluoroethyl)phenyl)-1,3-dioxolane (from step 3, 600 mg, 2.58 mmol) and in diethyl ether (10 mL) was added 4N HCl (2 mL) at room temperature. The resulting solution was stirred at room temperature for 3 hrs. This was washed with water (50 mL) and saturated NaHCO$_3$ solution (100 mL), brine and dried over Na$_2$SO$_4$. The solvent was removed under reduced pressure affording the title compound 3,5-difluoro-2-(1fluoroethyl)benzaldehyde (200 mg) as a colorless liquid. (Note: The obtained aldehyde is volatile in nature)

¹H NMR (300 MHz, CDCl₃) δ 10.44 (d, J=3.0 Hz, 1H), 7.20 (d, J=9.3 Hz, 1H), 7.10-6.98 (m, 1H), 6.43-6.19 (m, 1H), 1.78 (dd, J=7.2, 23.1 Hz, 3H).

Step 5: 3-ethyl 5-methyl 2-(acetoxymethyl)-4-(3,5-difluoro-2-(1-fluoroethyl)phenyl)-6-methyl-1,4-dihydropyridine-3,5-dicarboxylate

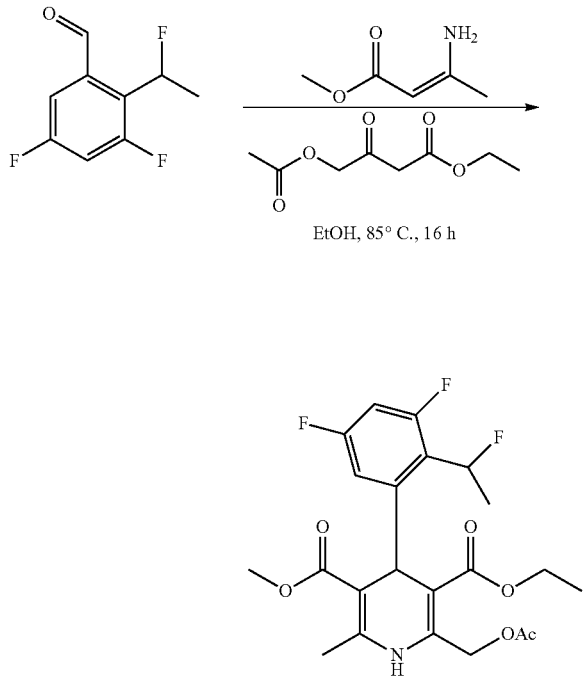

3-ethyl 5-methyl 2-(acetoxymethyl)-4-(3,5-difluoro-2-(1-fluoroethyl)phenyl)-6-methyl-1,4-dihydropyridine-3,5-dicarboxylate was synthesized using step 1 of general method II (using aldehyde from step 4, 200 mg, 1.06 mmol) to give 3-ethyl 5-methyl 2-(acetoxymethyl)-4-(3,5-difluoro-2-(1-fluoroethyl)phenyl)-6-methyl-1,4-dihydro pyridine-3,5-dicarboxylate (800 mg, crude).

LCMS Rt=1.738 min; MS m/z 456.3 [M+H]+; [Method 7]

Step 6: methyl 4-(3,5-difluoro-2-(1-fluoroethyl) phenyl)-2-methyl-5-oxo-1,4,5,7-tetrahydrofuro[3,4-b]pyridine-3-carboxylate

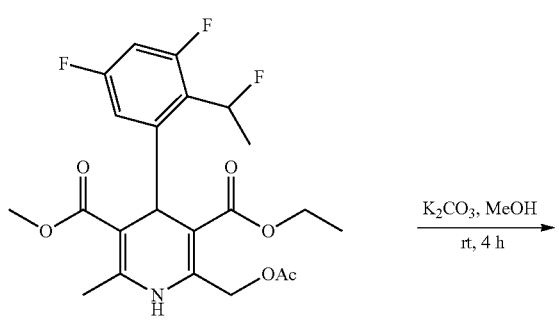

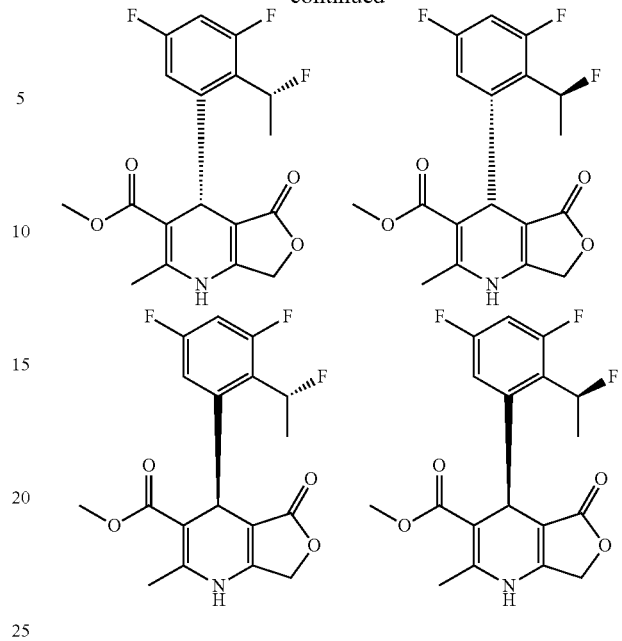

Methyl 4-(3,5-difluoro-2-(1-fluoroethyl)phenyl)-2-methyl-5-oxo-1,4,5,7-tetrahydrofuro[3,4-b]pyridine-3-carboxylate was synthesized using step 2 of general method II (using crude intermediate from step 5, 800 mg, 1.75 mmol). Crude product was purified by silica flash chromatography (0→80%) ethyl acetate in petroleum ether affording the title compound methyl 4-(3,5-difluoro-2-(1-fluoroethyl)phenyl)-2-methyl-5-oxo-1,4,5,7-tetrahydrofuro[3,4-b]pyridine-3-carboxylate (100 mg) as an off white solid.

Diastereomeric mixture was separated into isomers using preparative HPLC [Method 4], 39 mg of first eluting diastereomer as a white solid and 35 mg of second eluting diastereomer as a white solid. Peak 1: 39 mg and Peak 2: 35 mg was further separated into single enantiomers using preparative chiral HPLC [Method 1].

Example 7

9 mg of first eluting enantiomer as a white solid

Chiral HPLC Rt=5.77 min (Mobile Phase: A=n-HEXANE, B=ETHANOL (1:1); 1 mL/min; Isocratic: 70:30 (A:B); Column: Regis, (S,S) Whelk-O1-(250×4.6 mm, 5 micron).

LCMS Rt=1.492 min; MS m/z 366.0 [M–H]–; [Method 12]

¹H NMR (400 MHz, Chloroform-d) δ 8.03 (s, 1H), 6.71-6.62 (m, 2H), 6.59-6.39 (m, 1H), 5.06 (s, 1H), 4.66 (d, J=1.7 Hz, 2H), 3.55 (s, 3H), 2.40 (s, 3H), 1.90-1.67 (m, 3H).

Example 7b 9 mg of second enantiomer as a white solid.

Chiral HPLC Rt=7.806 min (Mobile Phase: A=n-HEXANE, B=ETHANOL (1:1); 1 mL/min; Isocratic: 70:30 (A:B); Column: Regis, (S,S) Whelk-O1-(250×4.6 mm, 5 micron).

LCMS Rt=1.487 min; MS m/z 366.0 [M–H]–; [Method 12]

¹H NMR (400 MHz, Chloroform-d) δ 6.78-6.63 (m, 2H), 6.43-6.19 (m, 2H), 5.11 (s, 1H), 4.78-4.71 (m, 2H), 3.59 (s, 3H), 2.45 (d, J=0.5 Hz, 3H), 1.92 (ddd, J=23.2, 6.7, 1.5 Hz, 3H).

Example 7c 7 mg of third eluting enantiomer as a white solid
Chiral HPLC Rt=10.16 min (Mobile Phase: A=n-HEXANE, B=ETHANOL (1:1); 1 mL/min; Isocratic: 70:30 (A:B); Column: Regis, (S,S) Whelk-O1-(250×4.6 mm, 5 micron).
LCMS Rt=1.493 min; MS m/z 366.0 [M–H]–; [Method 12]
¹H NMR (400 MHz, Chloroform-d) δ 6.73-6.61 (m, 3H), 6.40-6.20 (m, 1H), 5.18-5.06 (m, 1H), 4.80-4.67 (m, 2H), 3.58 (s, 3H), 2.43 (s, 3H), 1.91 (ddd, J=23.2, 6.6, 1.5 Hz, 3H).

Example 7d 7 mg of fourth eluting enantiomer as a white solid
Chiral HPLC Rt=11.83 min (Mobile Phase: A=n-HEXANE, B=ETHANOL (1:1); 1 mL/min; Isocratic: 70:30 (A:B); Column: Regis, (S,S) Whelk-O1-(250×4.6 mm, 5 micron).
LCMS Rt=1.510 min; MS m/z 366.0 [M–H]–; [Method 12]
¹H NMR (400 MHz, Chloroform-d) δ 7.81 (s, 1H), 6.67 (t, J=9.0, 9.0 Hz, 2H), 6.50 (dq, J=44.5, 6.7, 6.7, 6.7 Hz, 1H), 5.06 (s, 1H), 4.66 (s, 2H), 3.55 (s, 3H), 2.41 (s, 3H), 1.80 (dd, J=22.8, 6.6 Hz, 3H).

Example 8. Methyl (S)-4-(3-fluoro-2-(2-fluoropropan-2-yl)phenyl)-2-methyl-5-oxo-1,4,5,7-tetrahydrofuro[3,4-b]pyridine-3-carboxylate Step-1: 2-(2-bromo-6-fluorophenyl)propan-2-ol To a solution of commercially available 1-(2-bromo-6-fluorophenyl)ethan-1-one (11.0 g, 50.69 mmol) in dry tetrahydrofuran (100 mL) at −15° C. was added methyl magnesium bromide (33.8 mL, 3 M in ether, 101.3 mmol) dropwise. The resulting solution was slowly allowed to warm to room temperature and stirred for an additional 1 hr. The reaction mixture was quenched with saturated ammonium chloride (30 mL) at 0° C. and diluted with ethyl acetate (500 mL). The organic layer was separated, washed with brine and dried over Na₂SO₄. The solvent was removed under reduced pressure and purification of the crude product by silica chromatography (0→10%) ethyl acetate in petroleum ether afforded the title compound 2-(2-bromo-6-fluorophenyl)propan-2-ol (10 g) as a colorless liquid.

¹H NMR (300 MHz, Chloroform-d) δ 7.46-7.34 (m, 1H), 7.13-6.94 (m, 2H), 3.44 (bs, 1H), 1.77 (s, 3H), 1.76 (s, 3H).

Step 2: 1-bromo-3-fluoro-2-(2-fluoropropan-2-yl)benzene

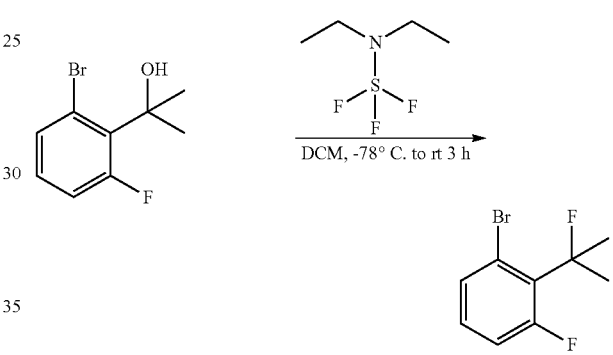

To a solution of 2-(2-bromo-6-fluorophenyl)propan-2-ol (from step 1, 7.0 g, 30.02 mmol) in dichloromethane (10 mL) at −78° C. was added diethylaminosulfur trifluoride (8.06 mL, 60.06 mmol). The resulting solution was stirred at room temperature for 3 hrs. The reaction mixture was quenched with saturated ammonium bicarbonate solution (10 mL) at 0° C. and diluted with ethyl acetate (100 mL). The organic layer was separated, washed with brine and dried over Na₂SO₄. The solvent was removed under reduced pressure and purification of the crude product by silica chromatography (0→10%) ethyl acetate in petroleum ether afforded the title compound 1-bromo-3-fluoro-2-(2-fluoropropan-2-yl)benzene (4.0 g) as a colorless liquid.

¹H NMR (300 MHz, Chloroform-d) δ 7.45 (m, 1H), 7.17-6.87 (m, 2H), 1.89 (s, 3H), 1.82 (s, 3H).

Step 3: 1-fluoro-2-(2-fluoropropan-2-yl)-3-vinylbenzene

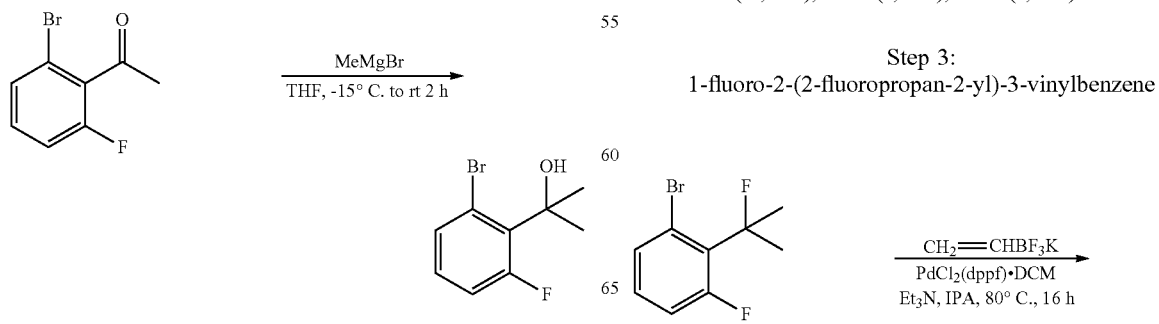

-continued

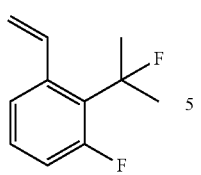

To a solution of 1-bromo-3-fluoro-2-(2-fluoropropan-2-yl)benzene (from step 2, 4.0 g, 17.02 mmol) and potassium vinyltrifluoroborate (4.55 g, 34.04 mmol) in isopropyl alcohol (40 mL) was added triethylamine (7.0 mL, 51.06 mmol) and [1,1'-Bis(diphenylphosphino)ferrocene]dichloropalladium (II).DCM (1.39 g, 1.702 mmol). The resulting solution was degassed with Argon gas for 10 min and stirred at 80° C. for 16 hrs. The reaction mixture was filtered and washed with ethyl acetate (100 mL). The filtrate was added to water (50 mL), extracted into ethyl acetate (200 mL), washed with brine and dried over $Na_2SO_4$. The solvent was removed under reduced pressure and purification of the crude product by silica flash chromatography (0→5%) ethyl acetate in petroleum ether afforded the title compound 1-fluoro-2-(2-fluoropropan-2-yl)-3-vinylbenzene (2.0 g) as a colorless liquid.

$^1$H NMR (300 MHz, Chloroform-d) δ 7.44-7.30 (m, 1H), 7.25-7.10 (m, 2H), 7.03-6.76 (m, 1H), 5.45-5.16 (m, 2H), 1.84 (s, 3H), 1.76 (s, 3H).

Step 4:
3-fluoro-2-(2-fluoropropan-2-yl)benzaldehyde

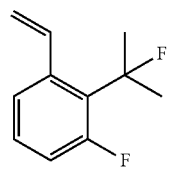

To a solution of 1-fluoro-2-(2-fluoropropan-2-yl)-3-vinylbenzene (from step 3, 2.0 g, 10.97 mmol) and ruthenium chloride.XH$_2$O (227 mg, 1.097 mmol) in dichloromethane (60 mL) and water (15 mL) was added diacetoxy iodobenzene (10.6 g, 32.93 mmol). The resulting solution was stirred at room temperature for 2 hrs. The reaction mixture was filtered and washed with ethyl acetate (200 mL). The filtrate was added to water (200 mL), extracted into ethyl acetate (500 mL), washed with brine and dried over $Na_2SO_4$. The solvent was removed under reduced pressure and purification of the crude product by silica flash chromatography (0→5%) ethyl acetate in petroleum ether afforded the title compound 3-fluoro-2-(2-fluoropropan-2-yl)benzaldehyde (800 mg) as a colorless liquid.

$^1$H NMR (400 MHz, Chloroform-d) δ 10.57 (s, 1H), 7.61-7.46 (m, 1H), 7.48-7.30 (m, 1H), 7.23 (m, 1H), 1.91 (s, 3H), 1.85 (s, 3H).

Step 5: 3-ethyl 5-methyl 2-(acetoxymethyl)-4-(3-fluoro-2-(2-fluoropropan-2-yl)phenyl)-6-methyl-1,4-dihydropyridine-3,5-dicarboxylate

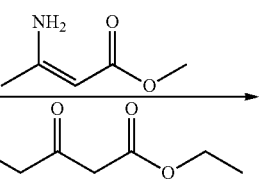

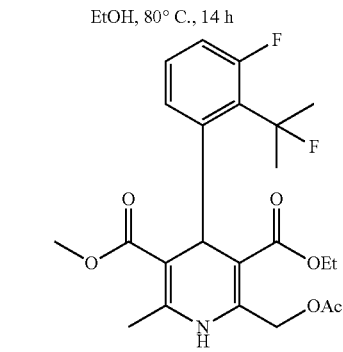

3-ethyl 5-methyl 2-(acetoxymethyl)-4-(3-fluoro-2-(2-fluoropropan-2-yl)phenyl)-6-methyl-1,4-dihydropyridine-3,5-dicarboxylate was synthesized using step 1 of general method II (using the aldehyde from step 4, 600 mg, 3.25 mmol) to give (230 mg, crude).

LCMS Rt=2.279 min; MS m/z 452.4 [M+H]+; [Method 9]

Step 6: methyl 4-(3-fluoro-2-(2-fluoropropan-2-yl)phenyl)-2-methyl-5-oxo-1,4,5,7-tetrahydrofuro[3,4-b]pyridine-3-carboxylate

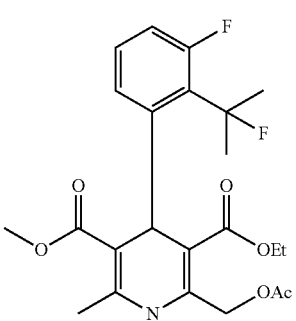

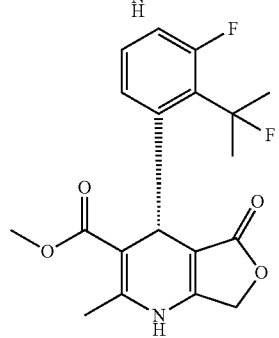
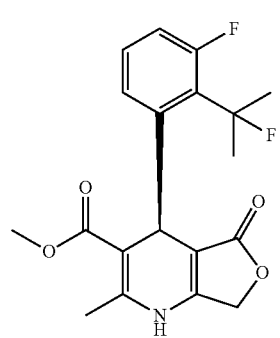

Methy 4-(3-fluoro-2-(2-fluoropropan-2-yl)phenyl)-2-methyl-5-oxo-1,4,5,7-tetrahydrofuro[3,4-b]pyridine-3-carboxylate was synthesized using step 2 of general method II (using the intermediate from step 5, 200 mg, 0.509 mmol). Crude product was purified by silica flash chromatography (0→60%) ethyl acetate in petroleum ether affording the title compound methyl 4-(3-fluoro-2-(2-fluoropropan-2-yl)phenyl)-2-methyl-5-oxo-1,4,5,7-tetrahydrofuro[3,4-b]pyridine-3-carboxylate (30 mg) as an off white solid. LCMS Rt=1.477 min; MS m/z 362.2 [M−H]−; [Method 12]

The racemic sample was separated into its enantiomers by chiral SFC (Mobile Phase: 15% MeOH/$CO_2$, 80 mL/min; Column: IC 21×250 mm, 5 μm)

Example 8

6.0 mg of the first eluting enantiomer as a white solid (23.8%).
SFC Rt=1.98 min (Chiralpak IC 4.6×100 mm, 5 μm, 5→55% MeOH/$CO_2$)
LCMS Rt=2.04 min; MS m/z 362.2 [M−H]−; [Method 4]
$^1$H NMR (400 MHz, DMSO-d6) δ 9.67 (s, 1H), 7.25 (td, J=8.0, 5.6 Hz, 1H), 7.13 (dd, J=8.0, 1.5 Hz, 1H), 7.05-6.89 (m, 1H), 5.83 (d, J=15.2 Hz, 1H), 4.75 (s, 2H), 3.43 (s, 3H), 2.28 (s, 3H), 1.83 (ddd, J=30.8, 24.0, 1.8 Hz, 6H).

Example 8b 6.0 mg of the second eluting enantiomer as a white solid (23.8%).
SFC Rt=2.35 min (Chiralpak IC 4.6×100 mm, 5 μm, 5→55% MeOH/$CO_2$)
LCMS Rt=2.06 min; MS m/z 362.4 [M−H]−; [Method 4]
$^1$H NMR (400 MHz, DMSO-d6) δ 9.67 (s, 1H), 7.25 (td, J=7.9, 5.5 Hz, 1H), 7.13 (dd, J=7.8, 1.3 Hz, 1H), 7.04-6.86 (m, 1H), 5.83 (d, J=15.2 Hz, 1H), 4.75 (s, 2H), 3.43 (s, 3H), 2.28 (s, 3H), 1.83 (ddd, J=30.9, 23.9, 1.8 Hz, 6H).

Example 9. Methyl (S)-4-(3-fluoro-2-(2,2,2-trifluoroethyl)phenyl)-2-methyl-5-oxo-1,4,5,7-tetrahydrofuro[3,4-b]pyridine-3-carboxylate

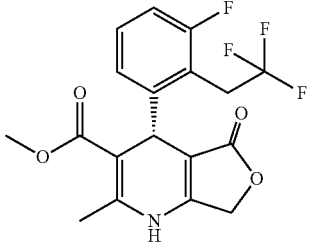 [SMILES: COC(=O)C1=C(C)NC2=C(C(=O)OC2)[C@H]1c1cccc(F)c1CC(F)(F)F]

Step 1: 2-(2-bromo-3-fluorophenyl)-1,3-dioxolane

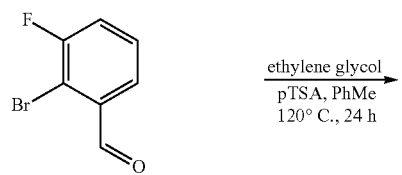

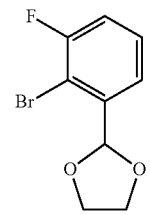

To a solution of commercially available 2-bromo-3-fluorobenzaldehyde (60 g, 295.56 mmol) and ethylene glycol (65.4 mL, 1182.2 mmol) in toluene (600 mL) was added p-toluenesulfonic acid monohydrate (28.11 g, 147.78 mmol). The resulting solution was stirred at 120° C. for 24 hrs using dean-stark apparatus. The solvent was added to water (2 L) and extracted into ethyl acetate (3 L). EtOAc was washed with saturated $NaHCO_3$ solution (1 L), brine and dried over $Na_2SO_4$. The solvent was removed under reduced pressure and purification of the crude product by silica flash chromatography (0→10%) ethyl acetate in petroleum ether afforded the title compound 2-(2-bromo-3-fluorophenyl)-1,3-dioxolane (60 g) as a colorless liquid.

$^1$H NMR (400 MHz, $CDCl_3$) δ 7.42-7.37 (m, 1H), 7.34-7.29 (m, 1H), 7.16-7.10 (m, 1H), 6.10 (s, 1H), 4.19-4.09 (m, 4H).

Step 2: 2-(1,3-dioxolan-2-yl)-6-fluorobenzaldehyde

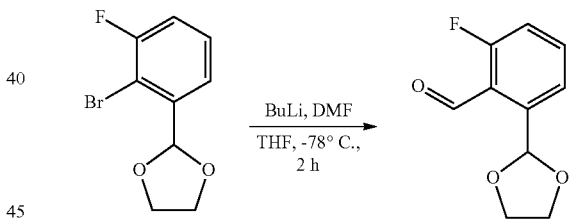

To a solution of 2-(2-bromo-3-fluorophenyl)-1,3-dioxolane (from step 1, 7 g, 28.45 mmol) in THF (70 mL) under nitrogen atmosphere at to −78° C. was added n-butyllithium in n-Hexane solution (13.66 mL, 2.5M, 58.5 mmol) dropwise over 10 min. The mixture was stirred for 45 min at −78° C. then DMF (2.5 g, 34.15 mmol) was added. Reaction stirred for 1.15 h at −78° C. before being quenched with saturated ammonium chloride solution (50 mL) and extracted with ethyl acetate (2×100 mL). Combined organic layer was washed with water (50 mL), followed by brine (50 mL) and dried over $Na_2SO_4$. The solvent was removed under reduced pressure and purification of the crude product by silica flash chromatography (0→50%) ethyl acetate in petroleum ether afforded the title compound 2-(1,3-dioxolan-2-yl)-6-fluorobenzaldehyde (5 g) as a colorless liquid.

$^1$H NMR (300 MHz, Chloroform-d) δ 10.52 (s, 1H), 7.67-7.53 (m, 2H), 7.22-7.12 (m, 1H), 6.50 (s, 1H), 4.27-3.99 (m, 4H).

Step 3: 2-(2-(2,2-difluorovinyl)-3-fluorophenyl)-1,3-dioxolane

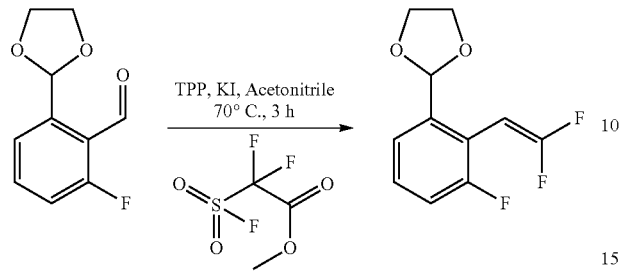

A solution of acetonitrile (65 mL), triphenylphosphine (28.1 g, 107.1 mmol), potassium iodide (11.85 g, 71.4 mmol) and 2-(1,3-dioxolan-2-yl)-6-fluorobenzaldehyde (from step 2, 7 g, 35.7 mmol) was stirred for 30 min at 70° C. under $N_2$. Methyl 2,2-difluoro-2-(fluorosulfonyl)acetate (12 g, 62.4 mmol) was added slowly over a period of 10 min, (color was turned to yellow upon addition) resulting mixture was stirred for another 3 hrs at 70° C. The reaction mixture was cooled to room temperature, diluted with diethyl ether, and precipitated solids were filtered and washed with diethyl ether (100 mL). The solvent was removed under reduced pressure and purification of the crude product by silica flash chromatography (0→5%) ethyl acetate in petroleum ether afforded the title compound 2-(2-(2,2-difluorovinyl)-3-fluorophenyl)-1,3-dioxolane (6.9 g) as a light yellow liquid.

$^1$H NMR (300 MHz, Chloroform-d) δ 7.39 (dd, J=7.8, 1.4 Hz, 1H), 7.31 (m, 1H), 7.11 (m, 1H), 5.87 (s, 1H), 5.39 (m, 1H), 4.21-3.95 (m, 4H).

Step 4: 2-(3-fluoro-2-(2,2,2-trifluoroethyl)phenyl)-1,3-dioxolane

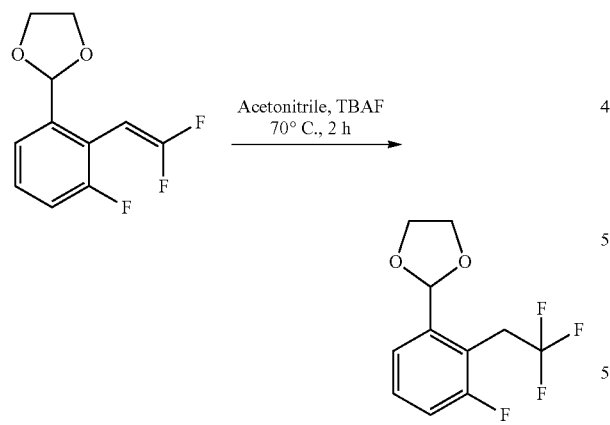

To a solution of 2-(2-(2,2-difluorovinyl)-3-fluorophenyl)-1,3-dioxolane (from step 3, 2.7 g, 11.73 mmol) in MeCN was added tetrabutylammonium fluoride in THF (13.7 g, 1M, 13.7 mmol). Reaction was heated to 70° C. in a closed system and the resulting solution was stirred for 2 hrs. Reaction mixture was cooled, diluted with diethyl ether, was washed with water (50 mL), saturated $NaHCO_3$ solution (100 mL), brine and dried over $Na_2SO_4$. The solvent was removed under reduced pressure and purification of the crude product by silica flash chromatography (0→10%) ethyl acetate in petroleum ether afforded the title compound 2-(3-fluoro-2-(2,2,2-trifluoroethyl)phenyl)-1,3-dioxolane (1.2 g) as a colorless liquid.

$^1$H NMR (300 MHz, Chloroform-d) δ 7.49-7.42 (m, 1H), 7.35 (m, 1H), 7.17-7.05 (m, 1H), 6.03 (s, 1H), 4.25-3.90 (m, 4H), 3.75 (m, 2H).

Step 5: 3-fluoro-2-(2,2,2-trifluoroethyl)benzaldehyde

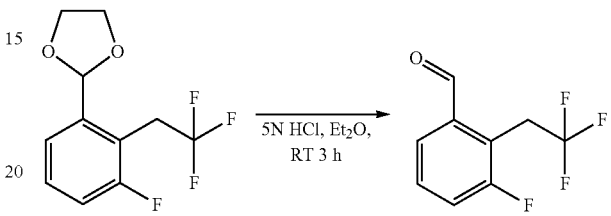

To a solution of 2-(3-fluoro-2-(2,2,2-trifluoroethyl)phenyl)-1,3-dioxolane (from step 4, 2 g, 8.0 mmol) in diethyl ether (40 mL) was added 6N HCl (5 mL). The resulting solution was stirred at room temperature for 3 hrs. This was washed with water (50 mL), saturated $NaHCO_3$ solution (100 mL), brine and dried over $Na_2SO_4$. The solvent was removed under reduced pressure and purification of the crude product by silica flash chromatography (0→5%) ethyl acetate in petroleum ether afforded the title compound 3-fluoro-2-(2,2,2-trifluoroethyl)benzaldehyde (1.2 g) as a colorless liquid. The crude product was taken as such to the next step without further purification.

Step 6: 3-ethyl 5-methyl 2-(acetoxymethyl)-4-(3-fluoro-2-(2,2,2-trifluoroethyl)phenyl)-6-methyl-1,4-dihydropyridine-3,5-dicarboxylate

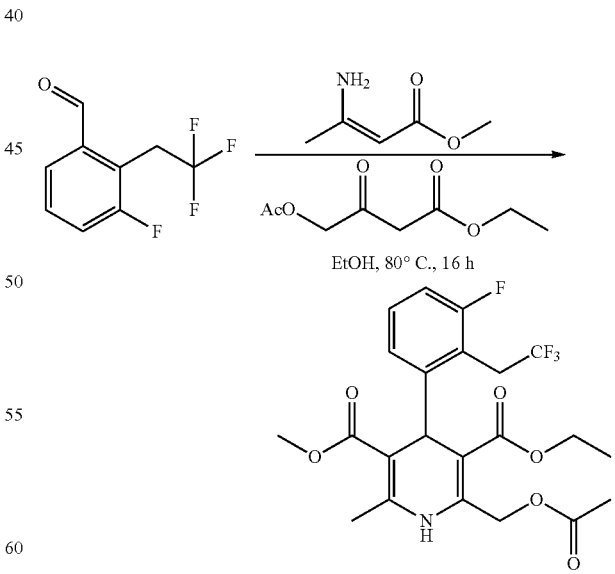

3-ethyl 5-methyl 2-(acetoxymethyl)-4-(3-fluoro-2-(2,2,2-trifluoroethyl)phenyl)-6-methyl-1,4-dihydropyridine-3,5-dicarboxylate was synthesized using step 1 of general method II (using the aldehyde from step 5, 150 mg, 0.728 mmol) to give tittle compound 3-ethyl 5-methyl 2-(acetoxymethyl)-4-(3-fluoro-2-(2,2,2-trifluoroethyl)phenyl)-6-methyl-1,4-dihydropyridine-3,5-dicarboxylate (100 mg, crude).

LCMS Rt=1.736 min; MS m/z 474.1 [M+H]+; [Method 1],

Step 7: methyl 4-(3-fluoro-2-(2,2,2-trifluoroethyl)phenyl)-2-methyl-5-oxo-1,4,5,7-tetrahydrofuro[3,4-b]pyridine-3-carboxylate

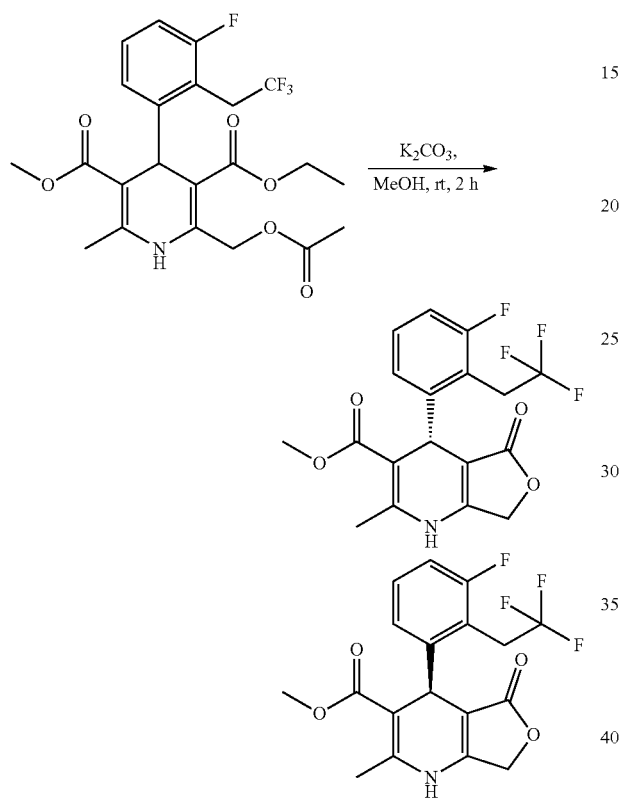

Methyl 4-(3-fluoro-2-(2,2,2-trifluoroethyl)phenyl)-2-methyl-5-oxo-1,4,5,7-tetrahydrofuro[3,4-b]pyridine-3-carboxylate was synthesized using step 2 of general method II (using the intermediate from step 5, 100 mg, 0.211 mmol). Crude product was purified by silica flash chromatography (0→50%) ethyl acetate in petroleum ether afforded the title compound methyl 4-(3-fluoro-2-(2,2,2-trifluoroethyl)phenyl)-2-methyl-5-oxo-1,4,5,7-tetrahydrofuro[3,4-b]pyridine-3-carboxylate (40 mg) as an off white solid.

LCMS Rt=1.508 min; MS m/z 386.3 [M+H]+; [Method 7]

Racemic mixture was separated into its enantiomers using chiral HPLC [Method 3].

Example 9

11 mg of first eluting enantiomer as a white solid, (22%)
Chiral HPLC Rt=6.264 min (Mobile Phase: A=n-HEXANE, B=0.1% TFA IN ETHANOL:METHANOL (1:1); 1 mL/min; Isocratic: 80:20 (A:B); Column: Lux, Cellulose-4 (250×4.6 mm, 5 micron).
LCMS Rt=1.508 min; MS m/z 386.3 [M+H]+; [Method 7]

$^1$H NMR (400 MHz, Chloroform-d) δ 7.41 (s, 1H), 7.25-7.19 (m, 1H), 7.02-6.98 (m, 1H), 6.93 (ddd, J=9.5, 8.1, 1.3 Hz, 1H), 5.15 (s, 1H), 4.66-4.57 (m, 2H), 4.43 (ddd, J=19.7, 11.2, 5.9 Hz, 1H), 3.80-3.63 (m, 1H), 3.45 (s, 3H), 2.44 (s, 3H).

Example 9b 11 mg of second eluting enantiomer as a white solid, (22%)
Chiral HPLC Rt=6.708 min (Mobile Phase: A=n-HEXANE, B=0.1% TFA IN ETHANOL:METHANOL (1:1); 1 mL/min; Isocratic: 80:20 (A:B); Column: Lux, Cellulose-4 (250×4.6 mm, 5 micron).
LCMS Rt=1.509 min; MS m/z 386.4 [M+H]+; [Method 7]

$^1$H NMR (400 MHz, Chloroform-d) δ 7.56 (s, 1H), 7.25-7.19 (m, 1H), 7.02-6.98 (m, 1H), 6.93 (dd, J=9.5, 8.1 Hz, 1H), 5.15 (s, 1H), 4.66-4.57 (m, 2H), 4.43 (m, 1H), 3.80-3.63 (m, 1H), 3.45 (s, 3H), 2.44 (s, 3H).

Example 10. Methyl (S)-4-(3-fluoro-2-((S or R)-1-fluoroethyl)phenyl)-2-methyl-5-oxo-1,4,5,7-tetrahydrofuro[3,4-b]pyridine-3-carboxylate

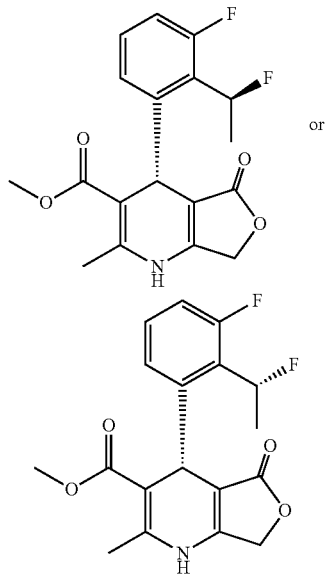

Step 1: 1-(2-(1,3-dioxolan-2-yl)-6-fluorophenyl)ethan-1-ol

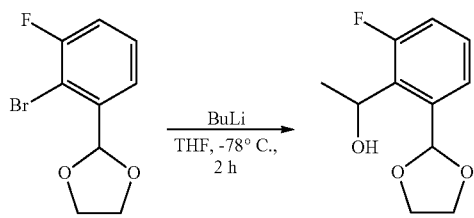

To a solution of commercially available 2-(2-bromo-3-fluorophenyl)-1,3-dioxolane (from step 1, example 1, 30 g, 121.42 mmol) in THF (300 mL) under nitrogen atmosphere was cooled to −78° C. n-BuLi in n-Hexane solution (58.3 mL, 2.5M, 147.71 mmol) was added over 10 min and the resulting mixture stirred for 1 h at −78° C. Acetaldehyde (6.42 g, 145.71 mmol) was added and the resulting mixture stirred for 1 h at −78° C. The reaction mixture was quenched with saturated ammonium chloride solution (50 mL) and extracted with ethyl acetate (2×100 mL). The combined organic phases were washed with water (50 mL), brine (50 mL) and dried over $Na_2SO_4$. The solvent was removed under reduced pressure and purification of the crude product by silica flash chromatography (0→10%) ethyl acetate in petroleum ether afforded the title compound 1-(2-(1,3-dioxolan-2-yl)-6-fluorophenyl)ethan-1-ol (15 g) as a colorless liquid.

$^1$H NMR (400 MHz, $CDCl_3$) δ 7.38 (d, J=8.0 Hz, 1H), 7.30-7.18 (m, 1H), 7.10-7.01 (m, 1H), 6.15 (s, 1H), 5.29 (td, J=6.9, 13.5 Hz, 1H), 4.15-3.95 (m, 4H), 2.75-2.69 (m. 1H), 1.58 (dd, J=6.6, 22.8 Hz, 3H).

Step 2: 2-(3-fluoro-2-(1-fluoroethyl)phenyl)-1,3-dioxolane

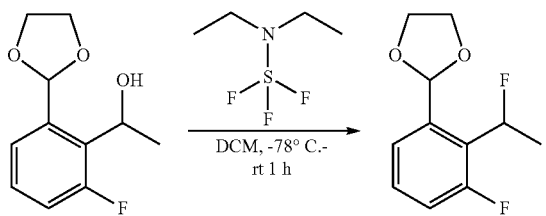

To a solution of 1-(2-(1,3-dioxolan-2-yl)-6-fluorophenyl)ethan-1-ol (from step 1, 15 g, 70.68 mmol) in dichloromethane (150 mL) at −78° C. was added diethylaminosulfur trifluoride (19.3 mL, 141.37 mmol). The resulting solution was allowed to warm and stirred at room temperature for 1 hr. The reaction mixture was quenched with saturated ammonium chloride (20 mL) at 0° C. and diluted with ethyl acetate (100 mL). The organic layer was separated, washed with brine and dried over $Na_2SO_4$. The solvent was removed under reduced pressure and purification of the crude product by silica flash chromatography (0→10%) ethyl acetate in petroleum ether afforded the title compound 2-(3-fluoro-2-(1-fluoroethyl)phenyl)-1,3-dioxolane (8.5 g) as a colorless liquid.

$^1$H NMR (300 MHz, $CDCl_3$) δ 7.38 (d, J=7.5 Hz, 1H), 7.30-7.18 (m, 1H), 7.13-7.01 (m, 1H), 6.20-5.95 (m, 1H), 6.10 (s, 1H), 4.16-4.02 (m, 4H), 1.74 (dd, J=7.2, 23.1 Hz, 3H).

Step 3: 3-fluoro-2-(1-fluoroethyl)benzaldehyde

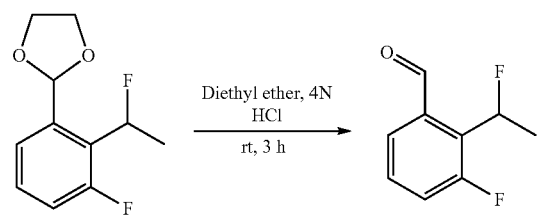

To a solution of 2-(3-difluoro-2-(1-fluoroethyl)phenyl)-1,3-dioxolane (from step 2, 8.5 g, 69.38 mmol) in diethyl ether (150 mL) was added 4N HCl (85 mL) at room temperature. The resulting solution was stirred at room temperature for 3 hrs. This was washed with water (100 mL), saturated $NaHCO_3$ solution (200 mL), brine and dried over $Na_2SO_4$. The solvent was removed under reduced pressure to afforded the title compound 3-difluoro-2-(1-fluoroethyl) benzaldehyde (6.5 g) as a colorless liquid. (Note: The obtained aldehyde is volatile in nature).

$^1$H NMR (300 MHz, Chloroform-d) δ 10.44 (d, J=1.0 Hz, 1H), 7.74 (d, J=7.7 Hz, 1H), 7.47 (td, J=8.1, 8.0, 5.2 Hz, 1H), 7.35-7.30 (m, 1H), 6.41 (dq, J=46.8, 6.6 Hz, 1H), 1.92-1.72 (m, 3H).

Step 4: 3-ethyl 5-methyl 2-(acetoxymethyl)-4-(3-fluoro-2-(1-fluoroethyl)phenyl)-6-methyl-1,4-dihydropyridine-3,5-dicarboxylate

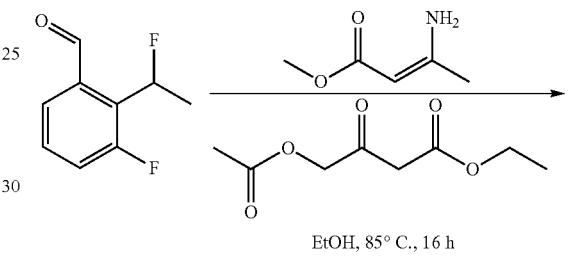

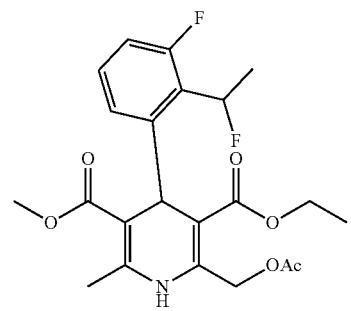

3-ethyl 5-methyl 2-(acetoxymethyl)-4-(3-fluoro-2-(1-fluoroethyl)phenyl)-6-methyl-1,4-dihydropyridine-3,5-dicarboxylate was synthesized using step 1 of general method II (using the aldehyde from step 3, 1000 mg, 1.88 mmol) to give 3-ethyl 5-methyl 2-(acetoxymethyl)-4-(3,5-difluoro-2-(1-fluoroethyl)phenyl)-6-methyl-1,4-dihydro pyridine-3,5-dicarboxylate along with 3-ethyl 5-methyl 2-(acetoxymethyl)-4-(3-fluoro-2-(1-fluoroethyl)phenyl)-6-methyl-1,4-dihydropyridine-3,5-dicarboxylate as crude that was directly taken onto step 5.

Step-5: methyl 4-(3-fluoro-2-(1-fluoroethyl)phenyl)-2-methyl-5-oxo-1,4,5,7-tetrahydrofuro[3,4-b]pyridine-3-carboxylate

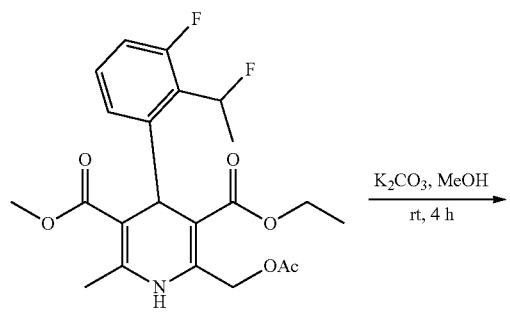

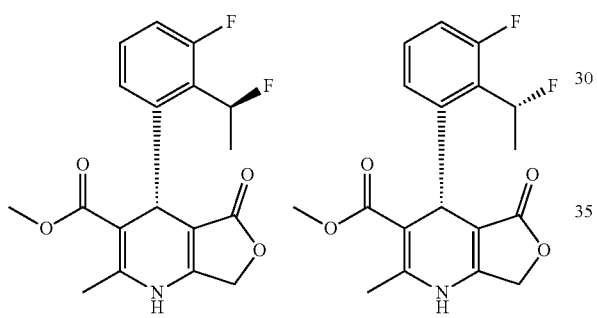

Methyl 4-(3-fluoro-2-(1-fluoroethyl)phenyl)-2-methyl-5-oxo-1,4,5,7-tetrahydrofuro[3,4-b]pyridine-3-carboxylate was synthesized using step 2 of general method II (using mixture of intermediate from step 4). Purification of crude product twice by silica flash chromatography (0→100%) ethyl acetate in heptane afforded the separated diastereomers of the title compound methyl 4-(3-fluoro-2-(1-fluoroethyl)phenyl)-2-methyl-5-oxo-1,4,5,7-tetrahydrofuro[3,4-b]pyridine-3-carboxylate (200 mg each) as off white solids.

200 mg of first eluting diastereomer was separated into its enantiomers using chiral SFC (Column: SS Whelk-O1 21×250 mm; Flow Rate: 80 g per minute; Cosolvent: 25% MeOH w\ NH3; Detection: 340 nm; BPR Set Point: 150 bar)

Example 10

80 mg of first eluting enantiomer as a white solid.
Chiral SFC Rt=2.0 min ((S,S) Whelk-O1 (3.5p) 3×100 mm; 5→55% MeOH w 0.1% NH3/CO2 2.5 mL/min 1800 psi).
LCMS Rt=2.01 min; MS m/z 348.3 [M–H]–; [Method 4]
$^1$H NMR (400 MHz, DMSO-d6) δ 99.87 (s, 1H), 7.32 (m, 1H), 7.06-6.97 (m, 2H), 6.44-6.23 (m, 1H), 4.98 (s, 1H), 4.92-4.77 (m, 2H), 3.43 (s, 3H), 2.32 (s, 3H), 1.86-1.75 (m, 3).
The remaining stereoisomers were not characterized Example 11. Methyl (S)-4-(2-((R or S)-1,2-difluoroethyl)-3-fluorophenyl)-2-methyl-5-oxo-1,4,5,7-tetrahydrofuro[3,4-b]pyridine-3-carboxylate

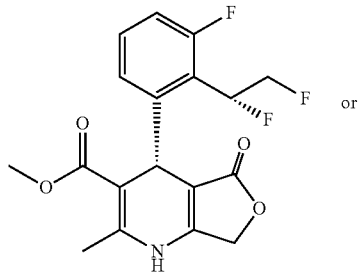 or

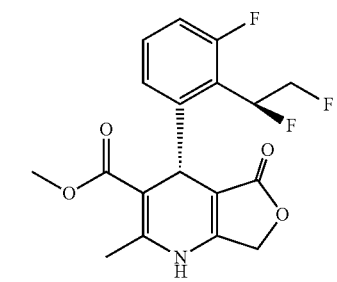

Step 1: 2-(2-bromo-3-fluorophenyl)-1,3-dioxolane

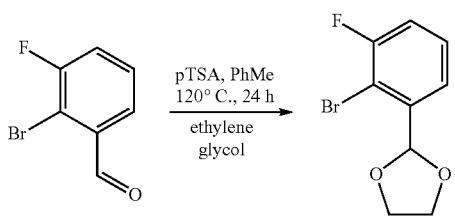 [SMILES: O=Cc1cccc(F)c1Br ; Fc1cccc(C2OCCO2)c1Br]

To a solution of commercially available 2-bromo-3-fluorobenzaldehyde (60 g, 295.56 mmol) and ethylene glycol (65.4 mL, 1182.2 mmol) in toluene (600 mL) was added p-toluenesulfonic acid monohydrate (28.11 g, 147.78 mmol). The resulting solution was stirred at 120° C. for 24 hrs using dean-stark apparatus. The reaction was added to water (2 L) and extracted into ethyl acetate (3 L). Ethyl acetate was washed with saturated NaHCO3 solution (1 L), brine and dried over Na2SO4. The solvent was removed under reduced pressure and purification of the crude product by silica flash chromatography (0→10%) ethyl acetate in petroleum ether afforded the title compound 2-(2-bromo-3-fluorophenyl)-1,3-dioxolane (60 g) as a colorless liquid.
$^1$H NMR (300 MHz, Chloroform-d) δ 7.40 (dd, J=7.8, 1.6 Hz, 1H), 7.35-7.25 (m, 1H), 7.13 (m, 1H), 6.10 (s, 1H), 4.30-3.90 (m, 4H).

Step 2: 1-(2-(1,3-dioxolan-2-yl)-6-fluorophenyl)-2-fluoroethan-1-one

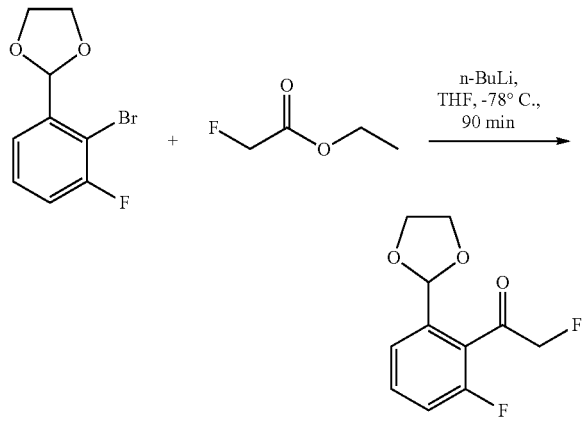

A solution of 2-(2-bromo-3-fluorophenyl)-1,3-dioxolane (from step 1, 26 g, 105.23 mmol) in THF (250 mL) under nitrogen atmosphere was cooled to −78° C. Then n-butyl-lithium in n-hexane solution (44.19 mL, 2.5M, 110.49 mmol) was added and reaction stirred for 30 min at −78° C. Then ethyl 2-fluoroacetate (22.33 g, 210.47 mmol) was added and the resulting mixture was stirred for another 60 min. at −78° C. The reaction mixture was quenched with saturated ammonium chloride solution (100 mL) and extracted with ethyl acetate (2×250 mL). Combined organic layers were washed with water (250 mL), brine (250 mL) and dried over Na$_2$SO$_4$. The solvent was removed under reduced pressure and purification of the crude product by silica flash chromatography (0→10%) ethyl acetate in petroleum ether afforded the title compound 1-(2-(1,3-dioxolan-2-yl)-6-fluorophenyl)-2-fluoroethan-1-one (16.2 g) as a colorless liquid.

$^1$H NMR (400 MHz, Chloroform-d) δ 7.45 (m, 1H), 7.37 (d, J=7.8, 1H), 7.13 (dd, J=9.3, 8.2 Hz, 1H), 6.02 (s, 1H), 5.23 (d, J=1.4 Hz, 1H), 5.11 (d, J=1.3 Hz, 1H), 4.08-3.87 (m, 4H).

Step 3: 1-(2-(1,3-dioxolan-2-yl)-6-fluorophenyl)-2-fluoroethan-1-ol

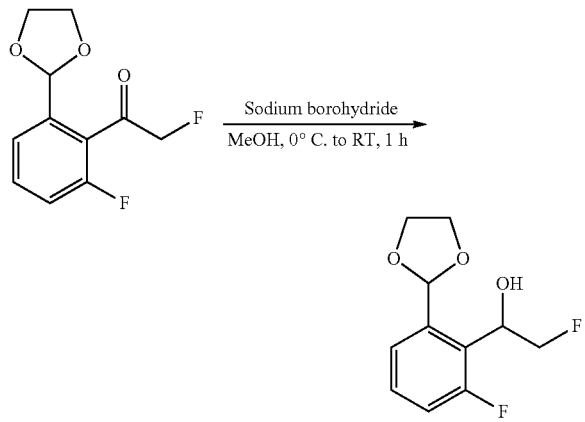

To a stirred solution of 1-(2-(1,3-dioxolan-2-yl)-6-fluorophenyl)-2-fluoroethan-1-one (19.6 g, 85.89 mmol) in methanol (100 mL) was added sodium borohydride (3.899 g, 103.07 mmol) at 0° C. under nitrogen atmosphere. The resulting mixture was stirred at room temperature for 1 h. Reaction mixture was quenched with ice water and extracted with ethyl acetate (2×250 mL). Combined organic layers were washed with water (250 mL), brine (250 mL) and dried over Na$_2$SO$_4$. The solvent was removed under reduced pressure and purification of the crude product by silica flash chromatography (0→30%) ethyl acetate in petroleum ether afforded the title compound 1-(2-(1,3-dioxolan-2-yl)-6-fluorophenyl)-2-fluoroethan-1-ol (18 g) as a colorless liquid.

$^1$H NMR (400 MHz, Chloroform-d) δ 7.44 (dd, J=7.9, 1.2 Hz, 1H), 7.33 (dd, J=8.0, 8.0 Hz, 1H), 7.10 (dd, J=8.2, 1.3 Hz, 1H), 6.13 (s, 1H), 5.47 (m, 1H), 4.98-4.51 (m, 2H), 4.22-3.97 (m, 4H), 3.04 (m, 1H).

Step 4: 2-(2-(1,2-difluoroethyl)-3-fluorophenyl)-1,3-dioxolane

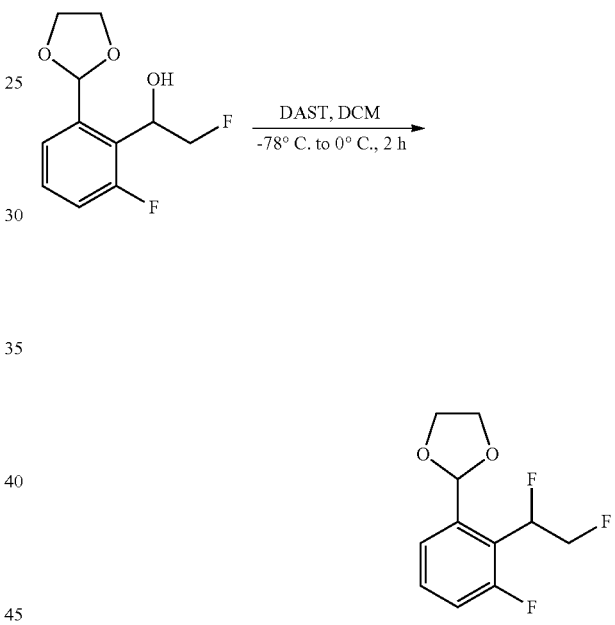

A solution of 1-(2-(1,3-dioxolan-2-yl)-6-fluorophenyl)-2-fluoroethan-1-ol (from step 3, 18 g, 78.18 mmol) in dichloromethane (150 mL) was cooled to −78° C. then diethylaminosulfur trifluoride (15.49 mL, 117.28 mmol) was added and the resulting reaction mixture was stirred at −78° C. for 1 h then was slowly brought to 0° C. and stirred for another 1 h. Water (150 mL) was added and product was extracted into dichloromethane (2×200 mL). Combined organic layers were washed with saturated sodium bicarbonate solution (2×200 mL), water (200 mL), brine (200 mL) and dried over Na$_2$SO$_4$.

The solvent was removed under reduced pressure and purification of the crude product by silica flash chromatography (0→10%) ethyl acetate in petroleum ether afforded the title compound 2-(2-(1,2-difluoroethyl)-3-fluorophenyl)-1,3-dioxolane (12.4 g) as a colorless liquid.

$^1$H NMR (400 MHz, Chloroform-d) δ 7.45 (d, J=7.8 Hz, 1H), 7.42-7.35 (m, 1H), 7.12 (dd, J=10.6, 8.2 Hz, 1H), 6.21 (m, 1H), 6.04 (s, 1H), 5.22-4.85 (m, 1H), 4.75-4.42 (m, 1H), 4.20-3.97 (m, 4H).

Step 5: 2-(1,2-difluoroethyl)-3-fluorobenzaldehyde

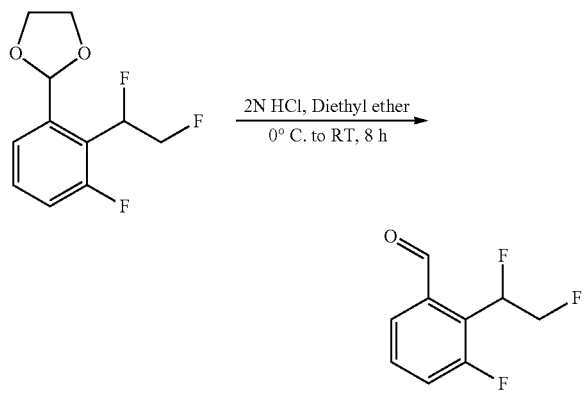

To a solution of 2-(2-(1,2-difluoroethyl)-3-fluorophenyl)-1,3-dioxolane (from step 4, 12.4 g, 53.40 mmol) in diethyl ether (150 mL) was added 2N HCl (100 mL) at 0° C. The resulting reaction mixture was stirred at room temperature for 8 hrs. Reaction mixture was added to water (100 ml) and extracted with diethyl ether (200 mL). Organic phase was washed with water (100 mL), brine (100 mL) and dried over $Na_2SO_4$. The solvent was removed under reduced pressure and purification of the crude product by silica flash chromatography (0→10%) ethyl acetate in petroleum ether afforded the title compound 2-(1,2-difluoroethyl)-3-fluorobenzaldehyde (10 g) as a colorless liquid.

$^1$H NMR (400 MHz, Chloroform-d) δ 10.30 (s, 1H), 7.88-7.70 (m, 1H), 7.56 (m, 1H), 7.44-7.30 (m, 1H), 6.70-6.36 (m, 1H), 4.95-4.70 (m, 2H)

Step 6: methyl 4-(2-(1,2-difluoroethyl)-3-fluorophenyl)-2-methyl-5-oxo-1,4,5,7-tetrahydrofuro[3,4-b]pyridine-3-carboxylate

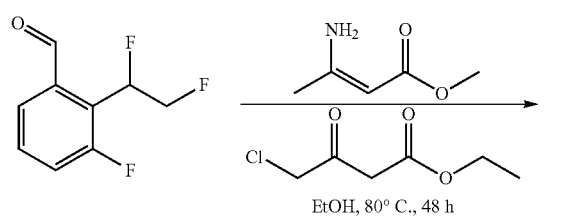

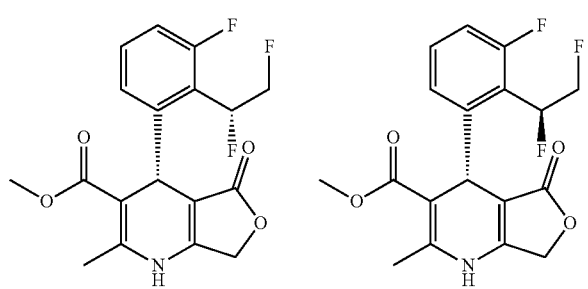

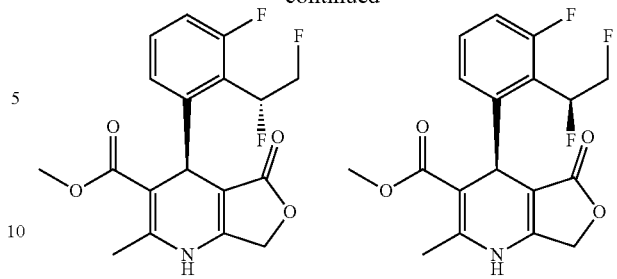

Methyl 4-(2-(1,2-difluoroethyl)-3-fluorophenyl)-2-methyl-5-oxo-1,4,5,7-tetrahydrofuro[3,4-b]pyridine-3-carboxylate was synthesized using general method I (using the aldehyde from step 5, 450 mg, 2.39 mmol). Crude product was purified by silica flash chromatography (0→70%) ethyl acetate in petroleum ether affording the title compound methyl-4-(2-(1,2-difluoroethyl)-3-fluorophenyl)-2-methyl-5-oxo-1,4,5,7-tetrahydrofuro[3,4-b]pyridine-3-carboxylate (400 mg) as a mixture of diastereomers and as an off white solid.

Diastereomeric mixture (400 mg) was separated using prep-HPLC [Method 7].

60 mg of first eluting diastereomer as a white solid.

LCMS Rt=1.463 min; MS m/z 365.85 [M−H]−; [Method 11]

$^1$H NMR (400 MHz, DMSO-d6) δ 9.93 (s, 1H), 7.42-7.39 (m, 1H), 7.17-6.96 (m, 2H), 6.48-6.47 (m, 1H), 5.22-4.69 (m, 2H), 5.04 (s, 1H), 4.89-4.83 (m, 2H), 3.42 (s, 3H), 2.37-2.30 (m, 3H).

56.4 mg of second eluting diastereomer as a white solid.

LCMS Rt=1.466 min; MS m/z 365.85 [M−H]−; [Method 12]

$^1$H NMR (400 MHz, DMSO-d6) δ 9.93 (s, 1H), 7.45-7.43 (m, 1H), 7.17-6.96 (m, 2H), 6.49-6.46 (m, 1H), 5.22-4.69 (m, 2H), 5.04 (s, 1H), 4.89-4.83 (m, 2H), 3.42 (s, 3H), 2.37-2.30 (m, 3H).

The second eluting diastereomer was further separated into its enantiomers using chiral SFC (Mobile Phase: 12% MeOH/CO$_2$, 70 mL/min; Column: OZ—H (2×25 cm)).

Example 11

22.8 mg of first eluting enantiomer as a white solid (77%).

SFC Rt=2.81 min ((SS) Whelk-O1 4.6×100 mm, 5 μm, 5→55% (1:1) MeOH/IPA (10 mM NH$_4$OH/CO$_2$)).

LCMS Rt=1.89 min; MS m/z 366.1 [M−H]−; [Method 10]

$^1$H NMR (400 MHz, DMSO-d6) δ 9.93 (s, 1H), 7.50-7.37 (m, 1H), 7.14-7.00 (m, 2H), 6.48 (ddd, J=48.9, 17.8, 8.6 Hz, 1H), 5.20-4.93 (m, 3H), 4.92-4.80 (m, 2H), 3.43 (s, 3H), 2.33 (s, 3H).

Example 11b 22.0 mg of the second eluting enantiomer as a white solid (74.1%)

SFC Rt=2.93 min ((SS) Whelk-O1 4.6×100 mm, 5 μm, 5→55% (1:1) MeOH/IPA (10 mM NH$_4$OH/CO$_2$)).

LCMS Rt=1.87 min; MS m/z 365.9 [M−H]−; [Method 10]

$^1$H NMR (400 MHz, DMSO-d6) δ 9.93 (s, 1H), 7.49-7.35 (m, 1H), 7.14-7.00 (m, 2H), 6.48 (ddd, J=48.5, 17.8, 8.3 Hz, 1H), 5.22-4.93 (m, 3H), 4.86 (d, J=3.8 Hz, 2H), 3.43 (s, 3H), 2.33 (s, 3H).

Example 12. Methyl (S)-4-(2-ethyl-3,5-difluorophenyl)-2-methyl-5-oxo-1,4,5,7-tetrahydrofuro[3,4-b]pyridine-3-carboxylate

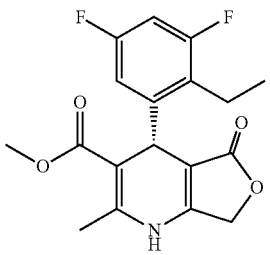 [SMILES: CCc1c(F)cc(F)cc1[C@H]1C(C(=O)OC)=C(C)NC2=C1C(=O)OC2]

Step 1: 3,5-difluoro-2-vinylbenzaldehyde

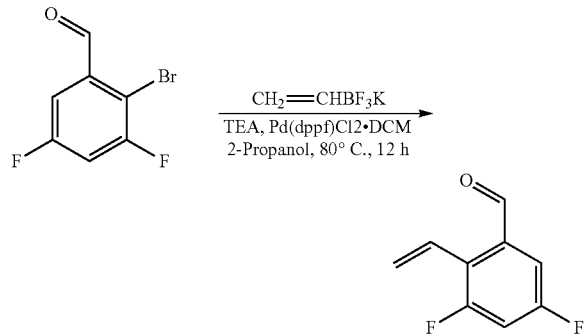

To a solution of commercially available 2-bromo-3,5-difluorobenzaldehyde (600 mg, 2.71 mmol) and potassium vinyltrifluoroborate (727 mg, 5.42 mmol) in 2-propanol (20 mL) was added trimethylamine (1.13 mL, 8.14 mmol). The resulting reaction mixture was degassed with nitrogen followed by [1,1-Bis(diphenylphosphino)ferrocene] dichloropalladium(II).DCM (221 mg, 0.271 mmol) addition. The resulting reaction mixture was stirred at 80° C. for 12 hrs. Reaction mixture was filtered through a celite pad, washed with diethylether (50 mL), filtrate was concentrated under reduced pressure and purification of the crude product by silica flash chromatography (0→5%) ethyl acetate in hexane afforded the title compound 3,5-difluoro-2-vinylbenzaldehyde (400 mg) as a yellow liquid.

$^1$H NMR (300 MHz, Chloroform-d) δ 10.21 (d, J=2.8 Hz, 1H), 7.43 (dd, J=8.3-2.7, 1H), 7.13-6.88 (m, 2H), 5.82 (dd, J=11.4, 1.1 Hz, 1H), 5.58 (dt, J=17.6, 1.1 Hz, 1H).

Step 2: (2-ethyl-3,5-difluorophenyl)methanol

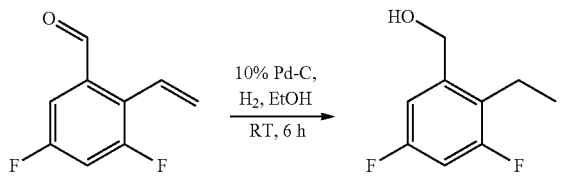

To a solution of 3,5-difluoro-2-vinylbenzaldehyde (from step 1, 400 mg, 2.37 mmol) in ethanol (10 mL) was added 10% Pd—C (80 mg). The resulting reaction mixture was stirred at room temperature for 6 hrs under hydrogen atmosphere. The reaction mixture was filtered through a celite pad and washed with ethyl acetate (30 mL). The filtrate was concentrated under reduced pressure and purification of the crude product by silica flash chromatography (0→30%) ethyl acetate in petroleum ether afforded the title compound (2-ethyl-3,5-difluorophenyl)methanol (300 mg) as a colorless liquid.

$^1$H NMR (400 MHz, Chloroform-d) δ 7.05-6.92 (m, 1H), 6.79-6.67 (m, 1H), 4.73 (d, J=5.8 Hz, 2H), 2.64 (q, J=7.1 Hz, 2H), 1.69 (t, J=6.0 Hz, 1H), 1.15 (t, J=7.1 Hz, 3H).

Step 3: 2-ethyl-3,5-difluorobenzaldehyde

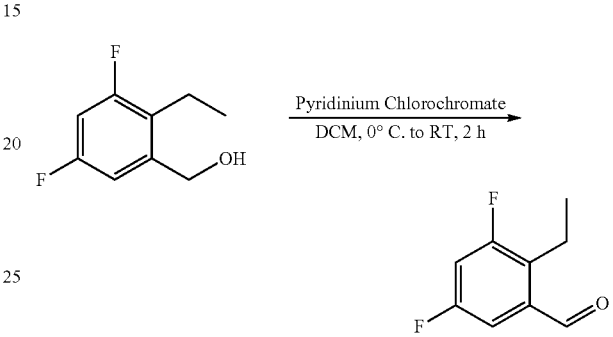

To a solution of (2-ethyl-3,5-difluorophenyl)methanol (from step 2, 300 mg, 1.74 mmol) in dichloromethane (15 mL) was added pyridinium chlorochromate (751 mg, 3.48 mmol) in one portion at 0° C. The resulting reaction mixture was stirred at room temperature for 2 hrs. Reaction mixture was diluted with dichloromethane (30 mL), filtered on a celite pad, washed with dichloromethane (20 mL). Filtrate was concentrated under reduced pressure which afforded the title compound as a brown liquid 2-ethyl-3,5-difluorobenzaldehyde (250 mg). The crude product was taken as such to next step without further purification.

Step 4: 3-ethyl 5-methyl 2-(acetoxymethyl)-4-(2-ethyl-3,5-difluorophenyl)-6-methyl-1,4-dihydropyridine-3,5-dicarboxylate

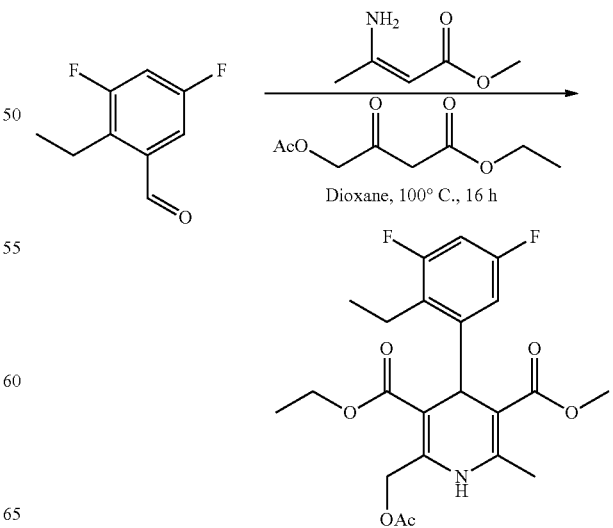

To a solution of 2-ethyl-3,5-difluorobenzaldehyde (from step 3, 250 mg, 1.46 mmol) in dioxane (15 mL) was added methyl (Z)-3-aminobut-2-enoate (169.54 mg, 1.46 mmol) and ethyl 4-acetoxy-3-oxobutanoate (Intermediate A, 276.47 mg, 1.46 mmol). The resulting reaction mixture was stirred at 100° C. for 16 hrs. Reaction mixture was cooled to room temperature, added to water and extracted with ethyl acetate. The organic phase was washed with water, brine, dried with Na$_2$SO$_4$, filtered and concentrated under reduced pressure to afford title compound 3-ethyl 5-methyl 2-(acetoxymethyl)-4-(2-ethyl-3,5-difluorophenyl)-6-methyl-1,4-dihydropyridine-3,5-dicarboxylate (250 mg) as a brown liquid. The crude product was taken as such to next step without further purification.

LCMS Rt=1.838 min; MS m/z 438.3 [M+H]$^+$; [Method 8]

Step 5: methyl 4-(2-ethyl-3,5-difluorophenyl)-2-methyl-5-oxo-1,4,5,7-tetrahydrofuro[3,4-b]pyridine-3-carboxylate

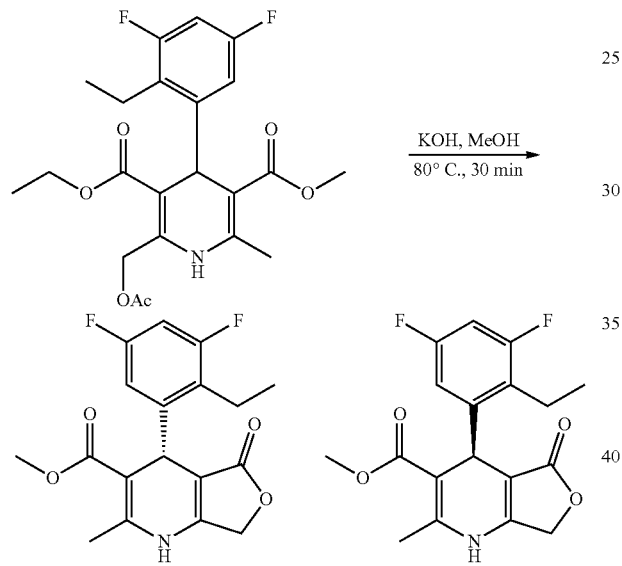

Methyl 4-(2-ethyl-3,5-difluorophenyl)-2-methyl-5-oxo-1,4,5,7-tetrahydrofuro[3,4-b]pyridine-3-carboxylate was synthesized using procedure from example 3, step 6 (using intermediate from step 4, 350 mg, 0.80 mmol). Crude product was purified by silica flash chromatography (0→70%) ethyl acetate in petroleum ether affording the title compound methyl 4-(2-ethyl-3,5-difluorophenyl)-2-methyl-5-oxo-1,4,5,7-tetrahydrofuro[3,4-b]pyridine-3-carboxylate (80 mg) as an off white solid.

LCMS Rt=1.536 min; MS m/z 350.3 [M+H]+; [Method 7]

Racemic was separated into its individual enantiomers using chiral HPLC [Method 4]

Example 12

27.8 mg of first eluting enantiomer as a white solid, (34%)
Chiral HPLC Rt=5.00 min (Mobile Phase: A=n-HEXANE, B=ETHANOL (1:1); 1 mL/min; Isocratic: 70:30 (A:B); Column: Lux, Cellulose-4 (250×4.6 mm, 5 micron).

LCMS Rt=1.536 min; MS m/z 350.3 [M+H]+; [Method 7]

$^1$H NMR (400 MHz, DMSO-d6) δ 9.95 (s, 1H), 6.97 (dd, J=11.2, 8.9 Hz, 1H), 6.71 (dt, J=9.8, 1.8 Hz, 1H), 4.98 (s, 1H), 4.83 (q, J=16.1 Hz, 2H), 3.44 (s, 3H), 3.00 (dd, J=14.3, 7.6 Hz, 1H), 2.77 (dd, J=14.6, 7.4 Hz, 1H), 2.32 (s, 3H), 1.20 (q, J=8.0 Hz, 3H).

Example 12b 28.3 mg of second eluting enantiomer as a white solid, (35%)

Chiral HPLC Rt=5.601 min (Mobile Phase: A=n-HEXANE, B=ETHANOL (1:1); 1 mL/min; Isocratic: 70:30 (A:B); Column: Lux, Cellulose-4 (250×4.6 mm, 5 micron).

LCMS Rt=1.534 min; MS m/z 350.3 [M+H]+; [Method 7]

$^1$H NMR (400 MHz, DMSO-d6) δ 9.95 (s, 1H), 6.97 (dd, J=11.2, 8.9, Hz, 1H), 6.71 (dt, J=9.8, 1.8 Hz, 1H), 4.98 (s, 1H), 4.83 (q, J=16.1 Hz, 2H), 3.44 (s, 3H), 3.00 (dd, J=14.3, 7.6 Hz, 1H), 2.77 (dd, J=14.6, 7.4 Hz, 1H), 2.32 (s, 3H), 1.20 (q, J=8.0 Hz, 3H).

Example 13. Methyl (S)-4-(2-ethyl-3-fluorophenyl)-2-methyl-5-oxo-1,4,5,7-tetrahydrofuro[3,4-b]pyridine-3-carboxylate

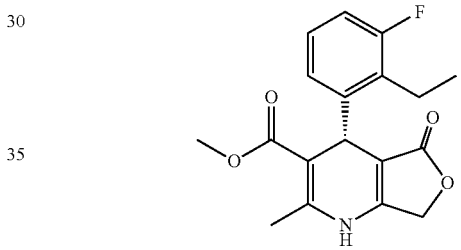

Step 1: 3-fluoro-2-vinylbenzaldehyde

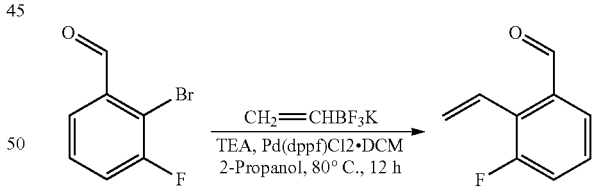

To a solution of commercially available 2-bromo-3-fluorobenzaldehyde (800 mg, 3.94 mmol) and potassium vinyltrifluoroborate (1.055 g, 7.88 mmol) in 2-propanol (25 mL) was added trimethylamine (1.64 mL, 11.82 mmol). The resulting reaction mixture was degassed with a nitrogen then [1,1-Bis(diphenylphosphino)ferrocene] dichloropalladium (II).DCM (321 mg, 0.394 mmol) was added. The resulting reaction mixture was stirred at 80° C. for 12 hrs. Reaction mixture was filtered on a celite pad, washed with diethylether (50 mL), filtrate was concentrated under reduced pressure and purification of the crude product by silica flash chromatography (0→5%) ethyl acetate in hexane afforded the title compound 3-fluoro-2-vinylbenzaldehyde (500 mg) as a yellow liquid.

¹H NMR (400 MHz, Chloroform-d) δ 10.23 (s, 1H), 7.69 (d, J=7.7 Hz, 1H), 7.39 (m, 1H), 7.30 (m, 1H), 7.09 (d, J=17.7 Hz, 1H), 5.81 (m, 1H), 5.64 (d, J=17.7 Hz, 1H).

Step 2: (2-ethyl-3-fluorophenyl) methanol

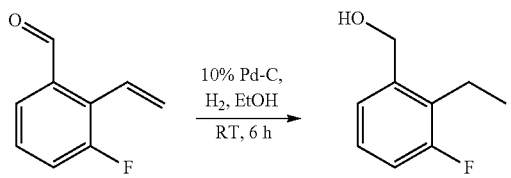

To a solution of 3-fluoro-2-vinylbenzaldehyde (from step 1, 500 mg, 3.33 mmol) in ethanol (10 mL) was added 10% Pd—C (100 mg). The resulting reaction mixture was stirred at room temperature for 6 hrs under hydrogen atmosphere. The reaction mixture was filtered on a celite pad and washed with ethyl acetate (30 mL). The filtrate was concentrated under reduced pressure and purification of the crude product by silica flash chromatography (0→30%) ethyl acetate in petroleum ether afforded the title compound (2-ethyl-3-fluorophenyl) methanol (400 mg) as a colorless liquid.

¹H NMR (300 MHz, Chloroform-d) δ 7.20-7.14 (m, 2H), 7.04-6.94 (m, 1H), 4.72 (s, 2H), 2.64 (q, J=7.1 Hz, 2H), 1.67 (brs, 1H), 1.15 (t, J=7.1 Hz, 3H).

Step 3: 2-ethyl-3-fluorobenzaldehyde

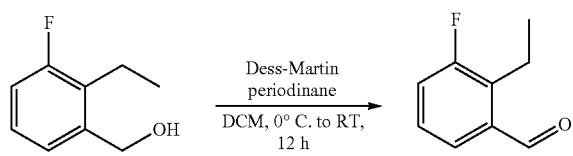

To a solution of (2-ethyl-3-fluorophenyl) methanol (from step 2, 400 mg, 2.59 mmol) in dichloromethane (15 mL) was added Des-Martin periodinane (1.65 g, 3.89 mmol) in one portion at 0° C. The resulting reaction mixture was stirred at room temperature for 12 hrs. Reaction mixture was diluted with dichloromethane (20 mL), filtered on a celite pad, washed with dichloromethane (20 mL). The filtrate was concentrated under reduced pressure and purification of the crude product by silica flash chromatography (0→10%) ethyl acetate in petroleum ether afforded the title compound 2-ethyl-3-fluorobenzaldehyde (150 mg) as a colorless liquid.

¹H NMR (300 MHz, Chloroform-d) δ 10.22 (s, 1H), 7.63 (d, J=7.3 Hz, 1H), 7.38-7.22 (m, 2H), 3.10 (q, J=7.1 Hz, 2H), 1.22 (t, J=7.1 Hz, 3H).

Step 4: 3-ethyl 5-methyl 2-(acetoxymethyl)-4-(2-ethyl-3-fluorophenyl)-6-methyl-1,4-dihydropyridine-3,5-dicarboxylate

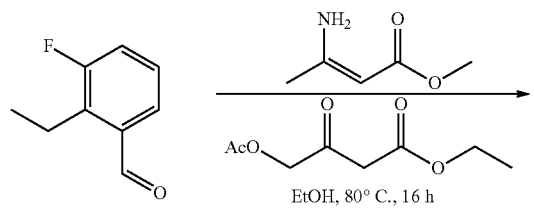

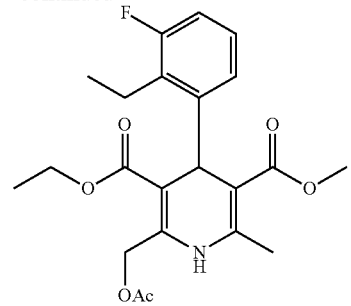

3-ethyl 5-methyl 2-(acetoxymethyl)-4-(2-ethyl-3-fluorophenyl)-6-methyl-1,4-dihydropyridine-3,5-dicarboxylate was synthesized using step 1 of general method II (using the aldehyde from step 3, 140 mg, 0.92 mmol) to give (160 mg, crude).

LCMS Rt=1.758 min; MS m/z 420.1 [M+H]+; [Method 7]

Step 5: methyl 4-(2-ethyl-3-fluorophenyl)-2-methyl-5-oxo-1,4,5,7-tetrahydrofuro[3,4-b]pyridine-3-carboxylate

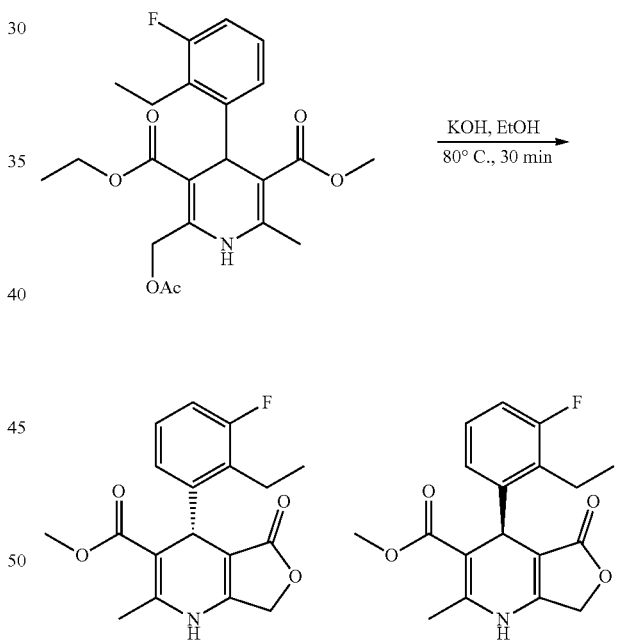

Methyl 4-(2-ethyl-3-fluorophenyl)-2-methyl-5-oxo-1,4,5,7-tetrahydrofuro[3,4-b]pyridine-3-carboxylate was synthesized using procedure from example 3, step 6 (using the intermediate from step 4, 160 mg, 0.38 mmol). Crude product by prep-HPLC [method 4] afforded the title compound methyl 4-(2-ethyl-3-fluorophenyl)-2-methyl-5-oxo-1,4,5,7-tetrahydrofuro[3,4-b]pyridine-3-carboxylate (50 mg) as an off white solid.

LCMS Rt=1.463 min; MS m/z 332.1 [M+H]+; [Method 7]

Racemic was separated into its individual enantiomers using chiral HPLC [Method 4]

Example 13

19.2 mg of first eluting enantiomer as a white solid, (38%)
Chiral HPLC Rt=6.025 min (Mobile Phase: A=n-HEXANE, B=ETHANOL (1:1); 1 mL/min; Isocratic: 70:30 (A:B); Column: Lux, 5 micron, Cellulose-4 (250×4.6 mm, 5 micron).
LCMS Rt=1.457 min; MS m/z 332.2 [M+H]+; [Method 7]
$^1$H NMR (400 MHz, DMSO-d6) δ 9.85 (s, 1H), 7.14 (d, J=8.0, 1H), 6.98-6.87 (m, 2H), 4.95 (s, 1H), 4.89-4.75 (m, 2H), 3.43 (s, 3H), 3.09-2.91 (m, 1H), 2.87-2.74 (m, 1H), 2.31 (s, 3H), 1.21 (t, J=7.5 Hz, 3H).

Example 13b 20.3 mg of second eluting enantiomer as a white solid, (40%)
Chiral HPLC Rt=6.792 min (Mobile Phase: A=n-HEXANE, B=ETHANOL (1:1); 1 mL/min; Isocratic: 70:30 (A:B); Column: Lux, 5 micron, Cellulose-4 (250×4.6 mm, 5 micron).
LCMS Rt=1.463 min; MS m/z 332.0 [M+H]+; [Method 7]
$^1$H NMR (400 MHz, DMSO-d6) δ 9.85 (s, 1H), 7.14 (d, J=8.0, 1H), 6.98-6.87 (m, 2H), 4.95 (s, 1H), 4.89-4.75 (m, 2H), 3.43 (s, 3H), 3.09-2.91 (m, 1H), 2.87-2.74 (m, 1H), 2.31 (s, 3H), 1.21 (t, J=7.5 Hz, 3H).

Example 14. (S)-methyl 4-(2-cyclopropyl-3,5-difluorophenyl)-2-methyl-5-oxo-1,4,5,7-tetrahydrofuro[3,4-b]pyridine-3-carboxylate

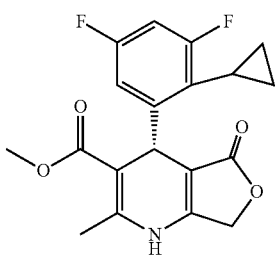 [SMILES: COC(=O)C1=C(C)NC2=C(C(=O)OC2)[C@H]1c1cc(F)cc(F)c1C1CC1]

Step 1: 2-cyclopropyl-3,5-difluorobenzaldehyde

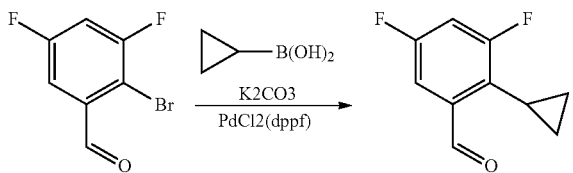

To a mixture of 2-bromo-3,5-difluorobenzaldehyde (13 g, 58.8 mmol) and cyclopropylboronic acid (6.06 g, 70.6 mmol) in dioxane (60 mL) was added K$_2$CO$_3$ (2N solution) (58.8 mL, 118 mmol) and PdCl$_2$(dppf). CH$_2$Cl$_2$ adduct (4.8 g, 5.88 mmol). The reaction mixture was stirred at 70° C. for 3 h. The reaction mixture was filtered over a celite pad. Water (75 mL) was added and product extracted with ethyl acetate (2×100 ml). Ethyl acetate phases were combined, washed with brine and dried over MgSO$_4$. The solvent was removed under reduced pressure and purification by automated flash column chromatography (0→50%) ethyl acetate in heptane afforded the title compound 2-cyclopropyl-3,5-difluorobenzaldehyde (7.2 g) as a colorless liquid.
LCMS Rt=0.99 min; [Method 2]
$^1$H NMR (400 MHz, Chloroform-d) δ 10.68 (s, 1H), 7.38-7.26 (m, 1H), 6.91 (ddd, J=10.6, 8.1, 2.8 Hz, 1H), 1.96-1.83 (m, 1H), 1.29-1.08 (m, 2H), 0.69 (q, J=5.7 Hz, 2H).

Step 2: Methyl 4-(2-cyclopropyl-3,5-difluorophenyl)-2-methyl-5-oxo-1,4,5,7-tetrahydrofuro[3,4-b]pyridine-3-carboxylate

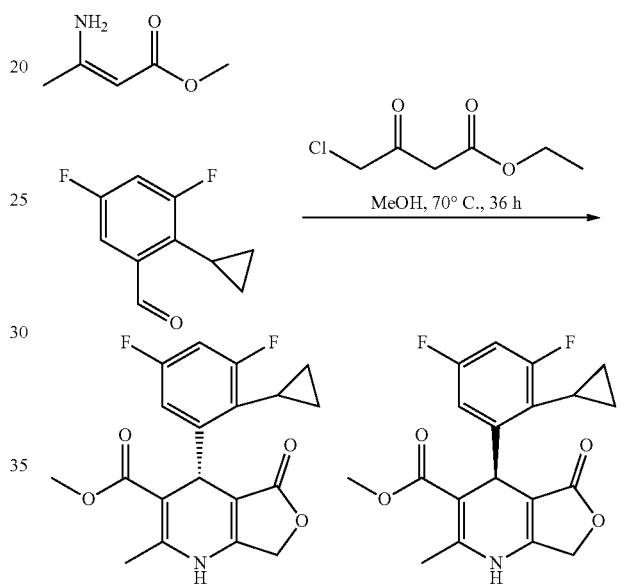

Methyl 4-(2-cyclopropyl-3,5-difluorophenyl)-2-methyl-5-oxo-1,4,5,7-tetrahydrofuro[3,4-b]pyridine-3-carboxylate was synthesized using general method I (using aldehyde from step 1, 6.5 g, 35.7 mmol). Reaction mixture was concentrated by half. Resulting solid was collected by filtration and washed with DCM/Methanol (95:5) (20 mL) and water (30 mL). 3.3 g Light yellow solid was obtained as product. Filtrate was concentrated and purification by silica flash chromatography (0→100%) ethyl acetate in heptane afforded a second batch of product (730 mg), both solids were combined to afford the title compound methyl 4-(2-(2,2-difluorocyclopropyl)-3-fluorophenyl)-2-methyl-5-oxo-1,4,5,7-tetrahydrofuro[3,4-b]pyridine-3-carboxylate as an light yellow solid.
LCMS Rt=1.01 min; MS m/z 362.2 [M+H]$^+$; [Method 2]
Racemic mixture was separated into its enantiomers using chiral SFC (Mobile Phase: 30% IPA; Column: (SS) Whelk-O1 30×250 mm).

Example 14

1.85 g of first eluting enantiomer as a light yellow solid, (27.2%)
SFC Rt=2.96 min (Whelk-O1 SS 4.6×100 mm 5 μm, 5→55% IPA in CO2 5 mL/min)
LCMS Rt=2.19 min; MS m/z 362.2 [M+H]+; [Method 4]

¹H NMR (400 MHz, DMSO-d6) δ 9.85 (s, 1H), 6.92 (ddd, J=11.4, 8.9, 2.8 Hz, 1H), 6.79-6.69 (m, 1H), 5.48 (d, J=1.9 Hz, 1H), 4.93-4.75 (m, 2H), 3.47 (d, J=2.0 Hz, 3H), 2.31 (d, J=1.5 Hz, 3H), 2.10-1.97 (m, 1H), 1.19-1.08 (m, 1H), 1.01-0.87 (m, 2H), 0.74-0.62 (m, 1H).

The stereochemistry of Example 14, methyl 2-methyl-5-oxo-4-phenyl-1,4,5,7-tetrahydrofuro[3,4-b]pyridine-3-carboxylate, was determined by single crystal x-ray crystallographic analysis and it confirmed that active enantiomer is the S-enantiomer (FIG. 2).

Example 14b 2.02 g of second eluting enantiomer as a light yellow solid, (29.8%)

SFC Rt=3.32 min (Whelk-O1 SS 4.6×100 mm 5 μm, 5→55% IPA in CO₂ 5 mL/min)

LCMS Rt=2.16 min; MS m/z 362.2 [M+H]+; [Method 4]

¹H NMR (400 MHz, DMSO-d6) δ 9.85 (s, 1H), 6.92 (ddd, J=11.4, 8.9, 2.8 Hz, 1H), 6.79-6.69 (m, 1H), 5.48 (d, J=1.9 Hz, 1H), 4.93-4.75 (m, 2H), 3.47 (d, J=2.0 Hz, 3H), 2.31 (d, J=1.5 Hz, 3H), 2.10-1.97 (m, 1H), 1.19-1.08 (m, 1H), 1.01-0.87 (m, 2H), 0.74-0.62 (m, 1H).

Example 15. (S)-methyl 4-(3-fluoro-2-isopropylphenyl)-2-methyl-5-oxo-1,4,5,7-tetrahydrofuro[3,4-b]pyridine-3-carboxylate

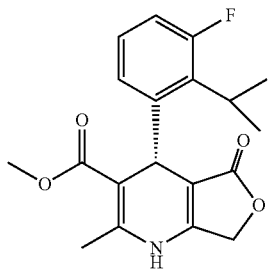 [SMILES: COC(=O)C1=C(C)NC2=C(C(=O)OC2)[C@H]1c1cccc(F)c1C(C)C]

Step 1: (S)-methyl 4-(2-bromo-3-fluorophenyl)-2-methyl-5-oxo-1,4,5,7-tetrahydrofuro[3,4-b]pyridine-3-carboxylate

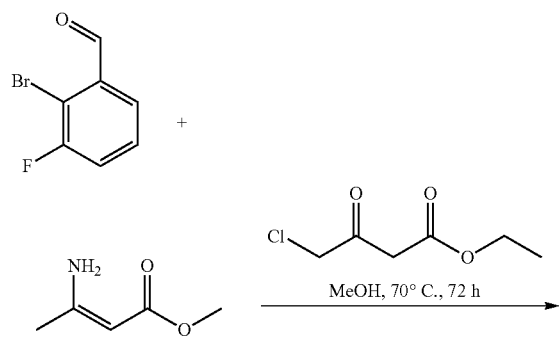

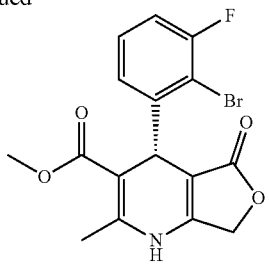

Racemic methyl (S)-methyl 4-(2-bromo-3-fluorophenyl)-2-methyl-5-oxo-1,4,5,7-tetrahydrofuro[3,4-b]pyridine-3-carboxylate was synthesized using general procedure I using commercially available 2-bromo-3-fluorobenzaldehyde (15 g, 73.9 mmol). The resulting solid in the reaction mixture was collected by filtration and dried to give 9 g of yellow solid (31.9%). Racemic was separated into its enantiomers using chiral SFC Column: SS Whelk-O1 30×250 mm; Flow Rate: 80 g per minute; Cosolvent: 40% MeOH; Detection: 340 nm; BPR Set Point: 125 bar.

To give 4.12 g of first eluting enantiomer as a pale yellow solid (27.7%)

SFC Rt=2.93 min; SS Whelk 01; 5-55% MeOH in CO₂ 5 mL/min

LCMS Rt=1.79 min; MS m/z 382.0 [M+0]+; [Method 3]

¹H NMR (400 MHz, DMSO-d6) δ 9.90 (s, 1H), 7.34 (td, J=8.1, 5.7 Hz, 1H), 7.23-7.01 (m, 2H), 5.22 (s, 1H), 4.83 (d, J=2.1 Hz, 2H), 3.42 (s, 3H), 2.31 (s, 3H).

Step 2: (S)-methyl 4-(3-fluoro-2-(prop-1-en-2-yl)phenyl)-2-methyl-5-oxo-1,4,5,7-tetrahydrofuro[3,4-b]pyridine-3-carboxylate

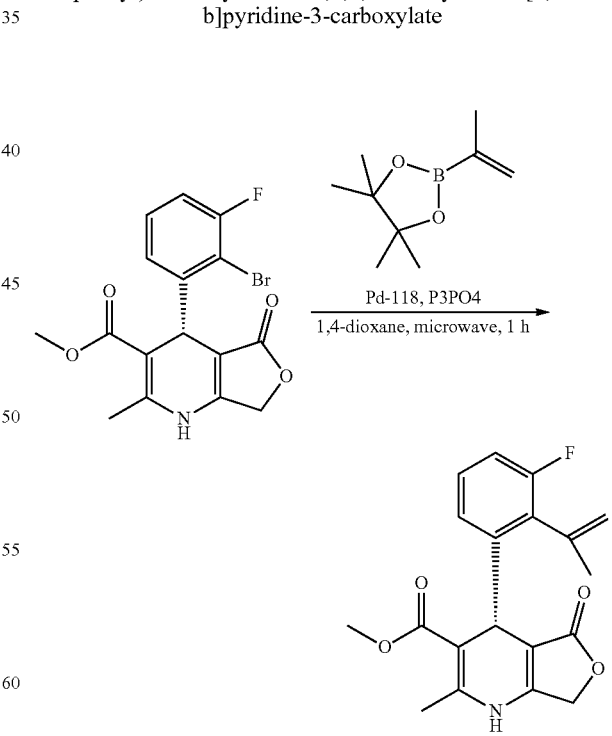

A round bottom flask equipped with a magnetic stirbar is charged with (S)-methyl 4-(2-bromo-3-fluorophenyl)-2-methyl-5-oxo-1,4,5,7-tetrahydrofuro[3,4-b]pyridine-3-carboxylate (from step 1, 2000 mg, 5.23 mmol), isopropenylboronic acid pinacol ester (1.553 mL, 7.85 mmol), dioxane (26.2 mL), 2 M aqueous potassium phosphate tribasic (5.23 mL, 10.47 mmol), and Pd-118 (171 mg, 0.262 mmol). The vial is sealed and flushed with nitrogen, then microwaved at 100° C. for 1 hour. The reaction mixture is diluted with water and extracted with EtOAc (4×20 mL). Combined organic extracts are washed with brine, dried over sodium sulfate. Solvent is evaporated under reduced pressure. Purification of the crude product by silica flash column chromatography (0→75% ethyl acetate in heptane) afforded the title compound (S)-methyl 4-(3-fluoro-2-(prop-1-en-2-yl)phenyl)-2-methyl-5-oxo-1,4,5,7-tetrahydrofuro[3,4-b]pyridine-3-carboxylate (1.34 g, 64.9%) as a pale yellow solid.

LCMS Rt=2.06 min; MS m/z 344.2 [M+H]+; [Method 4]
¹H NMR (400 MHz, DMSO-d6) δ 9.79 (s, 1H), 7.23 (td, J=7.9, 5.9 Hz, 1H), 7.05 (dd, J=7.9, 1.4 Hz, 1H), 6.99-6.93 (m, 1H), 5.43 (s, 1H), 5.40-5.37 (m, 1H), 5.04 (s, 1H), 4.81 (d, J=5.4 Hz, 2H), 3.47 (s, 3H), 2.23 (s, 3H), 2.07 (s, 3H).

Step 3: (S)-methyl 4-(3-fluoro-2-isopropylphenyl)-2-methyl-5-oxo-1,4,5,7-tetrahydrofuro[3,4-b]pyridine-3-carboxylate

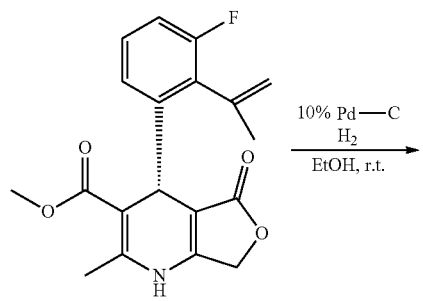

A reaction vial equipped with a magnetic stir bar is charged with (S)-methyl 4-(3-fluoro-2-(prop-1-en-2-yl)phenyl)-2-methyl-5-oxo-1,4,5,7-tetrahydrofuro[3,4-b]pyridine-3-carboxylate (from step 2, 300 mg, 0.874 mmol), palladium on carbon (93 mg, 0.874 mmol), and EtOH (3 mL). The vial is sealed and fitted with a balloon of hydrogen (1.761 mg, 0.874 mmol). The vial is evacuated and backfilled with hydrogen and allowed to stir at room temperature for 24 hours. Reaction mixture is diluted with methanol and filtered through a pad of celite. The filter is rinsed with 100 mL of methanol. The collected filtrate is concentrated by under reduced pressure. Purification of the crude product by silica flash column chromatography (0→100% ethyl acetate in heptane) afforded the title compound (S)-methyl 4-(3-fluoro-2-isopropylphenyl)-2-methyl-5-oxo-1,4,5,7-tetrahydrofuro[3,4-b]pyridine-3-carboxylate as an off-white solid (141.5 mg, 44.5%).

Example 15

LCMS Rt=2.26 min; MS m/z 346.2 [M+H]+; [Method 4]
¹H NMR (400 MHz, DMSO-d6) δ 9.81 (s, 1H), 7.13 (td, J=8.0, 5.6 Hz, 1H), 6.97-6.92 (m, 1H), 6.88 (ddd, J=12.6, 8.0, 1.3 Hz, 1H), 5.06 (s, 1H), 4.81 (d, J=4.9 Hz, 2H), 3.67 (p, J=7.3 Hz, 1H), 3.45 (s, 3H), 2.31 (s, 3H), 1.34 (ddd, J=25.8, 7.0, 1.7 Hz, 6H).

Example 16. (S)-methyl 4-(3-fluoro-2-(3,3,3-trifluoroprop-1-en-2-yl)phenyl)-2-methyl-5-oxo-1,4,5,7-tetrahydrofuro[3,4-b]pyridine-3-carboxylate

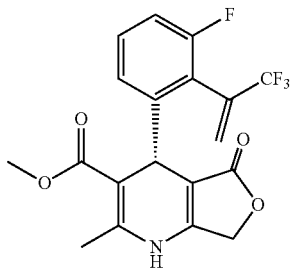 [SMILES: C=C(c1c(F)cccc1[C@H]1C(C(=O)OC)=C(C)NC2=C1C(=O)OC2)C(F)(F)F]

Step 1: (S)-methyl 4-(3-fluoro-2-(3,3,3-trifluoroprop-1-en-2-yl)phenyl)-2-methyl-5-oxo-1,4,5,7-tetrahydrofuro[3,4-b]pyridine-3-carboxylate

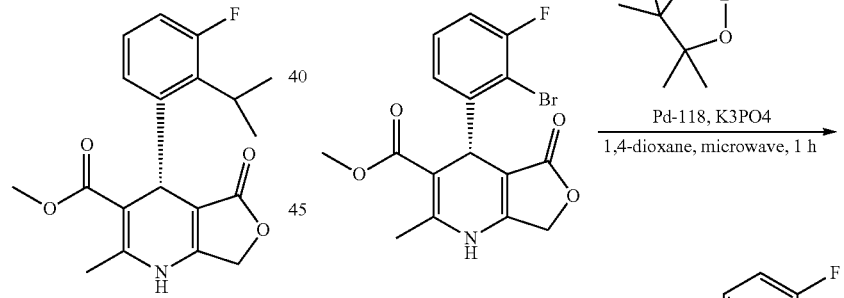

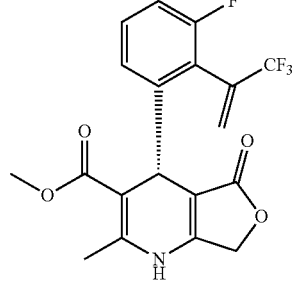

A microwave reaction vial is charged with (S)-methyl 4-(2-bromo-3-fluorophenyl)-2-methyl-5-oxo-1,4,5,7-tetrahydrofuro[3,4-b]pyridine-3-carboxylate (intermediate from step 1, example 15, 215 mg, 0.563 mmol), 4,4,5,5-tetramethyl-2-(3,3,3-trifluoroprop-1-en-2-yl)-1,3,2-dioxaborolane (125 mg, 0.563 mmol), 1,4-dioxane (2 mL), 2M aqueous potassium phosphate tribasic (0.563 mL, 1.126 mmol), and Pd-118 (36.7 mg, 0.056 mmol). The vial is sealed and flushed with nitrogen, then heated to 120° C. in a Biotage microwave reactor for 3 hours. The reaction mixture is then diluted with water and extracted with EtOAc (3×10 mL). The combined organic extracts were washed with brine, dried over sodium sulfate, filtered, and concentrated by under reduced pressure. Purification of the crude product by HPLC chromatography (Column: X-bridge 30×50 mm 5 μm; MeCN/H$_2$O w/ 5 mM NH$_4$OH; 75 mL/min; 1.5 mL injection volume) followed by freeze drying afforded the title compound (S)-methyl 4-(3-fluoro-2-(3,3,3-trifluoro-prop-1-en-2-yl)phenyl)-2-methyl-5-oxo-1,4,5,7-tetrahydro-furo[3,4-b]pyridine-3-carboxylate as a white powder (14.2 mg, 5.7%).

Example 16

LCMS Rt=2.15 min; MS m/z 398.2 [M+H]+; [Method 4]
$^1$H NMR (400 MHz, DMSO-d6) δ 9.88 (d, J=24.3 Hz, 1H), 7.42 (td, J=8.1, 5.9 Hz, 1H), 7.18 (d, J=7.9 Hz, 1H), 7.10 (ddd, J=9.7, 8.1, 1.4 Hz, 1H), 6.82 (s, 1H), 6.47 (s, 1H), 4.92 (s, 1H), 4.86 (d, J=3.2 Hz, 2H), 3.37 (s, 3H), 2.25 (s, 3H).

Example 17. (S)-methyl 4-(2-(2,2-difluoroethyl)-3-fluorophenyl)-2-methyl-5-oxo-1,4,5,7-tetrahydrofuro[3,4-b]pyridine-3-carboxylate

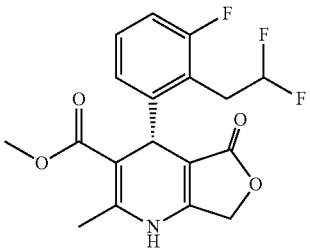 [SMILES: COC(=O)C1=C(C)NC2=C(C(=O)OC2)[C@H]1c1cccc(F)c1CC(F)F]

Step 1: Methyl (S)-4-(3-fluoro-2-(2-oxoethyl)phenyl)-2-methyl-5-oxo-1,4,5,7-tetrahydrofuro[3,4-b]pyridine-3-carboxylate

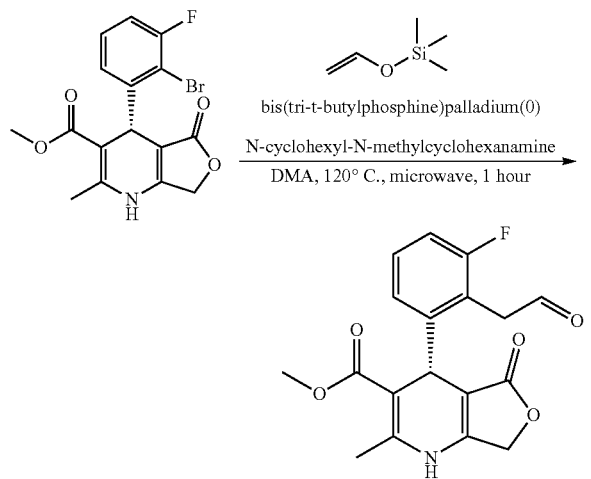

A microwave reaction vial is charged with (S)-methyl 4-(2-bromo-3-fluorophenyl)-2-methyl-5-oxo-1,4,5,7-tetrahydrofuro[3,4-b]pyridine-3-carboxylate (intermediate from step 1, example 15, 100 mg, 0.262 mmol), vinyloxy-trimethylsilane (0.060 mL, 0.392 mmol), DMA (2.5 mL), N-cyclohexyl-N-methylcyclohexanamine (0.086 mL, 0.392 mmol), and bis(tri-t-butylphosphine)palladium(0) (6.69 mg, 0.013 mmol). The vial is sealed and flushed with nitrogen then heated to 120° C. in a Biotage microwave reactor for one hour. Reaction mixture is diluted with water and extracted with EtOAc (3×15 mL). Combined organic extracts were washed with brine, dried over sodium sulfate and concentrated under reduced pressure. Purification of the crude product by silica flash column chromatography (0→100% ethyl acetate in heptane) afforded the title compound methyl (S)-4-(3-fluoro-2-(2-oxoethyl)phenyl)-2-methyl-5-oxo-1,4,5,7-tetrahydrofuro[3,4-b]pyridine-3-carboxylate as a yellow solid (95.1 mg, 105%).

LCMS Rt=0.76 min; MS m/z 346.3 [M+H]+; [Method 2]
$^1$H NMR (400 MHz, DMSO-d6) δ 9.87 (s, 1H), 9.67 (d, J=1.9 Hz, 1H), 7.30 (td, J=8.0, 6.1 Hz, 1H), 7.07-7.00 (m, 2H), 4.92 (s, 1H), 4.82 (d, J=3.2 Hz, 2H), 4.14 (dt, J=17.6, 2.5 Hz, 1H), 3.93 (dt, J=17.4, 1.8 Hz, 1H), 3.37 (s, 3H), 2.33 (s, 3H).

Step 2: (S)-methyl 4-(2-(2,2-difluoroethyl)-3-fluorophenyl)-2-methyl-5-oxo-1,4,5,7-tetrahydrofuro[3,4-b]pyridine-3-carboxylate

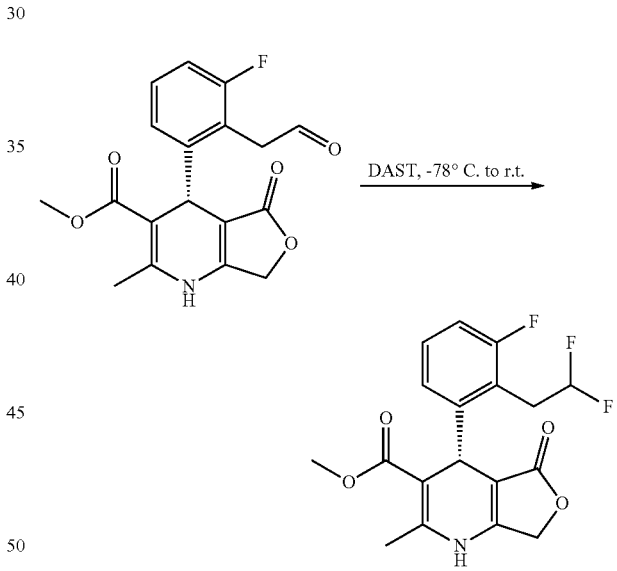

A reaction vial is charged with methyl (S)-4-(3-fluoro-2-(2-oxoethyl)phenyl)-2-methyl-5-oxo-1,4,5,7-tetrahydrofuro[3,4-b]pyridine-3-carboxylate (95.1 mg, 0.275 mmol) and DCM (2.5 mL), then cooled to −78° C. DAST (0.073 mL, 0.551 mmol) is carefully added to the reaction mixture dropwise. The reaction mixture is stirred for one hour at −78° C. then the cooling bath is removed and the mixture stirred for three hours at room temperature. After the reaction time has elapsed, the reaction mixture is cooled to 0° C. and water is added dropwise to the mixture. Product is extracted with DCM (3×10 mL). Combined organic extracts were washed with brine, dried over sodium sulfate, and concentrated by under reduced pressure. Purification of the crude product by prep HPLC chromatography (Column: Xbridge C18 OBD 30×50 mm 5 μm column; Mobile Phase:

MeCN/H₂O w/ 5 mM NH₄OH; 75 mL/min; 1.5 mL injection volume) followed by freeze drying afforded the title compound (S)-methyl 4-(2-(2,2-difluoroethyl)-3-fluorophenyl)-2-methyl-5-oxo-1,4,5,7-tetrahydrofuro[3,4-b]pyridine-3-carboxylate as a white powder (9.6 mg, 8.5%).

Example 17

LCMS Rt=2.00 min; MS m/z 368.2 [M+H]+; [Method 4]
¹H NMR (400 MHz, Methanol-d4) δ 7.14 (td, J=7.9, 5.5 Hz, 1H), 6.96 (dd, J=7.8, 1.4 Hz, 1H), 6.85-6.77 (m, 1H), 6.41 (tt, J=56.2, 4.7 Hz, 1H), 4.95 (s, 1H), 4.71 (s, 2H), 3.42 (s, 3H), 3.21 (s, 2H), 2.29 (s, 3H).

Example 18. Methyl (S)-4-(3,5-difluoro-2-isopropylphenyl)-2-methyl-5-oxo-1,4,5,7-tetrahydrofuro[3,4-b]pyridine-3-carboxylate

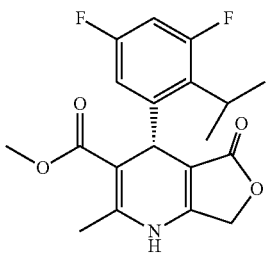 [SMILES: COC(=O)C1=C(C)NC2=C(C(=O)OC2)[C@H]1c1cc(F)cc(F)c1C(C)C]

Step 1: Methyl (S)-4-(2-bromo-3,5-difluorophenyl)-2-methyl-5-oxo-1,4,5,7-tetrahydrofuro[3,4-b]pyridine-3-carboxylate

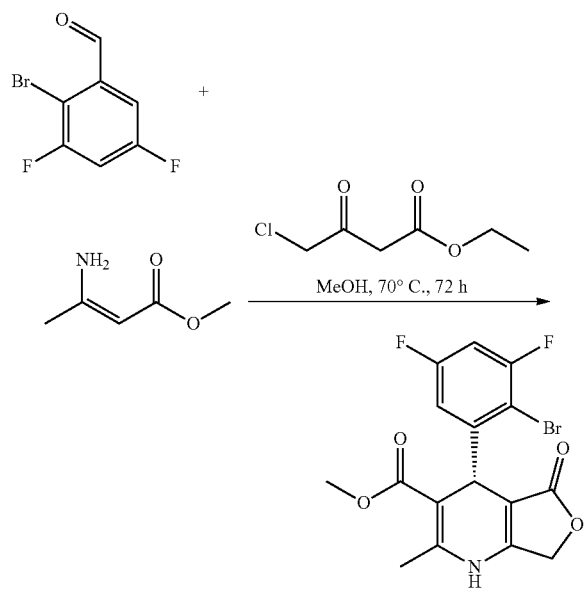

Racemic methyl (S)-4-(2-bromo-3,5-difluorophenyl)-2-methyl-5-oxo-1,4,5,7-tetrahydrofuro[3,4-b]pyridine-3-carboxylate was synthesized using General Procedure I using commercially available 2-bromo-3,5-difluorobenzaldehyde (120 g, 542.98 mmol). The resulting solid in the reaction mixture was collected by filtration and dried to give 80 g of yellow solid (36.82%). Racemic was separated into its enantiomers using chiral SFC Column: Whelk 01(S, S), 250×4.6 mm I.D., 5 μm Mobile phase: A for CO₂ and B for MEOH (0.05% DEA) Gradient: B 40%; Flow rate: 2.5 mL/min; Back pressure: 100 bar; Column temperature: 25° C.

To give 37.7 g of first eluting enantiomer as a pale yellow solid (47.1%)
SFC Rt=3.364 min; SS Whelk O1_5_MeOH_DEA_40_25 ML
LCMS Rt=1.97 min; MS m/z 400.1 [M+0]+; [Method 4]
¹H NMR (400 MHz, DMSO-d6) δ 9.95 (s, 1H), 7.28 (td, J=8.8, 2.9 Hz, 1H), 6.95 (ddd, J=9.3, 2.9, 1.5 Hz, 1H), 5.25 (s, 1H), 4.95-4.69 (m, 2H), 3.43 (s, 3H), 2.32 (s, 3H).

Step 2: Methyl (S)-4-(3,5-difluoro-2-(prop-1-en-2-yl)phenyl)-2-methyl-5-oxo-1,4,5,7-tetrahydrofuro[3,4-b]pyridine-3-carboxylate

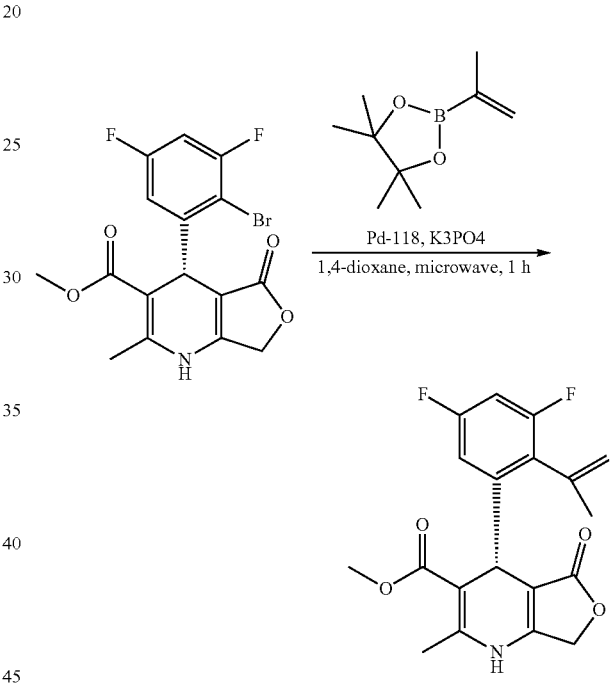

A round bottom flask equipped with a magnetic stirbar is charged with methyl (S)-4-(2-bromo-3,5-difluorophenyl)-2-methyl-5-oxo-1,4,5,7-tetrahydrofuro[3,4-b]pyridine-3-carboxylate (500 mg, 1.25 mmol), isopropenylboronic acid pinacol ester (0.433 mL, 2.19 mmol), 1,4-dioxane (6. mL), 2 M aqueous potassium phosphate tribasic (1.25 mL, 2.5 mmol), and Pd-118 (40.7 mg, 0.062 mmol). The vial is sealed and flushed with nitrogen then heated to 120° C. in a microwave reactor for 1 hour. The reaction mixture is diluted with water and extracted with EtOAc (3×15 mL). Combined organic extracts are washed with brine, dried over sodium sulfate and solvent is evaporated under reduced pressure. Purification of the crude product by silica flash column chromatography (0→100% ethyl acetate in heptane) afforded the title compound methyl (S)-4-(3,5-difluoro-2-(prop-1-en-2-yl)phenyl)-2-methyl-5-oxo-1,4,5,7-tetrahydrofuro[3,4-b]pyridine-3-carboxylate as a light brown solid (293.5 mg, 56.6%).

LCMS Rt=2.18 min; MS m/z 362.2 [M+H]+; [Method 4]
¹H NMR (400 MHz, DMSO-d6) δ 9.85 (s, 1H), 7.02 (ddd, J=11.1, 8.7, 2.6 Hz, 1H), 6.91-6.76 (m, 1H), 5.43 (s, 1H), 5.40 (s, 1H), 5.06 (s, 1H), 4.82 (q, J=16.1 Hz, 2H), 3.50 (s, 3H), 2.25 (s, 3H), 2.06 (s, 3H).

Step 3: Methyl (S)-4-(3,5-difluoro-2-isopropylphenyl)-2-methyl-5-oxo-1,4,5,7-tetrahydrofuro[3,4-b]pyridine-3-carboxylate

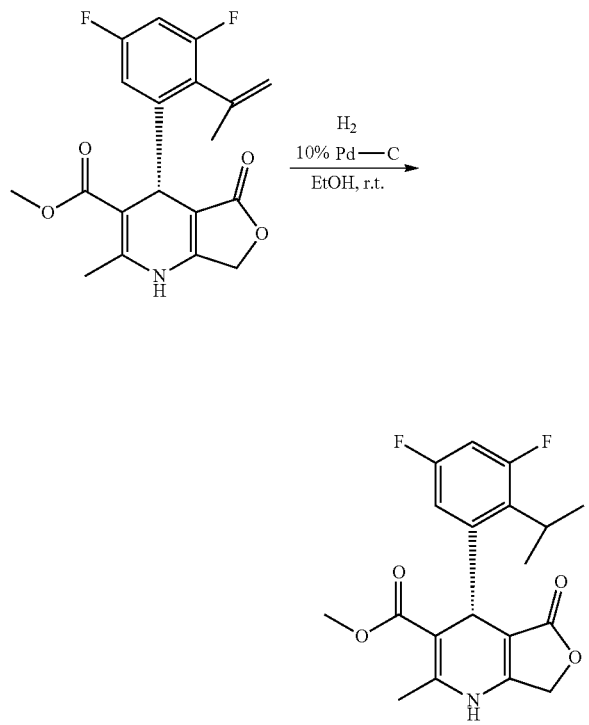

A reaction vial is charged with methyl (S)-4-(3,5-difluoro-2-(prop-1-en-2-yl)phenyl)-2-methyl-5-oxo-1,4,5,7-tetrahydrofuro[3,4-b]pyridine-3-carboxylate (100 mg, 0.277 mmol), palladium on carbon (29.5 mg, 0.277 mmol), and EtOH (3 mL). The vial is sealed and fitted with a balloon of hydrogen. The vial is evacuated and backfilled with hydrogen (3×) then allowed to stir at room temperature. After the reaction is complete, the mixture is diluted with MeOH and filtered over a pad of celite. The pad is washed with 50 mL of MeOH. The collected filtrate is concentrated under reduced pressure. Purification of the crude product by prep HPLC chromatography (Column: Xbridge C18 OBD 30×50 mm 5 μm column; Mobile Phase: MeCN/H₂O w/ 5 mM NH₄OH; 75 mL/min; 1.5 mL injection volume) followed by freeze drying afforded the title compound methyl (S)-4-(3,5-difluoro-2-isopropylphenyl)-2-methyl-5-oxo-1,4,5,7-tetrahydrofuro[3,4-b]pyridine-3-carboxylate as a white powder (22.9 mg, 21.6%).

Example 18

LCMS Rt=2.37; MS m/z 364.1 [M+H]⁺; [Method 4]

¹H NMR (400 MHz, Methanol-d4) δ 6.68-6.46 (m, 2H), 5.10 (s, 1H), 4.70 (d, J=3.1 Hz, 2H), 3.58 (pq, J=6.9, 3.0 Hz, 1H), 3.45 (s, 3H), 2.29 (s, 3H), 1.27 (ddd, J=27.5, 7.0, 1.7 Hz, 6H).

Example 19: (S)-methyl 4-(3,5-difluoro-2-(3,3,3-trifluoroprop-1-en-2-yl)phenyl)-2-methyl-5-oxo-1,4,5,7-tetrahydrofuro[3,4-b]pyridine-3-carboxylate

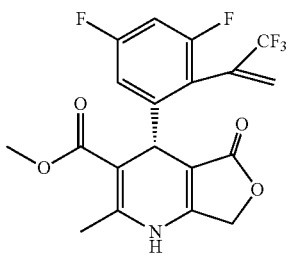 [SMILES: C=C(c1c(F)cc(F)cc1[C@H]1C(C(=O)OC)=C(C)NC2=C1C(=O)OC2)C(F)(F)F]

(S)-methyl 4-(3,5-difluoro-2-(3,3,3-trifluoroprop-1-en-2-yl)phenyl)-2-methyl-5-oxo-1,4,5,7-tetrahydrofuro[3,4-b]pyridine-3-carboxylate was prepared analogously to example 18 in step 2 using 4,4,5,5-tetramethyl-2-(3,3,3-trifluoroprop-1-en-2-yl)-1,3,2-dioxaborolane (305 mg, 1.374 mmol). Crude was purified by automated flash column chromatography, eluting with 0-100% gradient of EtOAc in heptane on a 12 g Si-column, loading with DCM and further purified by mass directed reverse phase prep chromatography; Conditions: Xbridge C18 OBD 30×50 mm 5 μm column ACN/H2O w/ 0.1% Formic Acid 75 mL/min 1.5 mL injection. To give 23 mg of the title compounds as a white solid, Yield=4%

Example 19

LCMS Rt=2.24 min; MS m/z 416.1 [M+H]+; [Method 3]

¹H NMR (400 MHz, DMSO-d6) δ 9.95 (s, 1H), 7.20 (ddd, J=10.8, 8.5, 2.6 Hz, 1H), 6.97 (dd, J=9.8, 2.6 Hz, 1H), 6.79 (s, 1H), 6.49 (s, 1H), 4.94 (s, 1H), 4.86 (d, J=9.9 Hz, 2H), 3.41 (s, 3H), 2.25 (d, J=4.1 Hz, 3H).

NOESY NMR confirms that the observed doubling of some aliphatic peaks (minor peaks at different ppms not noted above) all correlate to parent compound indicating interchangeable rotomers or atropisomers are present.

Example 20: Methyl (S)-4-(3-fluoro-2-(3-fluorocyclobutyl)phenyl)-2-methyl-5-oxo-1,4,5,7-tetrahydrofuro[3,4-b]pyridine-3-carboxylate

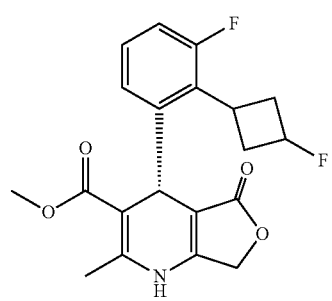 [SMILES: COC(=O)C1=C(C)NC2=C(C(=O)OC2)[C@H]1c1cccc(F)c1C1CC(F)C1]

Step 1: 3-(benzyloxy)-1-(2-bromo-6-fluorophenyl)cyclobutan-1-ol

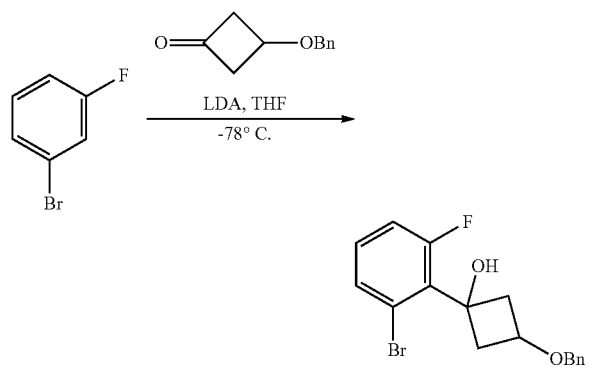

To the stirred solution of 1-bromo-3-fluorobenzene (5 g, 28.57 mmol) in THF (40 mL) at −78° C., was added LDA (2M solution in THF) (15.71 mL, 31.42 mmol) and the reaction mixture was stirred for 15 min. Then 3-oxocyclobutyl benzoate (5.03 mmol, 28.57 mmol) was added at −78° C. and the reaction mixture was stirred for 2 h. The reaction was monitored by TLC. The reaction mass was quenched with saturated NH$_4$Cl solution and extracted with ethyl acetate. The combined organic layers were dried over anhydrous sodium sulfate, filtered, and concentrated under reduced pressure to afford the crude. Crude compound was purified by silica flash chromatography (50%) ethyl acetate in hexane to afford the title compound 3-(benzyloxy)-1-(2-bromo-6-fluorophenyl)cyclobutan-1-ol (5.5 g, 55%) as a light brown liquid.

$^1$H NMR (600 MHz, CDCl$_3$) δ 7.40-7.32 (m, 5H), 7.31-7.30 (m, 1H), 7.13-7.09 (m, 1H), 7.01 (t, J=9.6 Hz, 1H), 4.56 (s, 2H), 4.13-4.09 (m, 1H), 3.31 (s, 1H), 3.09-3.06 (m, 2H), 2.77-2.74 (m, 2H) (no OH proton seen)

Step 2: 2-(3-(benzyloxy)cyclobutyl)-1-bromo-3-fluorobenzene

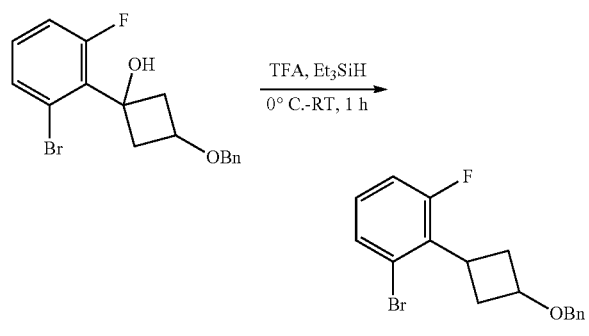

To a cooled stirring solution of 3-(benzyloxy)-1-(2-bromo-6-fluorophenyl)cyclobutan-1-ol (step 1, 5.5 g, 15.66 mmol) in TFA (6.0 mL, 78.3 mmol) at 0° C. was added Et$_3$SiH (5.0 mL, 31.32 mmol). The resulting reaction mixture was allowed to warm to RT and stirred for 1 h. Water was added to the reaction mixture and product extracted with DCM. The combined organic layers were combined, washed with saturated NaHCO$_3$ solution, water, brine, dried over anhydrous Na$_2$SO$_4$, filtered and concentrated under reduced pressure to afforded crude compound. The crude product was purified by silica flash chromatography (10%) ethyl acetate in hexane to afford the title compound 2-(3-(benzyloxy)cyclobutyl)-1-bromo-3-fluorobenzene (3.9 g, 74%) as a light brown liquid.

$^1$H NMR (300 MHz, CDCl$_3$) δ 7.41-7.27 (m, 6H), 7.06-6.94 (m, 2H), 4.49 (s, 2H), 4.03-3.98 (m, 1H), 3.37-3.27 (m, 1H), 2.82-2.66 (m, 2H), 2.62-2.45 (m, 2H)

Step 3: 2-(3-(benzyloxy)cyclobutyl)-1-fluoro-3-vinylbenzene

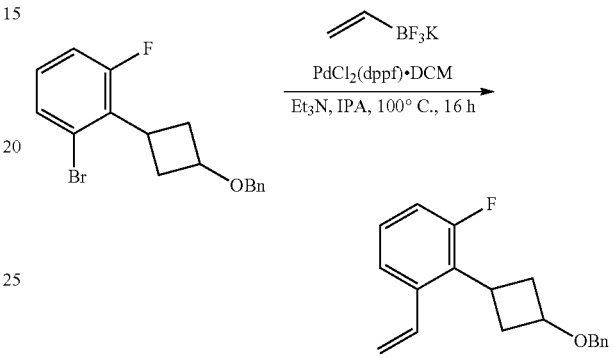

To a stirred solution of 2-(3-(benzyloxy)cyclobutyl)-1-bromo-3-fluorobenzene (step 2, 3.4 g, 10.14 mmol) in IPA (50 mL), was added potassium vinyltrifluoroborate (2.71 g, 20.28 mmol) followed by Et$_3$N (4.28 mL, 30.42 mmol) and flask purged argon gas for 10 minutes. Pd(dppf)Cl$_2$.DCM (0.827 g, 1.014 mmol) was added and again purged argon gas for another 5 minutes. Reaction mixture was heated to 100° C. and stirred for 16 h. Reaction mixture was filtered over celite and celite bed washed with EtOAc. The filtrate was concentrated under reduced pressure. The crude product was purified by silica flash chromatography (10%) ethyl acetate in hexane to afford the title compound 2-(3-(benzyloxy)cyclobutyl)-1-fluoro-3-vinylbenzene (1.7 g, 59%) as a light brown liquid.

$^1$H NMR (400 MHz, CDCl$_3$) δ 7.38-7.28 (m, 5H), 7.21-7.04 (m, 2H), 6.95-6.84 (m, 2H), 5.54 (d, J=17.2 Hz, 1H), 5.31-5.28 (m, 1H), 4.47 (s, 2H), 4.01-3.95 (m, 1H), 3.22-3.16 (m, 1H), 2.75-2.71 (m, 2H), 2.46-2.40 (m, 2H)

Step 4: 2-(3-(benzyloxy)cyclobutyl)-3-fluorobenzaldehyde

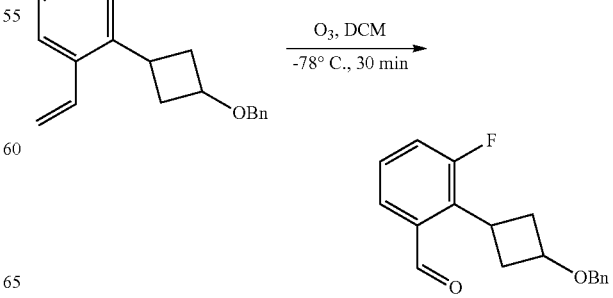

Ozone gas was purged to a stirred solution of 2-(3-(benzyloxy)cyclobutyl)-1-fluoro-3-vinylbenzene (step 3, 1.5 g, 5.31 mmol) in DCM (10 mL) at −78° C. for 30 min. Then reaction mixture was quenched with DMS (0.89 mL, 12.04 mmol) at the same temperature and stirred for another 50 min. Reaction mixture was diluted with water and extracted with DCM. Combined organic layers were washed with water, brine, dried over anhydrous Na$_2$SO$_4$, filtered and concentrated under reduced pressure to afforded crude compound. The crude product was purified by silica flash chromatography (10% ethyl acetate in hexane) to afford the title compound 2-(3-(benzyloxy)cyclobutyl)-3-fluorobenzaldehyde (0.55 g, 36%) as a light brown liquid. 5 $^1$H NMR (300 MHz, CDCl$_3$) δ 10.23 (s, 1H), 7.68-7.26 (m, 8H), 4.47 (s, 2H), 4.10-4.01 (m, 1H), 3.80-3.68 (m, 1H), 2.91-2.63 (m, 2H), 2.47-2.37 (m, 2H)

Step 5 &6: methyl 4-(2-(3-(benzyloxy)cyclobutyl)-3-fluorophenyl)-2-methyl-5-oxo-1,4,5,7-tetrahydrofuro[3,4-b]pyridine-3-carboxylate

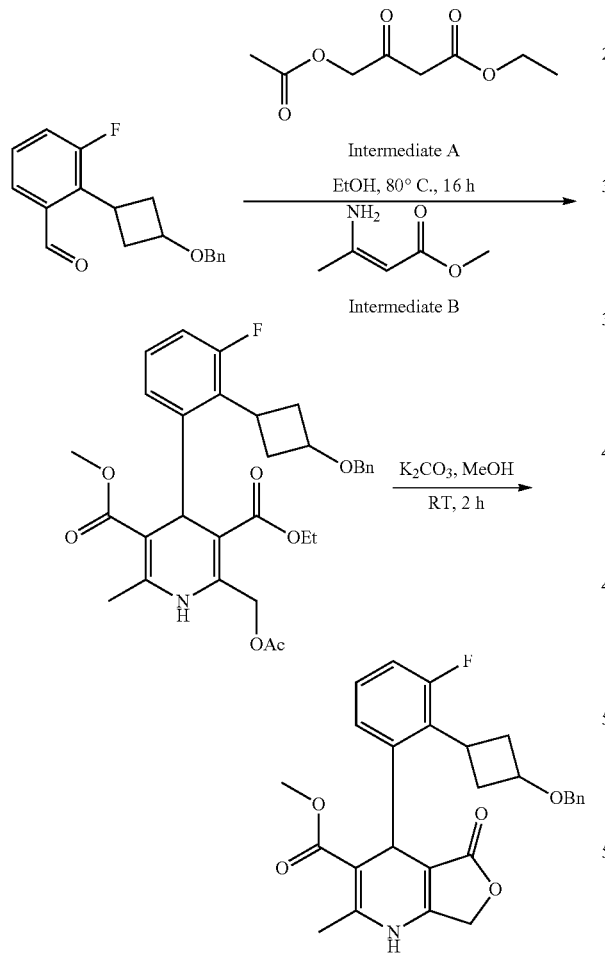

The title compound was synthesized using general method II (using the aldehyde from step 4, 0.55 g, 1.93 mmol). The crude product was purified by silica flash chromatography (80% ethyl acetate in hexane) to afford the title compound methyl 4-(2-(3-(benzyloxy)cyclobutyl)-3-fluorophenyl)-2-methyl-5-oxo-1,4,5,7-tetrahydrofuro[3,4-b]pyridine-3-carboxylate (0.31 g, 48%) as an off white solid.

LCMS Rt=1.566 min; MS m/z 462.05 [M−H]−; [Method 10]

Step 7: methyl 4-(3-fluoro-2-(3-hydroxycyclobutyl)phenyl)-2-methyl-5-oxo-1,4,5,7-tetrahydrofuro[3,4-b]pyridine-3-carboxylate

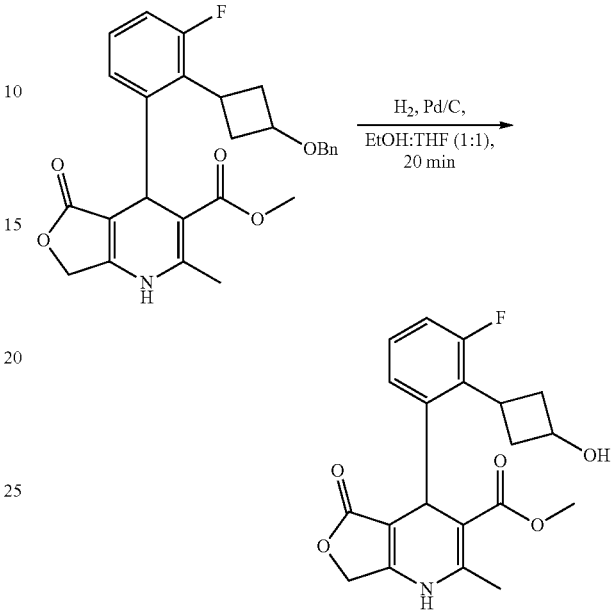

To the stirred solution of methyl 4-(2-(3-(benzyloxy)cyclobutyl)-3-fluorophenyl)-2-methyl-5-oxo-1,4,5,7-tetrahydrofuro[3,4-b]pyridine-3-carboxylate (step 6, 0.26 g, 0.56 mmol) in EtOH:THF (1:1, 10 mL) was added Pd/C (130 mg, 50 mol %) and the reaction mixture was stirred under H$_2$ atmosphere for 6 h at room temperature. Reaction mixture was filtered through celite bed and washed with ethanol, and filtrate was concentrated under reduced pressure to afford crude compound. Crude compound was purified by Prep HPLC (Column: ZORBAX (150 mm×21.2 mm), 5.0µ; Mobile Phase: A=WATER; B=ACN; Flow: 20 mL/min) to afford the title compound methyl 4-(3-fluoro-2-(3-hydroxycyclobutyl)phenyl)-2-methyl-5-oxo-1,4,5,7-tetrahydrofuro [3,4-b]pyridine-3-carboxylate (115 mg, 61%) as an off white solid.

LCMS Rt=1.395 min; MS m/z 372.1 [M−H]−; [Method 10]

Step 8: methyl 4-(3-fluoro-2-(3-fluorocyclobutyl)phenyl)-2-methyl-5-oxo-1,4,5,7-tetrahydrofuro[3,4-b]pyridine-3-carboxylate

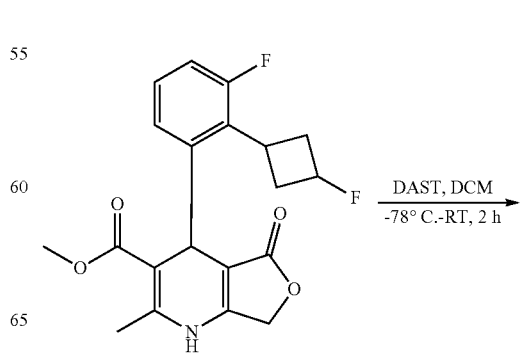

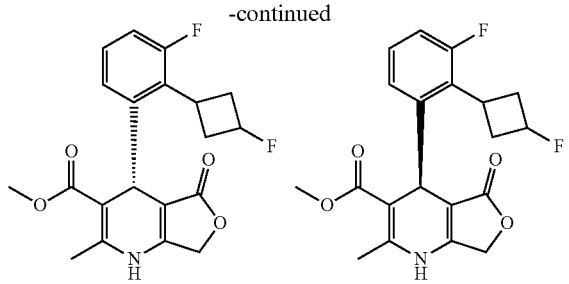

To a cooled stirring solution of methyl 4-(3-fluoro-2-(3-hydroxycyclobutyl)phenyl)-2-methyl-5-oxo-1,4,5,7-tetrahydrofuro[3,4-b]pyridine-3-carboxylate (step 7, 100 mg, 0.27 mmol) in DCM (1.5 mL) at −78° C., was added DAST (0.15 mL, 1.20 mmol) dropwise. The resulting reaction mixture was slowly allowed to warm to room temperature and stirred for 2 h. Water was added to the reaction mixture and product extracted with DCM. The combined organic layer was washed with saturated NaHCO₃ solution, water, brine, dried over anhydrous Na₂S04, filtered and concentrated under reduced pressure to afforded crude compound. Crude compound was purified by Prep HPLC (Column: ZORBAX (21.2 mm×150 mm); Mobile Phase: A=WATER; B=ACN; Flow: 20 ml/min) to afford the title compound methyl 4-(3-fluoro-2-(3-fluorocyclobutyl)phenyl)-2-methyl-5-oxo-1,4,5,7-tetrahydrofuro[3,4-b]pyridine-3-carboxylate (17 mg, 17%) as an off white solid.

LCMS Rt=1.524 min; MS m/z 374.15 [M−H]−; [Method 10]

The racemic sample was separated into its enantiomers by chiral HPLC (Column: REGIS WHELK, 250 MM×21.2 MM×5 MICRON); Mobile Phase: N-HEXANE (A) EtOH/ MeOH, 1:1 (B), FLOW: 15 ML/Min).

Example 20

5 mg of the first eluting enantiomer as an off white solid.

Chiral HPLC Rt=7.987 min (Column: REGIS, (S,S) WHELK-01 (150×4.6 mm, 5 micron); Mobile Phase: A=n-HEXANE, B=ETHANOL; Flow: 1.0 ml/min).

LCMS Rt=1.556 min; MS m/z 375.8 [M+H]+; [Method 10]

$^1$H NMR (400 MHz, DMSO-d₆) δ 9.81 (s, 1H), 7.18-7.15 (m, 1H), 6.98-6.93 (m, 2H), 5.60-5.21 (m, 1H), 5.02 (s, 1H), 4.80 (dd, J=19.6, 16.0 Hz, 2H), 4.60-4.51 (m, 1H), 3.43 (s, 3H), 2.93-2.59 (m, 4H), 2.31 (s, 3H).

Example 20b 6 mg of the second eluting enantiomer as an off white solid.

Chiral HPLC Rt=8.934 min (Column: REGIS, (S,S) WHELK-01 (150×4.6 mm, 5 micron); Mobile Phase: A=n-HEXANE, B=ETHANOL; Flow: 1.0 ml/min).

LCMS Rt=1.554 min; MS m/z 376.1 [M+H]+; [Method 10]

$^1$H NMR (400 MHz, DMSO-d₆) δ 9.81 (s, 1H), 7.18-7.15 (m, 1H), 6.98-6.93 (m, 2H), 5.60-5.21 (m, 1H), 5.02 (s, 1H), 4.80 (dd, J=19.6, 16.0 Hz, 2H), 4.60-4.51 (m, 1H), 3.43 (s, 3H), 2.93-2.59 (m, 4H), 2.31 (s, 3H).

Biological Data

Many known calcium channel activators have shown complex mechanisms of activating Ca$_v$1.2. These molecules not only increase peak currents, but also have additional mechanisms that increase intracellular calcium concentration, for example, by shifting the voltage sensitivity of the channel to more negative membrane potentials. FIG. 1 illustrates these additional mechanisms by depicting simulated cardiac action potentials from an epicardial environment and showing the impact of shifting the voltage of Ca$_v$1.2 activation to more negative membrane potentials at a Potential (mV) versus Time (ms). These additional mechanisms could drive or facilitate cardiovascular effects such as increase in blood pressure, change in heart rate or contractility, and/or arrhythmia due to QT prolongation. For example, the O'Hara-Rudy model was used to investigate the effect of Ca$_v$1.2 modulation on action potential duration and arrhythmic liability. It was identified that a >12 mV hyperpolarizing shift in the activation curve could potentially lead to >15% QT prolongation and an increased risk of arrhythmia. Therefore, minimizing any shifts in voltage sensitivity may lead to compounds with a reduced risk of QT prolongation and cardiac arrhythmia.

The compounds of formula (I) are highly potent Ca$_v$1.2 activators having a biophysical profile which minimizes the cardiovascular risks outlined above. First, the compounds of formula (I) limit their effects on the voltage sensitivity by minimizing hyperpolarizing shifts to <9 mV to mitigate for an arrhythmia potential. Second, the compounds of formula (I) increase Ca$_v$1.2 peak currents by no more than 2.5 fold, thereby limiting over-activation of the channel. Third, the compounds of formula (I) do not delay Ca$_v$1.2 channel inactivation, a pathophysiological mechanism underlying cardiac symptoms of Timothy Syndrome. Moreover, compounds of formula (I) are designed to maximize brain exposure by showing no significant efflux in the brain.

Generation and Maintenance of the Ca$_v$1.2-HEK293(AUX) Cell Line

The monoclonal Ca$_v$1.2-HEK293(AUX) cell line constitutively expresses human Ca$_v$1.2 alpha1 (α1) subunit (CACNA1C) and has doxycycline-inducible expression of the alpha2delta (α2Δ2) auxiliary subunit (CACNA2D2) and beta2 ((β2) auxiliary subunit (CACNB2). To generate the cell line, expression vectors pcDNA5H/FRT-TO-CACNA2D2-FCS-P2A-CACNB2 and pCMV6-entry-CACNA1C were established via gene synthesis and cloning. Here, pcDNA5.0/FRT-TO plasmid is from Invitrogen, pCMV6-entry is from Origene, FCS stands for Furin Cleavage Site, P2A is a peptide self-cleavage sequence derived from porcine teschovirus-1, and FRT is the Flippase recognition target site. Next, parental line Flp-In™ 293 T-Rex (Invitrogen) was transfected with pcDNA5H/FRT-TO-CACNA2D2-FCS-P2A-CACNB2 and Flippase vector pOG44 (Invitrogen) to establish targeted integration of the CACNA2D2-FCS-P2A-CACNB2 expression cassette into the pre-engineered FRT site in Flp-In™ 293 T-Rex. This intermediate cell line was then transfected with pCMV6-entry-CACNA1C to establish stable CACNA1C expression. Clonal isolation was achieved under Neomycin selection. A cell clone (2-19B) with good voltage-dependent Barium current (see electrophysiology methods below) was selected for characterization of Ca$_v$1.2 activators.

To maintain the cell line, cells were passaged twice per week. At each passage, growth media (Table 1) were completely removed and cells were rinsed sequentially with 10 mL of D-PBS and 5 mL of warm TrypLE™ Express Enzyme (Gibco). Both D-PBS and TrypLE™ Express Enzyme were immediately removed after rinsing. Plates were then placed at room temperature for 3-5 minutes. Next, 10 mL of warm 37° C. complete media was added to flush the cell-growing surface and collect dissociated cells. Cells were counted and seeded into new flasks, targeting a density of 2-3×10⁶ cells per T175 cm² flask.

TABLE 1

Growth medium for HEK293-Ca$_V$1.2(AUX) cells

| Reagent | Concentration |
|---|---|
| DMEM | |
| Heat inactivated fetal bovine serum | 10% |
| Hygromycin B | 100 ug/ml |
| Blasticidin | 10 ug/ml |
| Geneticin (G418) | 200 ug/mL |

Electrophysiological Characterization of Ca$_v$1.2 Activators Using Ca$_v$1.2-HEK293(AUX) Cell Line and QPatch 24 hours prior an electrophysiology experiment, doxycycline (1 μg/ml) was added to the growth medium (Table 1), and 25 μM of verapamil was co-applied to prevent calcium influx triggered cell death. Cell confluency should reach 70%-80% right before the experiment.

To harvest cells (from a T175 cm² flask as an example), growth media were removed completely, and the cells were rinsed with 10 mL of D-PBS. D-PBS was aspirated, and 10 mL of Detachin (Genlantis) was added and the plate was placed in a 37° C. incubator for 10 minutes. Detached cells were placed into a 15 mL conical tube and spun at 1000 rpm for 2 minutes. Supernatant was removed, and cells were re-suspended in QPatch complete media (Table 2) to desired cell density of 1.5-3 million cells per QPatch run. Each experimental run uses 1.5 mL of cells.

The cells suspension was taken to the Sophion QPatch platform that uses whole-cell voltage clamp to measure barium currents conducted through Ca$_v$1.2 on single-hole QPlates. Extracellular and intracellular patch clamp solutions are described in Tables 3 and 4, respectively. A dose-response assay protocol was used to determine the maximal fold change of peak inward current (Emax) and potency (EC$_{50}$) of each compound. The protocol had eight liquid periods. The first liquid period was to stabilize current amplitude, which was monitored using repetitive 200-ms voltage pulses stepping from −80 mV to 0 mV. The second liquid period was to determine baseline current amplitude in the presence of vehicle control, using a single 20-ms voltage pulse stepping from −80 mV to 0 mV. The third through eighth liquid periods were used to ascertain a 6-dose response to compound treatments, also using single 20-ms voltage pulses stepping from −80 mV to 0 mV. The EC$_{50}$ was generated using the following equation $I_{concentration}=I_{base}+(I_{full}-I_{base})*c^n/(XC_{50}{}^n+c^n)$, where c is the concentration and n is the Hill coefficient constant. $I_{full}$ is the maximal current achievable, and $I_{base}$ is 0. A channel biophysics assay protocol was used to determine channel gating properties including current-voltage relationship (IV curves), half-way channel activation voltage (V$_{1/2}$), rate of channel inactivation (tau), and amplitude of tail current. Among these, V1/2 was derived from fitting equation $G(V)=G_{Vmin}+(G_{Vmax}-G_{Vmin})/(1+\exp(-(V-V1/2)V_{slope}))$, where G stands for conductance, $G_{Vmin}$ equals 0, $G_{Vmax}$ is the maximal conductance, and $V_{slope}$ is a slope factor. G(V) was pre-calculated from equation $G(V)=I(V)/(V-0.06)$, for each experimentally applied depolarization potential (V) and the corresponding current amplitude (I(V)), and 0.06 in the equation was the experimentally determined reversal potential in volts. The protocol had four liquid periods. The first liquid period was to stabilize current amplitude, which was monitored using repetitive 200-ms voltage pulses stepping from −80 mV to 0 mV. Upon stabilization of current amplitude, a baseline value for the tau of inactivation was determined, via a single-exponential fit of the inactivation phase of the current trace. The second liquid period was to measure the baseline values constituting the current-voltage relationship in the presence of vehicle control, and the third liquid period was to measure the compound effect on the current-voltage relationship. During each of these two liquid periods, cells were given ten 20-ms voltage pulses, each stepping from −80 mV to an incremental value that ranges from −55 mV to +35 mV (increment size 10 mV). During the fourth liquid period a 200-ms voltage pulse from −80 mV to 0 mV was delivered again to measure the compound effect on tau of inactivation.

TABLE 2

QPatch complete media:

| Reagent | Concentration |
|---|---|
| CHO-Serum free Media (SFM) | |
| 1M HEPES | 25 mM |

TABLE 3

Extracellular solution for QPatch experiments

| Chemical | Concentration (mM) |
|---|---|
| Sodium Chloride | 145 |
| Barium Chloride | 10 |
| Potassium Chloride | 4 |
| HEPES (4-(2-hydroxyethyl)-1-piperazineethanesulfonic acid)) | 10 |
| HEPES | 10 |
| pH to 7.4 with NaOH for a final osmolarity of~315 mOSm, filter solution through 0.2 μM filter. | |

TABLE 4

Intracellular solution for QPatch experiments. The solution is a mix of 80% part two (stored at −80° C.) and 20% part one:

| Chemical | Concentration (mM) |
|---|---|
| Part One: | |
| Cesium Fluoride | 135 |
| HEPES (4-(2-hydroxyethyl)-1-piperazineethanesulfonic acid)) | 10 |
| Sodium Chloride | 10 |
| EGTA (Ethylene glycol-bis(2-aminoethylether)-N,N,N',N'-tetraacetic acid) | 1 |
| pH to 7.2 with CsOH for a final osmolarity of~295 mOSm, filter solution through 0.2 μM filter. | |
| Part Two: | |
| Cesium Chloride | 140 |
| EGTA (Ethylene glycol-bis(2-aminoethylether)-N,N,N',N'-tetraacetic acid) | 10 |
| HEPES (4-(2-hydroxyethyl)-1-piperazine-ethanesulfonic acid)) | 10 |
| Adenosine 5'-triphosphate magnesium salt | 5 |
| pH to 7.2 with KOH for a final osmolarity of~295 mOSm, filter solution through 0.2 μM filter. | |

Assessment of Compound Exposure—cFos Induction (PK-PD) Relationship in Wild-Type Mice Animal maintenance and ethics. All animals were housed with regulated temperature and light cycle (22° C., 12-hour light/12-hour dark cycle) with unrestricted access to food and water. All animal experiments were performed in accordance with institutional guidelines for the care and use of laboratory animals as approved by the Institutional Animal Care and Use Committee (IACUC) of the Novartis Institutes for BioMedical Research, Inc. (Cambridge, Mass., USA).

Compound administration and brain tissue collection. Wild-type C57BL/6J male mice were obtained from Jackson laboratories (Bar Harbor, Me.). The acute, single-dose effects of $Ca_v1.2$ activators of the present disclosure were evaluated in male eight-week old mice (n=6 mice per compound). Each compound was dissolved in 10% PEG300, 10% Solutol, 10% Cremophore EL, and 70% Phosphate Buffered Saline and administered intraperitoneal (i.p.) at a concentration of 1 mg/kg up to 30 mg/kg depending on the compound. Animals were euthanized one hour after compound administration via exsanguination under deep anesthesia. Blood was collected in EDTA tubes for downstream analysis of drug levels. Brains were rapidly removed from the skull, and the cerebral cortex and cerebellum were regionally dissected. Cerebellar samples were snap frozen in liquid nitrogen to assess compound exposure. Cortical samples for cFos assessment were placed in 500 µL of RNAlater solution (ThermoFisher) to preserve the integrity of RNA in the sample. Samples remained in RNAlater for at least 24 hours at 4° C. before moving to −80° C. for storage before processing.

Quantification of cFos mRNA induction. Tissue homogenization was performed using TissueLyser system for 96 well plates (Qiagen). First, frozen cortical samples were thawed, removed from RNAlater, and placed into TissueLyser tubes along with Buffer RLT containing 0.5% Reagent DX and one 5 mm TissueLyser metal bead. The TissueLyser tubes were loaded into a TissueLyser II tissue homogenizer for 3 rounds of homogenization, with each round lasting 5 minutes at 30 Hz bead-beating frequency. Total RNA was purified from the homogenate using RNeasy 96 Plus kit (Qiagen), RNA concentration and A260/A280 ratio were quantified via the Nanodrop (ThermoFisher), and all samples were normalized to 100 ng/µl concentration. RNA was reverse transcribed into cDNA using the Superscript III First-strand synthesis SuperMix Kit (ThermoFisher). For each sample, 6 µl of RNA (600 ng total) was mixed with 1 µL of Oligo dT and 1 µL of annealing buffer and heated to 65° C. for 5 minutes. Next, 10 µL of 2× First-Strand Reaction Mix and 2 µL of the Enzyme mix were added to achieve a total reaction volume of 20 µL. The samples were heated to 50° C. for 50 minutes then 85° C. for 5 minutes to complete cDNA synthesis.

Quantitative PCR was performed on the cDNA samples using Quantitect Multiplex RT-PCR kit (Qiagen) in a 384-well assay format. Each PCR well contained 2 µL of cDNA (60 ng total), 10 µL of RT-PCR mastermix, 1 µL of cFos FAM Taqman probe (Mm00487425_m1 (FAM) #4351368), 1 µL of GAPDH VIC Taqman probe (Mm99999915-g1 (VIC) #4448486), 0.2 µL of Multiplex RT mix and 5.8 µl of RNase-free water. On the ViiA7 Real-Time PCR system (ThermoFisher), the samples were heated to 95° C. for 15 minutes then cycled between 94° C. for 45 seconds and 60° C. for 45 seconds for 45 cycles. cFos Ct values were exported, normalized to GAPDH Ct values, and converted to relative fold change in expression using the delta-delta Ct relative quantification method. cFos fold changes between compound treatments and vehicle were analyzed by one-way ANOVA, followed by Tukey's post-hoc comparisons.

Quantification of compound exposure. Cerebellar tissue samples were homogenized in 4 mL of 20% acetonitrile and 80% Phosphate buffered saline for every 1 g of tissue (5× dilution). Tissue was homogenized using either of the following three methods: hand held probe system, TissueLyser system with 5 mm steel bead at a frequency of 30 s$^{-1}$ for 4 min, or OMNI Bead Ruptor Elite homogenizer for 30 seconds to 1 minute depending on tissue type. Tissue samples were added to a 96-well plate (12.5 µL sample) and processed for quantification by mass spectrometry.

Results

TABLE 5

Compound data

| Example | QPatch EC50 (µM) | QPatch Emax | Biophysics voltage shift (mV) | Brain: blood ratio | % ↑cFOS mRNA cortex (3 mg/kg ip) | % ↑cFOS mRNA cortex (10 mg/kg ip) |
|---|---|---|---|---|---|---|
| 1 | 0.13# | 2.0 | −4.5 | 1.1 | 169% | 350% |
| 2 | 0.17* | 1.6 | −1.9 | 3.4 | 23% | 203% |
| 3 | 0.08 | 1.8 | −6.6 | nd | nd | nd |
| 4 | 0.11* | 2.1 | −4.5 | 1.2 | 247% | 398% |
| 5 | 0.053 | 2.5 | −7.2 | nd | nd | nd |
| 6 | 0.081 | 2.6 | −4.8 | nd | nd | nd |
| 7 | 0.03 | 1.7 | −6.6 | 1.7 | 158% | nd |
| 8 | 0.218 | 1.6 | nd | nd | nd | nd |
| 9 | 0.13 | 1.5 | −6.6 | 2.3 | 112% | nd |
| 10 | 0.04 | 2.2 | nd | 0.9 | 204% | nd |
| 11 | 0.04 | 1.4 | −6.8 | nd | nd | nd |
| 12 | 0.11 | 1.4 | −7.4 | 0.8 | 128% | nd |
| 13 | 0.22 | 1.5 | −4.8 | 1.0 | 165% | 281% |
| 14 | 0.065* | 1.8 | −1.9 | 1.7 | 228% | 364% |
| 15 | 0.05 | 2 | −6.6 | 1.3 | 169% | nd |
| 16 | 0.004 | 1.5 | −3.3 | 0.6 | 121% | nd |
| 17 | 0.271 | 1.8 | −6.6 | nd | nd | nd |
| 18 | 0.102 | 2.2 | −6.5 | nd | nd | nd |
| 19 | 0.012 | 1.7 | −1.8 | 2.9 | 138% | nd |
| 20 | 0.086 | 1.6 | −6.1 | nd | nd | nd |

QPatch was conducted as a 6-point dose response with 10 individual determinations at each concentration. Unless stated only one experimental replicate (n = 1)

*n = 2 n = 3 nd = not determined

Comparative Examples

Other $Ca_v1.2$ activators are known, however these compounds are not as potent and/or do not have the desired biophysical properties needed to activate the channel and have sufficient brain exposure, while at the same time minimizing cardiovascular risks, such as increase in blood pressure, altered heart rate or contractility, and/or arrhythmia due to QT prolongation.

TABLE 6

Comparative examples to other known CaV1.2 activators

| Structure Name | QPatch EC50 (μM) | QPatch Emax | Biophysics voltage shift (mV) | Brain:blood ratio |
|---|---|---|---|---|
| Reported calcium channel activators (single enantiomers of reported racemates) showing various Qpatch profiles (Emax & V-shift) | | | | |
| (BayK8644) | 0.021 | 3.9 | −10.11 | Not determined |
| (RS30124) | 0.45 | 4.3 | −15.4 | Not determined |
| (CPG028392) | 0.28 | 2.2 | −6.7 | 0.23 |
| CAS# 85825-32-7 | 2.24 | 1.4 | Not determined | Not determined |

TABLE 6-continued

Comparative examples to other known CaV1.2 activators

| Structure Name | QPatch EC50 (μM) | QPatch Emax | Biophysics voltage shift (mV) | Brain:blood ratio |
|---|---|---|---|---|
| Reported calcium channel activators (single enantiomers of reported racemates) showing various Qpatch profiles (Emax & V-shift) | | | | |
| CAS# 85825-31-6 | 0.36 | 1.4 | −4.3 | Not determined |
| CAS# 92638-18-1 | 0.51 | 1.7 | −7.1 | Not determined |
|  | 0.93 | 1.9 | Not determined | Not determined |

What is claimed is:

1. A compound according to formula (I) or a pharmaceutically acceptable salt thereof

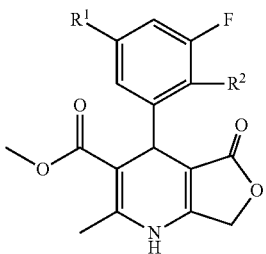

wherein:
R¹ is H or halo; and
R² is ethyl, isopropyl, isopropenyl, cyclopropyl, or cyclobutyl each of which is optionally substituted with one to three halo.

2. The compound according to claim 1 of formula (Ia) or a pharmaceutically acceptable salt thereof,

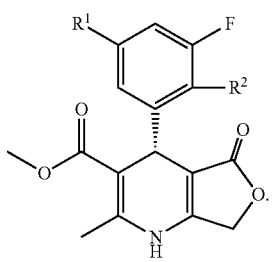

3. The compound according to claim 1 of formula (Ib) or a pharmaceutically acceptable salt thereof

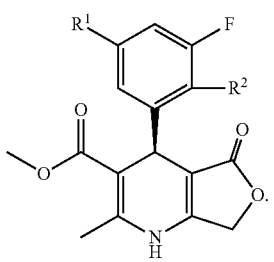

4. The compound according to claim 1 wherein R¹ is H or F.

5. The compound according to claim 1 wherein R¹ is H.

6. The compound according to claim 1 wherein R¹ is F.

7. The compound according to claim 1 wherein R² is ethyl, isopropyl, isopropenyl, cyclopropyl or cyclobutyl each of which is optionally substituted with one to three F.

8. The compound according to claim 1 wherein R² is cyclopropyl optionally substituted with one to three F.

9. The compound according to claim 1 wherein R² is ethyl optionally substituted with one to three F.

10. The compound according to claim 1 wherein R² is isopropyl optionally substituted with one to three F.

11. The compound according to claim 1 selected from the group consisting of:
  Methyl (S)-4-(2-((R)-2,2-difluorocyclopropyl)-3-fluorophenyl)-2-methyl-5-oxo-1,4,5,7-tetrahydrofuro[3,4-b]pyridine-3-carboxylate;
  Methyl (S)-4-(2-((S)-2,2-difluorocyclopropyl)-3-fluorophenyl)-2-methyl-5-oxo-1,4,5,7-tetrahydrofuro[3,4-b]pyridine-3-carboxylate;
  Methyl (S)-4-(2-cyclobutyl-3-fluorophenyl)-2-methyl-5-oxo-1,4,5,7-tetrahydrofuro [3,4-b]pyridine-3-carboxylate;
  Methyl (S)-4-(2-cyclopropyl-3-fluorophenyl)-2-methyl-5-oxo-1,4,5,7-tetrahydrofuro[3,4-b]pyridine-3-carboxylate;
  Methyl (S)-4-(2-((R)-2,2-difluorocyclopropyl)-3,5-difluorophenyl)-2-methyl-5-oxo-1,4,5,7-tetrahydrofuro[3,4-b]pyridine-3-carboxylate;
  Methyl (S)-4-(2-((S)-2,2-difluorocyclopropyl)-3,5-difluorophenyl)-2-methyl-5-oxo-1,4,5,7-tetrahydrofuro[3,4-b]pyridine-3-carboxylate;
  Methyl (S)-4-(3,5-difluoro-2-((S)-1-fluoroethyl)phenyl)-2-methyl-5-oxo-1,4,5,7-tetrahydrofuro[3,4-b]pyridine-3-carboxylate;
  Methyl (S)-4-(3,5-difluoro-2-((R)-1-fluoroethyl)phenyl)-2-methyl-5-oxo-1,4,5,7-tetrahydrofuro[3,4-b]pyridine-3-carboxylate;
  Methyl (S)-4-(3-fluoro-2-(2-fluoropropan-2-yl)phenyl)-2-methyl-5-oxo-1,4,5,7-tetrahydrofuro[3,4-b]pyridine-3-carboxylate;
  Methyl (S)-4-(3-fluoro-2-(2,2,2-trifluoroethyl)phenyl)-2-methyl-5-oxo-1,4,5,7-tetrahydrofuro[3,4-b]pyridine-3-carboxylate;
  Methyl (S)-4-(3-fluoro-2-((S)-1-fluoroethyl)phenyl)-2-methyl-5-oxo-1,4,5,7-tetrahydrofuro[3,4-b]pyridine-3-carboxylate;
  Methyl (S)-4-(3-fluoro-2-((R)-1-fluoroethyl)phenyl)-2-methyl-5-oxo-1,4,5,7-tetrahydrofuro[3,4-b]pyridine-3-carboxylate;
  Methyl (S)-4-(2-((R)-1,2-difluoroethyl)-3-fluorophenyl)-2-methyl-5-oxo-1,4,5,7-tetrahydrofuro[3,4-b]pyridine-3-carboxylate;
  Methyl (S)-4-(2-((S)-1,2-difluoroethyl)-3-fluorophenyl)-2-methyl-5-oxo-1,4,5,7-tetrahydrofuro[3,4-b]pyridine-3-carboxylate;
  Methyl (S)-4-(2-ethyl-3,5-difluorophenyl)-2-methyl-5-oxo-1,4,5,7-tetrahydrofuro[3,4-b]pyridine-3-carboxylate;
  Methyl (S)-4-(2-ethyl-3-fluorophenyl)-2-methyl-5-oxo-1,4,5,7-tetrahydrofuro[3,4-b]pyridine-3-carboxylate;
  (S)-methyl 4-(2-cyclopropyl-3,5-difluorophenyl)-2-methyl-5-oxo-1,4,5,7-tetrahydrofuro[3,4-b]pyridine-3-carboxylate;
  (S)-methyl 4-(3-fluoro-2-isopropylphenyl)-2-methyl-5-oxo-1,4,5,7-tetrahydrofuro[3,4-b]pyridine-3-carboxylate;
  (S)-methyl 4-(3-fluoro-2-(3,3,3-trifluoroprop-1-en-2-yl)phenyl)-2-methyl-5-oxo-1,4,5,7-tetrahydrofuro[3,4-b]pyridine-3-carboxylate;
  (S)-methyl 4-(2-(2,2-difluoroethyl)-3-fluorophenyl)-2-methyl-5-oxo-1,4,5,7-tetrahydrofuro[3,4-b]pyridine-3-carboxylate;
  Methyl (S)-4-(3,5-difluoro-2-isopropylphenyl)-2-methyl-5-oxo-1,4,5,7-tetrahydrofuro[3,4-b]pyridine-3-carboxylate;
  (S)-methyl 4-(3,5-difluoro-2-(3,3,3-trifluoroprop-1-en-2-yl)phenyl)-2-methyl-5-oxo-1,4,5,7-tetrahydrofuro[3,4-b]pyridine-3-carboxylate; and methyl (S)-4-(3-fluoro-2-(3-fluorocyclobutyl)phenyl)-2-methyl-5-oxo-1,4,5,7-tetrahydrofuro[3,4-b]pyridine-3-carboxylate, or a pharmaceutically acceptable salt thereof.

12. A pharmaceutical composition comprising a compound according to claim 1 or a pharmaceutically acceptable salt thereof and a pharmaceutically acceptable excipient.

13. A method for the treatment of schizophrenia, bipolar disorder, major depressive disorder, substance use disorder, ADHD, Phelan McDermid Syndrome, autism spectrum disorder, multiple sclerosis, frontotemporal dementia, Alzheimer's disease, Brugada Syndrome, Short QT syndrome, or early repolarization syndrome comprising administration of an effective amount of a compound according to claim 1, or a pharmaceutically acceptable salt thereof, to a patient in need of treatment thereof.

14. A method for the treatment of schizophrenia, bipolar disorder, major depressive disorder, substance use disorder, ADHD, Phelan McDermid Syndrome, autism spectrum disorder, multiple sclerosis, frontotemporal dementia, Alzheimer's disease, Brugada Syndrome, Short QT syndrome, or early repolarization syndrome comprising administration of a compound according to claim 1, or a pharmaceutically acceptable salt thereof, to a patient in need of treatment thereof.

15. A pharmaceutical composition comprising a compound according to claim 11 or a pharmaceutically acceptable salt thereof and a pharmaceutically acceptable excipient.

16. A method for the treatment of schizophrenia, bipolar disorder, major depressive disorder, substance use disorder, ADHD, Phelan McDermid Syndrome, autism spectrum disorder, multiple sclerosis, frontotemporal dementia, Alzheimer's disease, Brugada Syndrome, Short QT syndrome, or early repolarization syndrome comprising administration of an effective amount of a compound according to claim 11, or a pharmaceutically acceptable salt thereof, to a patient in need of treatment thereof.

17. A method for the treatment of schizophrenia, bipolar disorder, major depressive disorder, substance use disorder, ADHD, Phelan McDermid Syndrome, autism spectrum disorder, multiple sclerosis, frontotemporal dementia, Alzheimer's disease, Brugada Syndrome, Short QT syndrome, or early repolarization syndrome comprising administration of a compound according to claim 11, or a pharmaceutically acceptable salt thereof, to a patient in need of treatment thereof.

* * * * *